United States Patent
Brimble et al.

(10) Patent No.: US 11,014,960 B2
(45) Date of Patent: *May 25, 2021

(54) AMINO ACID AND PEPTIDE CONJUGATES AND USES THEREOF

(71) Applicant: AUCKLAND UNISERVICES LIMITED, Auckland (NZ)

(72) Inventors: Margaret Anne Brimble, Auckland (NZ); Peter Roderick Dunbar, Auckland (NZ); Geoffrey Martyn Williams, Auckland (NZ); Daniel Verdon, Auckland (NZ)

(73) Assignee: AUCKLAND UNISERVICES LIMITED, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 16/251,136

(22) Filed: Jan. 18, 2019

(65) Prior Publication Data

US 2019/0256552 A1 Aug. 22, 2019

Related U.S. Application Data

(63) Continuation of application No. 15/535,956, filed as application No. PCT/IB2015/059901 on Dec. 22, 2015, now Pat. No. 10,253,062.

(60) Provisional application No. 62/096,106, filed on Dec. 23, 2014.

(51) Int. Cl.
| | | |
|---|---|---|
| *A61K 38/00* | (2006.01) | |
| *C07K 1/107* | (2006.01) | |
| *A61K 39/12* | (2006.01) | |
| *C07C 323/58* | (2006.01) | |
| *A61K 47/54* | (2017.01) | |
| *C07K 14/005* | (2006.01) | |
| *A61K 39/00* | (2006.01) | |

(52) U.S. Cl.
CPC ............ *C07K 1/1075* (2013.01); *A61K 39/12* (2013.01); *A61K 47/542* (2017.08); *C07C 323/58* (2013.01); *C07K 14/005* (2013.01); *A61K 39/00* (2013.01); *A61K 2039/6018* (2013.01); *C07C 2603/18* (2017.05); *C12N 2710/16222* (2013.01); *C12N 2710/16234* (2013.01)

(58) Field of Classification Search
None
See application file for complete search history.

(56) References Cited

U.S. PATENT DOCUMENTS

| | | | |
|---|---|---|---|
| 4,439,425 A | 3/1984 | Tarcsay et al. | |
| 4,743,543 A | 5/1988 | Kortright | |
| 4,914,021 A | 4/1990 | Toth et al. | |
| 4,918,164 A | 4/1990 | Hellstrom et al. | |
| 4,921,789 A | 5/1990 | Salem et al. | |
| 4,921,790 A | 5/1990 | O'Brien | |
| 4,939,240 A | 7/1990 | Chu et al. | |
| 4,963,484 A | 10/1990 | Kufe | |
| 5,053,489 A | 10/1991 | Kufe | |
| 5,110,911 A | 5/1992 | Samuel et al. | |
| 5,808,005 A | 9/1998 | Codington et al. | |
| 5,849,893 A | 12/1998 | Lubberding et al. | |
| 5,855,866 A | 1/1999 | Thorpe et al. | |
| 5,892,020 A | 4/1999 | Mezes et al. | |
| 5,994,294 A | 11/1999 | Garvey et al. | |
| 6,024,964 A | 2/2000 | Jung et al. | |
| 6,074,650 A | 6/2000 | Jung et al. | |
| 6,310,180 B1 | 10/2001 | Tam | |
| 6,723,695 B1 | 4/2004 | Burrows et al. | |
| 6,828,329 B2 | 12/2004 | Cai et al. | |
| 7,491,395 B2 | 2/2009 | Stegmann | |
| 7,569,225 B2 | 8/2009 | Jackson et al. | |
| 7,619,057 B2 | 11/2009 | Wang et al. | |
| 7,833,532 B2 | 11/2010 | Jackson et al. | |
| 7,887,833 B2 | 2/2011 | Heldman et al. | |
| 7,960,507 B2 | 6/2011 | Eisenbach et al. | |
| 8,241,639 B2 | 8/2012 | Middeldorp | |
| 8,309,096 B2 | 11/2012 | Blais et al. | |
| 8,367,067 B2 | 2/2013 | Jackson et al. | |
| 8,481,051 B2 | 7/2013 | Kuzushima et al. | |
| 8,492,514 B2 | 7/2013 | Kessler et al. | |
| 9,314,521 B2 | 4/2016 | Ossendorp et al. | |

(Continued)

FOREIGN PATENT DOCUMENTS

| | | |
|---|---|---|
| CA | 1333563 | 12/1994 |
| CN | 1709510 A | 12/2005 |

(Continued)

OTHER PUBLICATIONS

Luo, F. et al., "Copper(II)-Catalyzed Esterification of Arenecarboxylic Acids with Aryl- and Vinyl-Substituted Trimethoxysilanes" Synthesis (2010) 12:2005-2010.

(Continued)

*Primary Examiner* — Jeanette M Lieb

(74) *Attorney, Agent, or Firm* — Dann, Dorfman, Herrell and Skillman, P.C.; Robert C. Netter, Jr.

(57) ABSTRACT

The present invention relates to peptides, and amino acid and peptide conjugates, methods for making amino acid and peptide conjugates, conjugates produced by the methods, pharmaceutical compositions comprising the peptides and conjugates, methods of eliciting immune responses in a subject and methods of vaccinating a subject, uses of the peptides and conjugates for the same, and uses of the peptides and conjugates in the manufacture of medicaments for the same.

18 Claims, 3 Drawing Sheets

Specification includes a Sequence Listing.

(56) References Cited

U.S. PATENT DOCUMENTS

| | | |
|---|---|---|
| 2001/0039669 A1* | 11/2001 | Douvas .................. C12N 15/86 800/278 |
| 2004/0006242 A1 | 1/2004 | Hawkins et al. |
| 2007/0048329 A1 | 3/2007 | Khanna et al. |
| 2007/0191314 A1 | 8/2007 | Klucker et al. |
| 2008/0139464 A1 | 6/2008 | Gnjatic et al. |
| 2008/0233143 A1 | 9/2008 | Jackson et al. |
| 2009/0081248 A1 | 3/2009 | Paterson et al. |
| 2009/0123488 A1 | 5/2009 | Goldstein |
| 2009/0130134 A1 | 5/2009 | Pancre et al. |
| 2009/0136537 A1 | 5/2009 | Evans et al. |
| 2009/0202584 A1 | 8/2009 | Thomson et al. |
| 2009/0246211 A1 | 10/2009 | Henri et al. |
| 2009/0258917 A1 | 10/2009 | Pelcman et al. |
| 2010/0021468 A1 | 1/2010 | Wang et al. |
| 2010/0092500 A1 | 4/2010 | Jackson et al. |
| 2010/0129385 A1 | 5/2010 | Jackson et al. |
| 2010/0266623 A1 | 10/2010 | Jackson et al. |
| 2011/0172256 A1 | 7/2011 | Lin et al. |
| 2011/0262473 A1 | 10/2011 | Jackson et al. |
| 2011/0280899 A1 | 11/2011 | Jackson et al. |
| 2012/0231030 A1 | 9/2012 | Derouazi et al. |
| 2012/0244132 A1 | 9/2012 | Stauss et al. |
| 2012/0328660 A1 | 12/2012 | Tsuji et al. |
| 2012/0329830 A1 | 12/2012 | Cheng et al. |
| 2013/0018064 A1 | 1/2013 | Paras et al. |
| 2013/0029358 A1 | 1/2013 | Valmori et al. |
| 2013/0039942 A1 | 2/2013 | Kornbluth et al. |
| 2013/0045203 A1 | 2/2013 | Joshi et al. |
| 2013/0183377 A1 | 7/2013 | Agrewala et al. |
| 2013/0230544 A1 | 9/2013 | Jackson et al. |
| 2014/0086888 A1 | 3/2014 | Heslop et al. |
| 2014/0112975 A1 | 4/2014 | Kiessling et al. |
| 2017/0095554 A1 | 4/2017 | Brimble et al. |

FOREIGN PATENT DOCUMENTS

| | | |
|---|---|---|
| EP | 0376075 A2 | 7/1990 |
| EP | 1666056 A1 | 6/2006 |
| EP | 2465520 A2 | 6/2012 |
| EP | 2608806 B1 | 10/2017 |
| JP | 8248579 | 9/1996 |
| WO | 9524925 | 9/1995 |
| WO | 9745444 | 12/1997 |
| WO | 9902550 | 1/1999 |
| WO | 1999014326 A1 | 3/1999 |
| WO | 9918206 | 4/1999 |
| WO | 0044758 A1 | 8/2000 |
| WO | 2001007917 A1 | 2/2001 |
| WO | 01/036453 A2 | 5/2001 |
| WO | 2001055393 A2 | 8/2001 |
| WO | 2002026778 A2 | 4/2002 |
| WO | 0247727 A1 | 6/2002 |
| WO | 2003/104428 A2 | 12/2003 |
| WO | 03099195 A2 | 12/2003 |
| WO | 2004001424 A1 | 12/2003 |
| WO | 2004014956 A1 | 2/2004 |
| WO | 2004014957 A1 | 2/2004 |
| WO | 2004041849 A1 | 5/2004 |
| WO | 2005012270 A2 | 2/2005 |
| WO | 2006/106435 A2 | 10/2006 |
| WO | 2008/089074 A9 | 7/2008 |
| WO | 2008/151197 A2 | 12/2008 |
| WO | 2010028246 A2 | 3/2010 |
| WO | 2010/115229 A1 | 10/2010 |
| WO | 2011156686 A2 | 12/2011 |
| WO | 2012020215 A1 | 2/2012 |
| WO | 2012069188 A1 | 5/2012 |
| WO | 2012123755 A1 | 9/2012 |
| WO | 2012158122 A1 | 11/2012 |
| WO | 2012/038055 A1 | 12/2012 |
| WO | 2013024282 A2 | 2/2013 |
| WO | 2013036543 A2 | 3/2013 |
| WO | 2013049941 A1 | 4/2013 |
| WO | 2013181597 A2 | 12/2013 |
| WO | 2014088432 A1 | 6/2014 |
| WO | 2014207708 A1 | 12/2014 |
| WO | 2016103192 A1 | 6/2016 |
| WO | 2017/145097 A2 | 8/2017 |
| WO | 2017145097 A2 | 8/2017 |

OTHER PUBLICATIONS

Harndahl, M., et al., "Large scale analysis of peptide-HLA class I interactions" (2010) Immune Epitope Database (IEDB), available at http://www.iedb.org/reference/1019514.

Rasmussen, M., et al., "Large scale analysis of peptide—HLA-I stability" (2014) Immune Epitope Database (IEDB), available at http://www.iedb.org/reference/1028285.

Rasmussen, M., et al., "Describing the peptide binding specificity of HLA-C molecules" (2014) Immune Epitope Database (IEDB), available at http://www.iedb.org/reference/1028231.

Harndahl, M., et al., "Large scale analysis of peptide-HLA class I interactions" (2007) Immune Epitope Database (IEDB), available at http://www.iedb.org/reference/1006442.

Rasmussen, M., et al., "Large scale analysis of peptide—HLA-I stability" (2014) Immune Epitope Database (IEDB), available at http://www.iedb.org/reference/1028288.

Rasmussen, M., et al., "Describing the Peptide Binding Specificity of HLA-C" J. Immunol. (2012) 188 (1 Supplement):106.41, Abstract.

Meyer, K.H., et al., "Antibodies against neuroactive amino acids and neuropeptides. I. A new two-step procedure for their conjugation to carrier proteins and the production of an anti-Met-enkephalin antibody reactive with glutaraldehyde-fixed tissue" J. Histochem. Cytochem. (1991) 39(6):749-60.

IP Australia, Examination Report No. 1 for standard application, Application No. AU 2019200884, dated Oct. 31, 2019, 3 pages.

International Preliminary Report on Patentability, Appln. No. PCT/IB2017/051054, dated Aug. 29, 2018.

Krug, et al., "Molecular Dynamics of the alpha-Helical Epitope of a Novel Synthetic Lipopeptide Foot-and-Mouth Disease Virus Vaccine" Biopolymers (1989) 28:499-512.

Moyle, et al., "Self-Adjuvanting Lipopeptide Vaccines" Current Med. Chem. (2008) 15:506-516.

Thornber, C.W., "Isosterism and molecular modification in drug design" Chem. Soc. Rev. (1979) 8:563-580.

Pan, et al., "Recombinant adeno-associated virus encoding Epstein-Barr virus latent membrane proteins fused with heat shock protein as a potential vaccine for nasopharyngeal carcinoma" Mol. Cancer Ther. (2009) 8(9):2754-2761.

Wang, et al., "Widespread sequence variation in the Epstein-Barr virus latent membrane protein 2A gene among northern Chinese isolates" Journal of General Virology (2010) 91:2564-2573.

Agnihotri, et al., "Structure-Activity Relationships in Toll-Like Receptor 2-Agonists Leading to Simplified Monoacyl Lipopeptides" J. Med. Chem. (2011) 54(23):8148-8160.

International Search Report and Written Opinion, Appln. No. PCT/IB2018/056611, dated Nov. 6, 2018.

Yang, et al., "Lipidation of Cysteine or Cysteine-Containing Peptides Using the Thiol-Ene Reaction (CLipPA)" Eur. J. Organic Chem. (2016) 2016:2608-2616.

Lu X. J. et al, "Isopentenyl-Diphosphate Isomerase: Irreversible Inhibition by 3-Methyl-3,4-epoxybutyl Diphosphate", Biochemistry, 1992, 31, 9955-9960.

CAS RN 1690273-81-4; STN Entry Date Apr. 23, 2015; D-Valine, 3-[(1,3-dioxan-4-ylmethyl)thio].

CAS RN 1690246-56-0; STN Entry Date Apr. 23, 2015; L-Valine, 3-[(1,3-dioxan-4-ylmethyl)thio].

CAS RN 1500650-08-7; STN Entry Date Dec. 22, 2013; L-Cysteine, S-(1,3-dioxan-4-ylmethyl)-N-formyl.

CAS RN 1500646-17-2; STN Entry Date Dec. 22, 2013; L-Homocysteine, S-(1,3-dioxan-4-ylmethyl)-, methyl ester.

CAS RN 1499966-80-1; STN Entry Date Dec. 20, 2013.

CAS RN 1498306-02-7; STN Entry Date Dec. 18, 2013; L-Cysteine, S-(1,3-dioxan-4-ylmethyl)-, methyl ester.

(56) References Cited

OTHER PUBLICATIONS

CAS RN 1190622-73-1; STN Entry Date Oct. 29, 2009; L-Cysteine, S-(1,3-dioxan-4-ylmethyl).
Kurimura et al., "Structure-activity relationship of lipopeptide from outer membrane of *Escherichia coli* and synthesis of highly immunopotenting lipopeptide derivatives with an achiral lipo-part," Chem. Pharm. Bull. (1993) 41(3) pp. 627-629.
Shimizu, T. et al., "Mitogenic activity and the induction of tumor necrosis factor by lipopeptide in the outer membrane of *Escherichia coli*," Biol. Pharm. Bull. (1994) 17(7) pp. 980-982.
Ellervik, U. et al., "Glycosylation with n-troc-protected glycosyl donors," Carb. Res. (1996) 280, pp. 251-260.
Yi, L. et al., "Semisynthesis of Prenylated Rab GTPases by Click Ligation," Chem. Bio. Chem., 2011, 12, pp. 2413-2417.
Salunke D.R. et al., "Structure-Activity Relationships in Human Toll-like Receptor 2-Sepcific Monoacyl Lipopeptidfes," Journal of Medicinal Chemistry, 2012, 55, pp. 3353-3363.
Dondoni A. et al., "A New Ligation Strategy for Peptide and Protein Glycosylation: Photoinduced Thiol-Ene Coupling," Chemistry A European Journal, 2009, 15, pp. 11444-11449.
Lau, Y.F. et al., "Lipid-containing mimetics of natural triggers of innate immunity as CTL-inducing influenza vaccines." Internatioanl Immunology, 2006, vol. 18, No. 12, pp. 1801-1813.
T. Gemma et al., "Racemization-Free Synthesis of S-Alkylated Cysteines via Thiol-ene Reaction," J. Org. Chem., 2008, 73, pp. 3646-3649.
NCBI accession No. NP 001318.1 (http://www.ncbi.nim.nih.gov/protein/NP_001318.1), Apr. 13, 2013.
EP Appln, No. 14818659.6, European Extended Search Report, dated Jan. 10, 2017, 6 pages.
Boeckler, C. et al., "Design and Synthesis of Thiol-Reactive Lipopeptides," Bioorganic & Medicinal Chemistry Letters, 1998, vol. 8, pp. 2055-2058.
Wright, T.H. et al., "Direct Peptide Lipidation through Thiol-Ene Coupling Enables Rapid Synthesis and Evaluation of Self-Adjuvanting Vaccine Candidates," Angewandte Chemis International Edition, 2013, vol. 52, No. 41, pp. 10616-10619.
Cai, H. et al., "Fully Synthetic Self-Adjuvanting Thioether-Conjugated Glycopeptide-Lipopeptide Antitumor Vaccines for the Induction of Complement-Dependent Cytotoxicity against Tumor Cells," Chemistry European Journal, 2013, vol. 19, pp. 1962-1970.
Supplementary European Search Report, Appin. No. EP 15 87 2074, dated Mar. 2, 2018.
Hauschildt, S. et al., "Induction and activity of NO synthase in bone-marrow-derived macrophages are independent of Ca2", Biochemical Journal, 1990, vol. 270, Issue: 2, pp. 351-356.
Liu, C. et al., "Chemical Ligation Approach to Form a Peptide Bond between Unprotected Peptide Segments. Concept and Model Study", Journal of the American Chemical Society, 1994, vol. 116, Issue: 10, pp. 4149-4153.
Chang, Y., et al., "Characterization of Modified Peptides by Tandem Mass Spectrometry", Analytical Science & Technology, 1995, vol. 8, Issue: 4, pp. 849-854.
Botti, P., et al., "Cyclic Peptides from Linear Unprotected Peptide Precursors through Thiazolidine Formation", Journal of the American Chemical Society, 1996, vol. 118, Issue: 42, pp. 10018-10024.
Miao, Z., et al., "Bidirectional Tandem Pseudoproline Ligations of Proline-Rich Helical Peptides", Journal of the American Chemical Society, 2000, vol. 122, Issue: 18, pp. 4253-4260.
Maruyama, Y., et al., "Synthesis of Immunoadjuvant Conjugates With Hiv-Derived Peptide Inducing Peptide-Specific Antibody", Chemical & Pharmaceutical Bulletin, 1994, vol. 42, Issue: 8, pp. 1709-1711.
Shimizu, T., et al., "Antibody-Producing Effects in Mice by Synthetic lmmunoactive Lipopeptides with the Conjugated Amino Acid Sequence of gp120 in Human Immunodeficiency Virus", Biological & Pharmaceutical Bulletin, 1996, vol. 19, Issue: 10, pp. 1271-1274.
Luesch, H., et al., "Isolation and Structure of the Cytotoxin Lyngbyabellin B and Absolute Configuration of Lyngbyapeptin A from the Marine Cyanobacterium Lyngbya majuscule", Journal of Natural Products, 2000, vol. 63, Issue: 10, pp. 1437-1439.
Milligan, K., et al., "Lyngbyabellin B, a Toxic and Antifungal Secondary Metabolite from the Marine Cyanobacterium Lyngbya majuscule", Journal of Natural Products, 2000, vol. 63, Issue: 10, pp. 1440-1443.
Marquez, B., et al., "Structure and Absolute Stereochemistry of Hectochlorin, a Potent Stimulator of Actin Assembly", Journal of Natural Products, 2002, vol. 65, Issue: 6, pp. 866-871.
Yokokawa, F., et al., "Total syntheses of lyngbyabellins A and B, potent cytotoxic lipopeptides from the marine cyanobacterium Lyngbya majuscule", Tetrahedron, 2002, vol. 58, Issue: 46, pp. 9445-9458.
Matthew, S., et al., "Cytotoxic Halogenated Macrolides and Modified Peptides from the Apratoxin-Producing Marine Cyanobacterium Lyngbya bouillonii from Guam", Journal of Natural Products, 2010, vol. 73, Issue: 9, pp. 1544-1552.
Hebbes, T.R., et al., "A "minimal epitope" anti-protein antibody that recognises a single modified amino acid", Mol. Immunol., 1989, vol. 26, Issue: 9, pp. 865-873.
Buwitt-Beckmann, U. et al., "Lipopeptide structure determines TLR2 dependent cell activation level," FEBS Journal, 2005, 272: 6354-6364. doi:10.1111/j.1742-4658.2005.05029.x.
Zeng, W. et al., "Structural requirement for the agonist activity of the TLR2 ligand Pam2Cys," Amino Acids, 2010, 39: 471-480.
Wright, T.H. et al., "An improved method for the synthesis of lipopeptide TLR2-agonists using click chemistry," Synlett, 2013, 24, 1835-1841.
Agnihotri, G. et al., "Structure-Activity Relationships in Toll-Like Receptor 2-Agonists Leading to Simplified Monoacyl Lipopeptides," J. Med. Chem., 2011, 54, 8148-8160.
Wittrock, S. et al., "Synthetic Vaccines of Tumor-Associated Glycopeptide Antigens by Immune-Compatible Thioether Linkage to Bovine Serum Albumin," Angew. Chem. Int. Ed., 2007, 46, 5226-5230.
Hoyle, C. E. et al., "Thiol-ene click chemistry," Angewandte Chemie International Edition, 2010, 49(9), 1540-1573.
Campos, L. M. et al., "Development of thermal and photochemical strategies for thiol-ene click polymer functionalization," Macromolecules, 2008, 41(19), 7063-7070.
Lanza,T. et al., "Radical additions of thiols to alkenes and alkynes in ionic liquids," Current Organic Chemistry, 2009, 13(17), 1726-1732.
Lazar, L. et al., "Synthesis of S-linked glycoconjugates and S-disaccharides by thiol-ene coupling reaction of enoses," Organic letters, 2012, 14(17), 4650-4653.
Toth, I. et al., "Recent Advances in Design and Synthesis of Self-Adjuvanting Lipopeptide Vaccines," International Journal of Peptide Research and Therapeutics, 2008, vol. 14 Issue: 4 pp. 333-340.
Zaman, M. et al., "Immunostimulation by synthetic lipopeptide-based vaccine candidates: structure-activity relationships," Front. Immunol. 2013, 4, 318, 1-12.
Isidro-Llobet, A. et al., "Amino acid-protecting groups," Chemical Reviews, 2009, 109(6), 2455-2504.
Lakshminarayanan, V. et al., "Immune recognition of tumor-associated mucin MUC1 is achieved by a fully synthetic aberrantly glycosylated MUC1 tripartite vaccine," Proceedings of the National Academy of Sciences 109, No. 1 (2012): 261-266.
Willems, M. M. et al., "N-tetradecylcarbamyl lipopeptides as novel agonists for Toll-like receptor 2," Journal of medicinal chemistry, 2014, 57(15), 6873-6878.
Burns, M. R. et al., "Polycationic sulfonamides for the sequestration of endotoxin," Journal of medicinal chemistry, 2007, 50(4), 877-888.
Straathof, K.C. et al., "Characterization of Latent Membrane Protein 2 Specificity in CTL Lines from Patients with EBV-Positive Nasopharyngeal Carcinoma and Lymphoma," J. Immunology, 2005, 175, 4137-4147.
Rammensee, H.-G. et al., "SYFPEITHI: database for MHC ligands and peptide motifs," Immunogenetics, 1999, 50, 213-219.
Hanley, P.J., et al., "Functionally active virus-specific T cells that target CMV, adenovirus, and EBV can be expanded from naive

(56) References Cited

OTHER PUBLICATIONS

T-cell populations in cord blood and will target a range of viral epitopes," Blood, 2009 114:1958-1967.
Kessler, J.H. et al., "Efficient Identification of Novel HLA-A*0201—presented Cytotoxic T Lymphocyte Epitopes in the Widely Expressed Tumor Antigen PRAME by Proteasome-mediated Digestion Analysis," J. Exp. Med. 2001 193(1) 73-88. NB: C.Melief Group.
Quintarelli, C. et al., "Cytotoxic T lymphocytes directed to the preferentially expressed antigen of melanoma (PRAME) target chronic myeloid leukemia," Blood, 2008, 112(5):1876. NB: Baylor group, 1876-1885.
Quintarelli, C. et al., "High-avidity cytotoxic T lymphocytes specific for a new PRAME-derived peptide can target leukemic and leukemic-precursor cells," Blood, 2011, 117(12):3353-3362.
Ma W. et al., "Two New Tumor-Specific Antigenic Peptides Encoded by Gene MAGE-C2 and Presented to Cytolytic T Lymphocytes by HLA-A2," Int. J. Cancer, 2004 109:698-702.
Gerdemann, U. et al., "Cytotoxic T Lymphocytes Simultaneously Targeting Multiple Tumor-associated Antigens to Treat EBV Negative Lymphoma," Molecular Therapy, 2011 19(12):2258-68. (NB: original epitope from Ayyoub et al JI 168:1717-22).
Ayyoub, M. et al., "Proteasome-Assisted Identification of a SSX-2-Derived Epitope Recognized by Tumor-Reactive CTL Infiltrating Metastatic Melanoma," Journal of Immunology, 2002, 168:1717-22.
Ayyoub, M. et al., "Tumor-reactive, SSX-2-specific CD8+ T Cells Are Selectively Expanded during Immune Responses to Antigen-expressing Tumors in Melanoma Patients," Cancer Research, 2003, 63(17):5601-6.
Bharadwaj, M. et al., "Contrasting Epstein-Barr virus-specific cytotoxic T cell responses to HLA A2-restricted epitopes in humans and HLA transgenic mice: implications for vaccine design," Vaccine, 2001 19:3769-77.
Duraiswamy, J. et al., "Ex Vivo Analysis of T-Cell Responses to Epstein-Barr Virus-Encoded Oncogene Latent Membrane Protein 1 Reveals Highly Conserved Epitope Sequences in Virus Isolates from Diverse Geographic Regions," Journal of Virology 2003 77(13): 7401-10.
Lee, S.P. et al., "HLA A2.1-Restricted Cytotoxic T Cells Recognizing a Range of Epstein-Barr Virus Isolates through a Defined Epitope in Latent Membrane Protein LMP2," Journal of Virology, 1993, 67(12), 7428-7435.
Liu, G. al., "Immunotherapy of Epstein-Barr Virus Associated Malignancies Using Mycobacterial HSP70 and LMP2A356-364 Epitope Fusion Protein," Cellular & Molecular Immunology, 2009 6(6):423-431.
Liu, G. et al., "Reconstituted complexes of mycobacterial HSP70 and EBV LMP2A-derived peptides elicit peptide-specific cytotoxic T lymphocyte responses and anti-tumor immunity," Vaccine 2011 29 (43):7414-23.
Catalina, M.D. et al., "Differential Evolution and Stability of Epitope-Specific CD8+ T Cell Responses in EBV Infection," The Journal of Immunology, 2001 167:4450-4457.
Fieberger, B.M. et al., "Mature proteins derived from Epstein—Barr virus fail to feed into the MHC class I antigenic pool," European Journal of Immunology, 2012 42:3167-3173.
Demachi-Okamura, A. et al., "Epstein-Barr virus (EBV) latent membrane protein-1-specific cytotoxic T lymphocytes targeting EBV-carrying natural killer cell malignancies," European Journal of Immunology, 2006 36:593-602.
Meij, P. et al., "Identification and Prevalence of CD8+ T-Cell Responses Directed Against Epstein-Barr Virus-Encoded Latent Membrane Protein 1 and Latent Membrane Protein 2," Int. J. Cancer, 2002 99:93-99.
Metzger, J. W. et al., "Synthesis of Nα-Fmoc protected derivatives of S-(2, 3-dihydroxypropyl)-cysteine and their application in peptide synthesis," Int. J. Peptide Protein Res. 38(6), 1991, 545-554.

Salunke, D. B. et al., "Design and development of stable, water-soluble, human Toll-like receptor 2 specific monoacyl lipopeptides as candidate vaccine adjuvants," Journal of Medicinal Chemistry, 2013, 56(14), 5885-5900.
Melief, C.J.M., "Cancer immunotherapy by dendritic cells," Immunity, 2008, 29(3), 372-383.
Couzin-Frankel, J., "Cancer Immunotheraphy," Science, 2013, 342, 1432-1433.
Pardoll, D. M., "The blockade of immune checkpoints in cancer immunotherapy," Nature Reviews Cancer, 2012, 12(4), 252-264.
Robert, C. et. al., "Ipilimumab plus dacarbazine for previously untreated metastatic melanoma," New England Journal of Medicine, 2011, 364(26), 2517-2526.
Banchereau, J. et al., "Dendritic cells as vectors for therapy," Cell, 2001, 106(3), 271-274.
Thara, E. et al., (2011). "Vaccine therapy with sipuleucel-T (Provenge) for prostate cancer," Maturitas, 2011, 69(4), 296-303.
Kenter, G. G. et al., "Vaccination against HPV-16 Oncoproteins for Vulvar Intraepithelial Neoplasia," J. Med., 2009, 361, 1838-1847.
Cheever, M. A. et al., "The Prioritization of Cancer Antigens: A National Cancer Institute Pilot Project for the Acceleration of Translational Research," Clin. Cancer Res., 2009, 15, 5323-5337.
Van Der Burg, S. H. et al., "Therapeutic vaccination against human papilloma virus induced malignancies," Curr. Opin. Immunol., 2011, 23, 252-257.
Akira, S. et al., "Pathogen Recognition and Innate Immunity," Cell, 2006, 124, 783-801.
Banchereau, J. et al., Immunobiology of Dendritic Cells. Annu. Rev. Immunol., 2000, 18, 767-811.
Anderson, K. V. et al., "Establishment of Dorsal-Ventral Polarity in the *Drosophila* Embryo: Genetic Studies on the Role of the Toll Gene Product," Cell, 1985, 42, 779-789.
Kawai, T. et al., "The role of pattern-recognition receptors in innate immunity: update on Toll-like receptors.,". Nat. Immunol., 2010, 11, 373-384.
Jin, M. S. et al., "Structures of TLR—ligand complexes," Curr. Opin. Immunol., 2008, 20, 414-419.
Gay, N. J. et al., "Structure and Function of Toll Receptors and Their Ligands," Ann. Rev. Biochem., 2007, 76, 141-165.
Bryant, C. E. et al., "The molecular basis of the host response to lipopolysaccharide," Nat. Rev. Microbiol., 2010, 8, 8-14.
Duthie, M. S. et al., "Use of defined TLR ligands as adjuvants within human vaccines," Immunol. Rev., 2011, 239, 178-196.
Ingale, S. et al., "Robust immune responses elicited by a fully synthetic three-component vaccine," Nat. Chem. Biol., 2007, 3, 663-667.
Lake, R. A. et al., "Immunotherapy and chemotherapy—a practical partnership," Nat. Rev. Cancer, 2005, 5, 397-405.
Li, F. et al., "A Direct Method for Site-Specific Protein Acetylation," Angew. Chem. Int. Ed. 2011, 50, 9611-9614.
Takeuchi, O. et al., "Cutting Edge: Preferentially the R-stereoisomer of the Mycoplasmal Lipopeptide Macrophage-Activating Lipopeptide-2 Activates Immune Cells Through a Toll-Like Receptor 2- and MyD88-Dependent Signaling Pathway," J. Immunology, 2000, 164, 554-557.
Kahn, S. et al., "Chirality of TLR-2 ligand Pam3CysSK4 in fully synthetic peptide conjugates critically influences the induction of specific CD8+ T-cells," Molecular Immunology, 2009, 46, 1084-1091.
Tokunaga, M. et al., "Asymmetric Catalysis with Water. Efficient Kinetic Resolution of Terminal Epoxides by Means of Catalytic Hydrolysis," Science, 1997, 277, 936-939.
Schaus, S. E. et al., "Highly Selective Hydrolytic Kinetic Resolution of Terminal Epoxides Catalyzed by Chiral (salen) CoIII Complexes. Practical Synthesis of Enantioenriched Terminal Epoxides and 1,2-Diols," J. Am. Chem. Soc., 2002, 124, 1307-1315.
Wu, W. et al., "Structure-Activity Relationships in Toll-like Receptor-2 Agonistic Diacylthioglycerol Lipopeptides," J. Med. Chem. 2010, 53, 3198-3213.
Wick, M. J. et al., "Major histocompatibility complex class I presentation of ovalbumin peptide 257-264 from exogenous sources: protein context influences the degree of TAP-independent presentation," Eur. J. Immunol., 1996, 26, 2790-2799.

(56) References Cited

OTHER PUBLICATIONS

Robertson, J. M. et al., "DO11.10 and OT-II T Cells Recognize a C-Terminal Ovalbumin 323-339 Epitope," J. Immunol., 2000, 164, 4706-4712.
Boyer, C. et al., "Synthesis of a New Macromonomer from 2-(Dimethylamino)ethyl Methacrylate Bearing 1-(Isopropenylphenyl)-1,1-dimethylmethyl Isocyanate Group," Macromol. Chem. Phys., 2004, 205, 645-655.
Bertrais, H. et al., "Synthese De Telomeres Photoreticulables A Partir Du Cinnamate Et De L'acetate De Vinyle," Eur. Polym. J., 1982, 18, 779-784.
Cadierno, V. et al., "Ruthenium(IV)-Catalyzed Markovnikov Addition of Carboxylic Acids to Terminal Alkynes in Medium," Organometallics, 2011, 30, 852-862.
Wei, S. et al., "Development of an Improved Rhodium Catalyst for Z-Selective Anti-Markovnikov Addition of Carboxylic Acids to Terminal Alkynes," Chem. Eur. J., 2013, 19, 12067-12076.
Reppe, W. et al., Justus Liebigs Annalen der Chemie, 1956, 601, 81-138.
Tsukada, N. et al., "Hydrocarboxylation of unactivated internal alkynes with carboxylic acids catalyzed by dinuclear palladium complexes," Tetrahedron Lett. 2011, 52, 248-250.
Rotem, M. et al., "Addition of carboxylic acids to alkynes catalysed by ruthenium complexes," J. Organometallic Chem. 1993, 448, 159-204.
Karmee, S.K., "A Two Step Chemo-Enzymatic Method for the Synthesis of Fatty Acid Ascorbyl Esters," J. Oil Palm Res., 2012, 1518-1523.
Foster, D.J. et al., "Organomercury Chemistry. A Novel Synthesis of Vinyl Esters, Vinyl Ethers and Vinyl Thioethers," J. Am. Chem. Soc., 1961, 83, 851-855.
Luo, F. et al., "Copper(II)-Catalyzed Esterification of Arenecarboxylic Acids with Aryl- and Vinyl-Substituted Trimethoxysilanes," Synthesis, 2010, 2005-2010.
Nakamura, A. et al., "Au(I) complexes-catalyzed transfer vinylation of alcohols and carboxylic acids," Tetrahedron Lett., 2008, 49, 3729-3732.
Nakagawa, H. et al., "Synthesis of enol and vinyl esters catalyzed by an iridium complex," Tetrahedron Lett. 2003, 44, 103-106.
Rokhum, L. et al., "A practical one-pot synthesis of azides directly from alcohols," J. Chem. Sci., 2012, 124, 687-691.
Cui, H.K. et al., "Diaminodiacid-Based Solid-Phase Synthesis of Peptide Disulfide Bond Mimics," Angew. Chemie. Int. Eng. 2013, 52, 36, 9558-9562.

Rodriguez, A. R. et al. "First total synthesis of pro-resolving and tissue-regenerative Maresin sulfido-conjugates," Tetrahedron Letters, (2015) 56(25), 3936-3940.
Wang, C. et al., "Tungsten-Catalyzed Asymmetric Epoxidation of Allylic and Homoallylic Alcohols with Hydrogen Peroxide," J. Am. Chem. Soc. 2014, 136, 1222-1226.
Volkmann, R.A. et al., "2-Thioalkyl Penems: An Efficient Synthesis of Sulopenem, a (5R, 6S)-6-(1(R)-Hydroxyethyl)-2-[(cis-1-oxo-3-thiolanyl)thio]-2-penem Antibacterial," J. Org. Chem. 1992, 57, 4352-4361.
Yang, S.-H. et al., "Lipidation of Cysteine or Cysteine-Containing Peptides Using the Thiol-Ene Reaction (CLipPA)," Eur. J. Org. Chem., (2016) 2608-2616.
Hamley I.W., "Lipopeptides: from self-assembly to bioactivity," Chemical Communications, 2015, 51, 41, 8574-8583.
Takeuchi, O. et al., "Cutting Edge: Role of Toll-Like Receptor 1 in Mediating Immune Response to Microbial Lipoproteins," J. Immunol. 2002, 169, 10-14.
Asai, Y. et al. "Toll-like receptor 2-mediated dendritic cell activation by a Porphyromonas gingivalis synthetic lipopeptide," Journal of medical microbiology, (2007) 56(4), 459-465.
Makimura, Y. et al., "Correlation between chemical structure and biological activities of Porphyromonas gingivalis synthetic lipopeptide derivatives," Clinical & Experimental Immunology, (2006) 146(1), 159-168.
Omueti, K.O. et al., "Domain Exchange between Human Toll-like Receptors 1 and 6 Reveals a Region Required for Lipopeptide Discrimination," J. Biol. Chem. 2005, 280, 36616-36625.
Schulze, O. et al., "The thio-Mitsunobu reaction: a useful tool for the preparation of 2,5-anhydro-2-thio- and 3,5-anhydro-3-thiopentofuranosides," Carbohydr Res. 2004, 338, 1787-1802.
Reddy, C.R. et al., "Synthesis of the methylene bis-tetrahydropyran motif of (-)-exiguolide," Tetrahedron Lett. 2010, 51, 44, 5840-5842.
Sauret-Cladiere, Sauret-Cladiere et al., Synthesis of (+)-2,8-dihydroxyethyl-l,4,7,10- tetraoxaspiro[5.5]undecane from (R)-4-hydroxymethyl-2,2-dimethyl-1,3-dioxane. Tetrahedron Asymmetry, 1997, 8, 3, 417-423.
Spohn, R. et al., "Synthetic lipopeptide adjuvants and Toll-like receptor 2-structure-activity relationships," Vaccine, 2004, 22, 2494-2499.
Rasmussen, M. et al., "Describing the Peptide Binding Specificity of HLA-C (106.41)," J. Immunol., May 1, 2012, 188 (1 Supplement) 106.41; 1.
Japanese Patent Office, Examination Report—Notice of Reasons for Rejection, Patent Application No. 2016-522936, dated Jul. 10, 2018, pp. 1-7.

* cited by examiner

AMINO ACID AND PEPTIDE CONJUGATES AND USES THEREOF

This application is a continuation application of U.S. patent application Ser. No. 15/535,956, filed Jun. 14, 2017, which is a § 371 application of PCT/IB2015/059901, filed Dec. 22, 2015, which in turn claims priority to U.S. Provisional Application No. 62/096,106, filed Dec. 23, 2014. The entire disclosure of each of the foregoing applications is incorporated by reference herein.

Incorporated herein by reference in its entirety is the Sequence Listing being concurrently submitted via EFS-Web as a text file named SeqList.txt, created Jan. 16, 2019, and having a size of 60,450 bytes.

TECHNICAL FIELD

The present invention relates to amino acid and peptide conjugates, methods for making amino acid and peptide conjugates, conjugates produced by the methods, pharmaceutical compositions comprising the peptides and conjugates, methods of eliciting immune responses in a subject and methods of vaccinating a subject, uses of the peptides and conjugates for the same, and uses of the peptides and conjugates in the manufacture of medicaments for the same.

BACKGROUND ART

Synthetic peptide vaccines generally comprise a synthetic copy of an immunogenic part of protein antigens. This approach to vaccine development has a number of advantages, including ease of synthesis, avoidance of potentially toxic biological by-products and straightforward characterisation.

A key issue in the development of peptide vaccines is the lack of immunogenicity displayed by peptides as sole vaccine components. It is usually necessary to include in the vaccine an adjuvant, designed to activate components of the innate immune system (e.g. Freund's adjuvant).

An alternative strategy in peptide vaccine design is to create self-adjuvanting vaccines in which the peptide epitope of interest is covalently linked to an appropriate adjuvant.

Such self-adjuvanting vaccines may have enhanced antigen uptake, presentation and dendritic cell maturation compared to simple co-formulation of the antigen with an external adjuvant.

Several self-adjuvanting vaccines have been developed, but preparation of the vaccines can be complicated.

There is an ongoing need for new self-adjuvanting vaccines and new methods of making self-adjuvanting vaccines. In particular, there is a need for self-adjuvanting vaccines directed to treating Epstein Barr Virus (EBV) associated diseases, such as Hodgkin's Disease (HD) or Nasopharangeal Carcinoma (NPC), including, for example, self-adjuvating vaccines comprising one or more epitopes from EBV Latent Membrane Protein 2 (LMP2).

It is an object of the present invention to go some way towards meeting these needs; and/or to at least provide the public with a useful choice.

Other objects of the invention may become apparent from the following description which is given by way of example only.

Any discussion of documents, acts, materials, devices, articles or the like which has been included in the present specification is solely for the purpose of providing a context for the present invention. It is not to be taken as an admission that any or all of these matters form part of the prior art base or are common general knowledge in the field relevant to the present invention as it existed before the priority date.

SUMMARY OF THE INVENTION

In one aspect, the present invention provides a method for making a peptide conjugate, the method comprising
providing a lipididated amino acid or peptide, and
coupling the lipidated amino acid or peptide to one or more amino acids or peptides to provide a peptide conjugate, and wherein the peptide conjugate comprises one or more EBV LMP2 epitopes.

In one aspect, the present invention provides a method for making a peptide conjugate, the method comprising reacting
a lipid-containing conjugation partner, and
an amino acid-comprising conjugation partner,
under conditions effective to conjugate the lipid-containing conjugation partner to the amino acid-comprising conjugation partner by the hydrothiolation of a carbon-carbon double bond with a thiol,
the method further comprising coupling the amino acid of the amino acid conjugate to an amino acid or a peptide to provide a peptide conjugate, and wherein the peptide conjugate comprises one or more EBV LMP2 epitopes.

In another aspect, the present invention provides a method for making a peptide conjugate, the method comprising reacting
a lipid-containing conjugation partner, and
a peptide-comprising conjugation partner, wherein the peptide-comprising partner comprises one or more EBV LMP2 epitopes,
under conditions effective to conjugate the lipid-containing conjugation partner to the peptide-comprising conjugation partner by the hydrothiolation of a carbon-carbon double bond with a thiol.

In another aspect, the present invention provides an amino acid conjugate or peptide conjugate as herein described. In various embodiments, the amino acid conjugate or peptide conjugate comprises one or more EBV LMP2 epitopes. In one example, the amino acid conjugate or peptide conjugate is an amino acid conjugate or peptide conjugate made by a method of the present invention.

In one embodiment, the present invention provides a peptide conjugate comprising one or more EBV LMP2 epitopes. In various embodiments, the one or more EBV LMP2 epitopes are MHCI epitopes. In various embodiments, the peptide conjugate comprises one or more EBV LMP2 epitopes selected from the group consisting of any one of SEQ ID NOs 76-101. In various embodiments, the peptide conjugate comprises a peptide comprising or consisting of 12 or more contiguous amino acids from the amino acid sequence of any one of SEQ ID NOs 1-75. In various embodiments, the the peptide conjugate comprises a peptide comprising or consisting of 15 or more contiguous amino acids from the amino acid sequence of any one of SEQ ID NOs 1-75, or comprising or consisting of 20 or more contiguous amino acids from the amino acid sequence of any one of SEQ ID NOs 1-75.

In another aspect, the present invention provides an isolated, purified, or recombinant peptide comprising or consisting of 12 or more contiguous amino acids from the amino acid sequence of any one of SEQ ID NOs 1-75. In various embodiments, the isolated, purified, or recombinant peptide comprises or consists of 15 or more contiguous amino acids from the amino acid sequence of any one of SEQ ID NOs 1-75, or comprises or consists of 20 or more contiguous amino acids from the amino acid sequence of any one of SEQ ID NOs 1-75.

In one embodiment, the peptide comprises, consists of, or consists essentially of an amino acid sequence selected from the group consisting of any one of SEQ ID NOs 1-75.

Any of the embodiments described herein relate to any of the aspects herein.

In various embodiments, the lipidated amino acid or peptide comprises one or more of the following: Pam1Cys, Pam2Cys, and Pam3Cys. For example, the lipidated amino acid or peptide comprises one or more of the following: Pam1CSK$_4$, Pam2 CSK$_4$, and Pam3 CSK$_4$. In various embodiments, the lipidated amino acid or peptide is acetylated or amidated, for example, the lipidated amino acid or peptide comprises acetylated Pam1Cys, acetylated Pam2Cys, or acetylated Pam3Cys, or amidated Pam1Cys, amidated Pam2Cys, or amidated Pam3Cys.

In one embodiment, the amino acid-comprising conjuation partner is a peptide-containing conjugation partner, and the lipid-containing conjugation partner is coupled to the peptide of the peptide-containing conjugation partner.

In some embodiments, the lipid-containing conjugation partner is conjugated to the or an amino acid of the amino acid-containing conjugation partner or the peptide of the peptide-containing conjugation partner.

In certain embodiments, the lipid-containing conjugation partner is conjugated to the or an amino acid of the amino acid-containing conjugation partner.

Accordingly, in another aspect, the present invention provides a method for making a peptide conjugate, the method comprising reacting
  a lipid-containing conjugation partner, and
  a peptide-containing conjugation partner, wherein the peptide-comprising partner
  comprises one or more EBV LMP2 epitopes,
    under conditions effective to conjugate the lipid-containing conjugation partner to the peptide of the peptide-containing conjugation partner by the hydrothiolation of a carbon-carbon double bond with a thiol.

In one embodiment, the conjugate is a lipopeptide, such that the method is for making a lipopeptide.

In one embodiment, the lipid-containing conjugation partner comprises the carbon-carbon double bond, and the peptide of the peptide-containing conjugation partner comprises the thiol.

In one embodiment, the amino acid-comprising conjuation partner comprises one or more EBV LMP2 epitopes. In one embodiment, the peptide-containing conjugation partner comprises one or more EBV LMP2 epitopes. In one embodiment, the amino acid-comprising conjugation partner comprises two or more EBV LMP2 epitopes. In one embodiment, the peptide-containing conjugation partner comprises two or more EBV LMP2 epitopes. In one embodiment, the peptide conjugate comprises two or more EBV LMP2 epitopes. In one embodiment, the epitope is a peptide epitope. In one embodiment, the amino acid-comprising conjugation partner consists of a peptide. In one embodiment, the amino acid-comprising conjugation partner consists of a peptide comprising a peptide epitope. In one embodiment, the peptide-containing conjugation partner consists of a peptide. In one embodiment, the peptide-containing conjugation partner consists of a peptide comprising a peptide epitope.

In some embodiments, the amino acid-comprising conjugation partner comprises an epitope bound to the or an amino acid of the conjugation partner. In some embodiments, the peptide-containing conjugation partner comprises an epitope bound to the peptide of the peptide-containing conjugation partner. In some embodiments, the epitope is bound to the peptide via linker group.

In some embodiments, the amino acid-comprising conjugation partner comprises a peptide epitope bound to the or an amino acid of the conjugation partner via a linker group. In some embodiments, the peptide-containing conjugation partner comprises a peptide epitope bound to the peptide via a linker group.

In some embodiments, the amino acid-comprising conjugation partner and/or the peptide-containing conjugation partner comprises an antigenic peptide. In some embodiments, the peptide conjugate comprises an antigenic peptide.

In some embodiments, the method further comprises coupling the amino acid of the amino acid conjugate to an amino acid or a peptide to provide a peptide conjugate, wherein the peptide conjugate comprises one or more EBV LMP2 epitopes.

In some embodiments, coupling a peptide comprises individually coupling one or more amino acids and/or one or more peptides.

In some embodiments, the method further comprises coupling the amino acid of the amino acid conjugate or an amino acid of the peptide conjugate to an amino acid or a peptide so as to provide a peptide conjugate comprising a linker group or one or more amino acids thereof.

In some embodiments, the method further comprises coupling an amino acid of the peptide conjugate comprising a linker group or one or more amino acids thereof to an amino acid or a peptide so as to provide a peptide conjugate comprising one or more EBV LMP2 epitopes bound to the amino acid to which lipid-containing conjugation partner is conjugated via a linker group.

In some embodiments, the amino acid of the peptide conjugate to which the lipid-containing conjugate is conjugated is an N-terminal amino acid residue.

In some embodiments, the method further comprises coupling the amino acid of the amino acid conjugate or an amino acid of the peptide conjugate to an amino acid or a peptide so as to provide a peptide conjugate comprising one or more EBV LMP2 epitopes.

In some embodiments, the method further comprises coupling one or more EBV LMP2 epitopes to the amino acid of the amino acid conjugate or an amino acid of the peptide conjugate. In some embodiments, the method further comprises coupling one or more EBV LMP2 epitopes to the amino acid of the amino acid conjugate or an amino acid of the peptide conjugate. In some embodiments, the epitope is coupled or bound via a linker group.

In some embodiments, the method further comprises coupling an epitope to the peptide of the peptide conjugate. In some embodiments, the method further comprises coupling a peptide epitope to the peptide of the peptide conjugate. In some embodiments, the epitope is bound to the peptide via a linker group. In various examples, the epitope is a EBV LMP2 epitope.

In one embodiment, the amino acid-comprising conjugation partner consists of an amino acid. In one embodiment, the carboxyl group of the C-terminus of the amino acid is protected with a carboxyl protecting group and/or the Nα-amino group of the amino acid is protected with an amino protecting group.

In some embodiments, the carboxyl group of the C-terminus of the peptide is protected with a carboxyl protecting group and/or the Nα-amino group of the peptide is protected with an amino protecting group.

In one embodiment, the lipid-containing conjugation partner comprises one or more optionally substituted straight or branched aliphatic or heteroaliphatic chains each containing at least 4 chain-linked atoms. In one embodiment, the lipid-containing conjugation partner comprises one or more optionally substituted straight or branched aliphatic or heteroaliphatic chains each containing at least 6 chain-linked atoms. In one specifically contemplated embodiment, the one or more chains are aliphatic. In one specifically contemplated embodiment, the one or more chains are saturated.

In some embodiments, the one or more chains are optionally substituted. In some embodiments, the one or more chains are optionally substituted with one or more aryl groups.

In some embodiments, the one or more chains comprise at least 4, 6, 8, 10, 12, or 14 chain-linked atoms. In some embodiments, the one or more chains comprise from 4-22, 6-22, 8-22, 10-22, 12-22, or 14-22 chain-linked atoms.

In one embodiment, the one or more chains are covalently bound to a moiety comprising the carbon-carbon double bond or the thiol by a heteroatom-containing functional group. Examples of heteroatom-containing functional groups include but are not limited to ether, amine, sulfide, sulfoxide, sulfone, ester, amide, carbonate, carbamate, and urea groups.

In exemplary embodiments, the one or more chains are covalently bound to the moiety by ester functional groups.

In one embodiment, the lipid-containing conjugation partner comprises one or more saturated or unsaturated fatty acid esters. In some embodiments, the fatty acid is saturated. In one embodiment, one or more fatty acid ester is bound to the moiety comprising to carbon-carbon double bond or thiol. In one embodiment, the ester is an ester of the carboxyl group of the fatty acid and an alcohol of the moiety.

In one embodiment, the fatty acid is a C4-22 fatty acid. In one embodiment, the fatty acid is a C6-22 fatty acid. In another embodiment, the fatty acid is a C10-22 fatty acid. In yet another embodiment, the fatty acid is a C12-22 fatty acid. In one exemplary embodiment, the fatty acid is a C12, C14, C16, C18, or C20 fatty acid.

In some embodiments, the fatty acid is lauric acid, myristic acid, palmitic acid, stearic acid, arachic acid, palmitoleic acid, oleic acid, elaidic acid, linoleic acid, α-linolenic acid, and arachidonic acid. In one embodiment, the fatty acid is lauric acid, myristic acid, palmitic acid, or stearic acid. In a specifically contemplated embodiment, the fatty acid is palmitic acid.

In one exemplary embodiment, the lipid-containing conjugation partner comprises one or two fatty acid esters. In a specifically contemplated embodiment, the lipid-containing conjugation partner comprises one fatty acid ester.

In certain embodiments, the fatty acid ester is an ester of an alcohol comprising the carbon-carbon double bond or thiol. In one embodiment, the alcohol is a monohydric, dihydric, or trihydric C2-6 aliphatic alcohol. In another embodiment, the alcohol is a monohydric or dihydric C2-4 aliphatic alcohol. In one exemplary embodiment, the alcohol is a monohydric C2 aliphatic or monohydric or dihydric C3 aliphatic alcohol. In a specifically contemplated embodiment, the alcohol is a monohydric C2 alcohol.

In certain embodiments, the lipid-containing conjugation partner comprises the carbon-carbon double bond.

In one exemplary embodiment, the alcohol comprises the carbon-carbon double bond.

In a specifically contemplated embodiment, the alcohol is vinyl alcohol.

In specifically contemplated embodiments, the peptide is a synthetic peptide.

In one embodiment, the amino acid-comprising conjugation partner and/or peptide conjugate comprises a synthetic peptide. In some embodiments, the synthetic peptide is a peptide prepared by a method comprising solid phase peptide synthesis (SPPS).

In some embodiments, the or an amino acid of the amino acid-comprising conjugation partner comprises the carbon-carbon double bond or thiol. In some embodiments, an amino acid residue of the peptide of the peptide-containing conjugation partner comprises the carbon-carbon double bond or thiol.

In some embodiments, the amino acid residue comprising the carbon-carbon double bond or thiol is a terminal amino acid residue. In some embodiments, the terminal amino acid residue is an N-terminal residue.

In some embodiments, the Nα-amino group of the amino acid comprising the carbon-carbon double bond or thiol is acylated.

In certain embodiments, the method further comprises acylating the Nα-amino group of the amino acid of the amino acid conjugate or the amino acid residue of the peptide conjugate to which the lipid-containing conjugation partner is conjugated. In certain embodiments, the method further comprises acylating the Nα-amino group with a C2-20 fatty acid.

In certain embodiments, the or an amino acid of the amino acid-comprising conjugation partner comprises the thiol. In certain embodiments, an amino acid residue of the peptide of the peptide-containing conjugation partner comprises the thiol. In certain embodiments, the thiol is the thiol of a cysteine residue.

In certain embodiments, the cysteine residue is a terminal residue. In certain embodiments, the cysteine residue is an N-terminal residue.

In some embodiments, the amino group of the cysteine residue is acylated.

In one embodiment, the amino group is acylated with a C2-20 fatty acid.

In one exemplary embodiment, the C2-20 fatty acid is acetyl or palmitoyl. In another exemplary embodiment, the C2-20 fatty acid is acetyl.

In some embodiments, the amino acid-comprising conjugation partner and/or peptide conjugate comprises from 8 to 220, 8 to 200, 8 to 175, 8 to 150, 8 to 125, 8 to 100, 8 to 90, 8 to 80, 8 to 70, 8 to 60, 8 to 50, 8 to 40, 8 to 30, 8 to 25, 8 to 20, or 8 to 15 amino acids. In some embodiments, the peptide-containing conjugation partner comprises from 8 to 220, 8 to 200, 8 to 175, 8 to 150, 8 to 125, 8 to 100, 8 to 90, 8 to 80, 8 to 70, 8 to 60, 8 to 50, 8 to 40, 8 to 30, 8 to 25, 8 to 20, or 8 to 15 amino acids.

In one exemplary embodiment, the amino acid-comprising conjugation partner and/or peptide conjugate comprises a peptide comprising from 8 to 60 amino acids. In one exemplary embodiment, the peptide comprises from 8 to 60 amino acids.

In other embodiments, the amino acid-comprising conjugation partner and/or peptide conjugate comprises from 5 to 220, 8 to 220, 5 to 175, 8 to 175, 8 to 150, 10 to 150, 15 to 125, 20 to 100, 20 to 80, 20 to 60, 25 to 100, 25 to 80, 25 to 60, 30 to 80, 40 to 60, or 50 to 60 amino acids. In other embodiments, the peptide-containing conjugation partner comprises from 5 to 220, 8 to 220, 5 to 175, 8 to 175, 8 to 150, 10 to 150, 15 to 125, 20 to 100, 20 to 80, 20 to 60, 25 to 100, 25 to 80, 25 to 60, 30 to 80, 40 to 60, or 50 to 60 amino acids.

In other embodiments, the amino acid-comprising conjugation partner and/or peptide conjugate comprises from 5 to 150, 5 to 125, 5 to 100, 5 to 75, 5 to 60, 5 to 50, 5 to 40, 5 to 30, 5 to 25, 5 to 20, 8 to 150, 8 to 125, 8 to 100, 8 to 75, 8 to 60, 8 to 50, 8 to 40, 8 to 30, 8 to 25, or 8 to 20 amino acids. In other embodiments, the peptide-containing conjugation partner comprises from 5 to 150, 5 to 125, 5 to 100, 5 to 75, 5 to 60, 5 to 50, 5 to 40, 5 to 30, 5 to 25, 5 to 20, 8 to 150, 8 to 125, 8 to 100, 8 to 75, 8 to 60, 8 to 50, 8 to 40, 8 to 30, 8 to 25, or 8 to 20 amino acids.

In one embodiment, the amino acid-comprising conjugation partner and/or peptide conjugate comprises one or more solubilising groups. In one embodiment, the peptide-containing conjugation partner comprises one or more solubilising groups.

In certain embodiments, the solubilising group is an amino acid sequence comprising two or more hydrophilic amino acid residues in the peptide chain. In certain embodiments, the solubilising group is an amino acid sequence comprising a sequence of two or more consecutive hydrophilic amino acid residues in the peptide chain. In one embodiment, the hydrophilic amino acid residues are cationic amino acid residues. In one embodiment, the cationic amino acid residues are arginine or lysine residues. In one specifically contemplated embodiment, the cationic amino acid residues are lysine residues. In one embodiment, the sequence comprises from 2 to 20, 2 to 15, 2 to 10, 3 to 7, or 3 to 5 amino acids. In one embodiment, the solubilising group is a tri-, tetra-, penta-, hexa-, or hepta-lysine sequence. In one specifically contemplated embodiment, the solubilising group is a tetralysine sequence.

In some embodiments, the peptide conjugate and/or amino-acid comprising conjugation partner comprises a serine residue adjacent to the amino acid residue to which the lipid-containing conjugation partner is conjugated. In a specifically contemplated embodiment, the peptide of the peptide-containing conjugation partner comprises a serine residue adjacent to the amino acid residue to which the lipid-containing conjugation partner is conjugated. In an exemplary embodiment, the amino acid residue to which the lipid-containing conjugation partner is conjugated is N-terminal. In a specifically contemplated embodiment, the peptide further comprises a consecutive sequence of two or more hydrophilic amino acid residues adjacent to the serine residue.

In certain embodiments, the peptide conjugate and/or amino-acid comprising conjugation partner comprises a consecutive sequence of two or more hydrophilic amino acid residues adjacent to the serine residue.

In certain embodiments, the peptide conjugate and/or amino acid-comprising conjugation partner comprises only naturally occurring amino acids. In certain embodiments, the peptide-containing conjugation partner comprises only naturally occurring amino acids. In other embodiments, 75% or more, 80% or more, 85% or more, 90% or more, 95% or more, 97% or more, or 99% or more of the amino acid residues in the peptide are naturally occurring amino acids.

In other embodiments, 75% or more, 80% or more, 85% or more, 90% or more, 95% or more, 97% or more, or 99% or more of the amino acid residues in the peptide conjugate and/or amino acid-comprising conjugation partner are naturally occurring amino acids.

In exemplary embodiments, the peptide conjugate and/or amino acid-comprising conjugation partner comprises a peptide comprising an EBV LMP2 epitope. In exemplary embodiments, the peptide of the peptide-containing conjugation partner comprises one or more EBV LMP2 epitopes.

In various embodiments, the peptide comprises, consists of, or consists essentially of an amino acid sequence selected from the group consisting of (a) 8 or more contiguous amino acid residues from the sequence $Xaa_1Xaa_2Xaa_3Xaa_4$DRHSDYQPLGTQDQSLYL GLQHDGNDGL [SEQ ID NO: 1], wherein $Xaa_1$ is absent or is S or a hydrophilic amino acid, $Xaa_2$ is absent or is a hydrophilic amino acid, $Xaa_3$ is absent or is a hydrophilic amino acid, and $Xaa_4$ is absent or is one or more hydrophilic amino acids, (b) 8 or more contiguous amino acid residues from the sequence $Xaa_1Xaa_2Xaa_3$DRHSDYQPLGTQDQSLYLGLQH DGNDGL [SEQ ID NO:2], wherein Xaa1 is absent or is S or a hydrophilic amino acid, $Xaa_2$ is absent or is a hydrophilic amino acid, and $Xaa_3$ is absent or is from one to ten hydrophilic amino acids, (c) 8 or more contiguous amino acid residues from the sequence $Xaa_1Xaa_2$DRHSDYQPLGTQDQSLYLGLQHDGNDGL [SEQ ID NO:3], wherein Xaa1 is absent or is S or a hydrophilic amino acid, and $Xaa_2$ is absent or is from one to four hydrophilic amino acids, (d) 8 or more contiguous amino acid residues from the sequence SKKKKDRHSDYQPLGTQDQS-LYLGLQHDGNDGL [SEQ ID NO:4], (e) 8 or more contiguous amino acid residues from the sequence DRHSDYQPLGTQDQSLYLGLQHDGNDGL [SEQ ID NO:5], (f) 8 or more contiguous amino acid residues from the sequence $Xaa_1Xaa_2Xaa_3Xaa_4$SLYLGLQHDGNDGLPPPP YSPRDDSSQHIYEEA [SEQ ID NO:6], wherein $Xaa_1$ is absent or is S or a hydrophilic amino acid, $Xaa_2$ is absent or is a hydrophilic amino acid, $Xaa_3$ is absent or is a hydrophilic amino acid, and $Xaa_4$ is absent or is one or more hydrophilic amino acids, (g) 8 or more contiguous amino acid residues from the sequence $Xaa_1Xaa_2Xaa_3$SLYLGLQHDGNDGLPPPPYSPRD DSSQHIYEEA [SEQ ID NO:7], wherein $Xaa_1$ is absent or is S or a hydrophilic amino acid, $Xaa_2$ is absent or is a hydrophilic amino acid, and $Xaa_3$ is absent or is from one to ten hydrophilic amino acids, (h) 8 or more contiguous amino acid residues from the sequence $Xaa_1Xaa_2$SLYLGLQHDGNDGLPPPPYSPRDDSS QHIYEEA [SEQ ID NO:8], wherein $Xaa_1$ is absent or is S or a hydrophilic amino acid, and $Xaa_2$ is absent or is from one to four hydrophilic amino acids, (i) 8 or more contiguous amino acid residues from the sequence SKKKKSLYLGLQHDGNDGLPPP-PYSPRDDSSQHIYEEA [SEQ ID NO:9], (j) 8 or more contiguous amino acid residues from the sequence SLYLGLQHDGNDGLPPP-PYSPRDDSSQHIYEEA [SEQ ID NO: 10], (k) 8 or more contiguous amino acid residues from the sequence $Xaa_1Xaa_2Xaa_3Xaa_4$SDYQPLGTQDQSLYLGLQH DGNDGL [SEQ ID NO:11], wherein $Xaa_1$ is absent or is S or a hydrophilic amino acid, $Xaa_2$ is absent or is a hydrophilic amino acid, $Xaa_3$ is absent or is a hydrophilic amino acid, and $Xaa_4$ is absent or is one or more hydrophilic amino acids, (l) 8 or more contiguous amino acid residues from the sequence Xaa$_1$Xaa$_2$Xaa$_3$SDYQPLGTQDQSLYLGLQHDGNDGL [SEQ ID NO: 12], wherein Xaa$_1$ is absent or is S or a hydrophilic amino acid, Xaa$_2$ is absent or is a hydrophilic amino acid, and Xaa$_3$ is absent or is from one to ten hydrophilic amino acids, (m) 8 or more contiguous amino acid residues from the sequence Xaa$_1$Xaa$_2$SDYQPLGTQDQSLYLGLQ HDGNDGL [SEQ ID NO: 13], wherein Xaa$_1$ is absent or is S or a hydrophilic amino acid, and Xaa$_2$ is absent or is from one to four hydrophilic amino acids, (n) 8 or more contiguous amino acid residues from the sequence SKKKKSDYQPLGTQDQSLYLGLQHDGNDGL [SEQ ID NO: 14], (o) 8 or more contiguous amino acid residues from the sequence SDYQPLGTQDQSLYLGLQHDGNDGL [SEQ ID NO: 15], (p) 8 or more contiguous amino acid residues from the sequence Xaa$_1$Xaa$_2$Xaa$_3$Xaa$_4$DRHSDYQ PLGTQDQS-LYLGLQHDGNDGLPPPPYSPRDDSSQHIYEEA [SEQ ID NO:16], wherein Xaa$_1$ is absent or is S or a hydrophilic amino acid, Xaa$_2$ is absent or is a hydrophilic amino acid, Xaa$_3$ is absent or is a hydrophilic amino acid, and Xaa$_4$ is absent or is one or more hydrophilic amino acids, (q) 8 or more contiguous amino acid residues from the sequence Xaa$_1$Xaa$_2$Xaa$_3$DRHSDYQPLGTQDQSLY LGLQHDGNDGLPPPPYSPRDDSSQHIYEEA [SEQ ID NO:17], wherein Xaa$_1$ is absent or is S or a hydrophilic amino acid, Xaa$_2$ is absent or is a hydrophilic amino acid, and Xaa$_3$ is absent or is from one to ten hydrophilic amino acids, (r) 8 or more contiguous amino acid residues from the sequence Xaa$_1$Xaa$_2$DRHSDYQPLGTQDQSL YLGLQHD GNDGLPPPPYSPRDDSSQHIYEEA [SEQ ID NO:18], wherein Xaa$_1$ is absent or is S or a hydrophilic amino acid, and Xaa$_2$ is absent or is from one to four hydrophilic amino acids, (s) 8 or more contiguous amino acid residues from the sequence SKKKKDRHSDYQPLGTQDQS-LYLGLQHDGNDGLPPPPYSPRDDSSQHIYEEA [SEQ ID NO:19], (t) 8 or more contiguous amino acid residues from the sequence DRHSDYQPLGTQDQSLYLGLQHDGNDG-LPPPPYSPRDDSSQHIYEEA [SEQ ID NO:20], (u) 8 or more contiguous amino acid residues from the sequence Xaa$_1$Xaa$_2$Xaa$_3$Xaa$_4$LLWTLVVLLICSS CSS-CPLSKILLARLFLYALALLL [SEQ ID NO: 21], wherein Xaa$_1$ is absent or is S or a hydrophilic amino acid, Xaa$_2$ is absent or is a hydrophilic amino acid, Xaa$_3$ is absent or is a hydrophilic amino acid, and Xaa$_4$ is absent or is one or more hydrophilic amino acids, (v) 8 or more contiguous amino acid residues from the sequence Xaa$_1$Xaa$_2$Xaa$_3$LLWTLVVLLICSSCS SCPL-SKI LLARLFLYALALLL [SEQ ID NO:22], wherein Xaa$_1$ is absent or is S or a hydrophilic amino acid, Xaa$_2$ is absent or is a hydrophilic amino acid, and Xaa$_3$ is absent or is from one to ten hydrophilic amino acids, (w) 8 or more contiguous amino acid residues from the sequence Xaa$_1$Xaa$_2$LLWTLVVLLICSSCSSCPLS KIL-LARLFLYALALLL [SEQ ID NO:23], wherein Xaa$_1$ is absent or is S or a hydrophilic amino acid, and Xaa$_2$ is absent or is from one to four hydrophilic amino acids, (x) 8 or more contiguous amino acid residues from the sequence SKKKKLLWTLVVLLICSSCSSCPLSKIL-LARLFLYALALLL [SEQ ID NO:24], (y) 8 or more contiguous amino acid residues from the sequence LLWTLVVLLICSSCSSCPLSKILLARLFLY-ALALLL [SEQ ID NO:25], (z) 8 or more contiguous amino acid residues from the sequence Xaa$_1$Xaa$_2$Xaa$_3$Xaa$_4$LMLLWTLVVLLICSS CSSCPLSKILLARLFLYALALLLLA [SEQ ID NO:26], wherein Xaa$_1$ is absent or is S or a hydrophilic amino acid, Xaa$_2$ is absent or is a hydrophilic amino acid, Xaa$_3$ is absent or is a hydrophilic amino acid, and Xaa$_4$ is absent or is one or more hydrophilic amino acids, (aa) 8 or more contiguous amino acid residues from the sequence Xaa$_1$Xaa$_2$Xaa$_3$LMLLWTLVVLLICSSCS SCPLSKILLARLFLYALALLLLA [SEQ ID NO:27], wherein Xaa$_1$ is absent or is S or a hydrophilic amino acid, Xaa$_2$ is absent or is a hydrophilic amino acid, and Xaa$_3$ is absent or is from one to ten hydrophilic amino acids, (bb) 8 or more contiguous amino acid residues from the sequence Xaa$_1$Xaa$_2$LMLLWTLVVLLICSSCSSC PLSKILLARLFLYALALLLLA [SEQ ID NO:28], wherein Xaa$_1$ is absent or is S or a hydrophilic amino acid, and Xaa$_2$ is absent or is from one to four hydrophilic amino acids, (cc) 8 or more contiguous amino acid residues from the sequence SKKKKLMLLWTLVVLLICSSCSSCPLSKIL-LARLFLYALALLLLA [SEQ ID NO:29], (dd) 8 or more contiguous amino acid residues from the sequence LMLLWTLVVLLICSSCSSCPLSKILLARL-FLYALALLLLA [SEQ ID NO:30], (ee) 8 or more contiguous amino acid residues from the sequence Xaa$_1$Xaa$_2$Xaa$_3$Xaa$_4$LMLLWTLVVLLICS SCSSCPLSKILL [SEQ ID NO:31], wherein Xaa$_1$ is absent or is S or a hydrophilic amino acid, Xaa$_2$ is absent or is a hydrophilic amino acid, Xaa$_3$ is absent or is a hydrophilic amino acid, and Xaa$_4$ is absent or is one or more hydrophilic amino acids, (ff) 8 or more contiguous amino acid residues from the sequence Xaa$_1$Xaa$_2$Xaa$_3$LMLLWTLVVLLICSSCSSCPLSKILL [SEQ ID NO:32], wherein Xaa$_1$ is absent or is S or a hydrophilic amino acid, Xaa$_2$ is absent or is a hydrophilic amino acid, and Xaa$_3$ is absent or is from one to ten hydrophilic amino acids, (gg) 8 or more contiguous amino acid residues from the sequence Xaa$_1$Xaa$_2$LMLLWTLVVLLICSSCSSCPLSKILL [SEQ ID NO:33], wherein Xaa$_1$ is absent or is S or a hydrophilic amino acid, and Xaa$_2$ is absent or is from one to four hydrophilic amino acids, (hh) 8 or more contiguous amino acid residues from the sequence SKKKKLMLLWTLVVLLICSSCSSCPL-SKILL [SEQ ID NO:34], (ii) 8 or more contiguous amino acid residues from the sequence LMLLWTLVVLLICSSCSSCPLSKILL [SEQ ID NO:35], (jj) 8 or more contiguous amino acid residues from the sequence Xaa$_1$Xaa$_2$Xaa$_3$Xaa$_4$LLICSSCSSCPLSKIL LARLFLYALALLLLA [SEQ ID NO:36], wherein Xaa$_1$ is absent or is S or a hydrophilic amino acid, Xaa$_2$ is absent or is a hydrophilic amino acid, $Xaa_3$ is absent or is a hydrophilic amino acid, and $Xaa_4$ is absent or is one or more hydrophilic amino acids, (kk) 8 or more contiguous amino acid residues from the sequence $Xaa_1Xaa_2Xaa_3$LLICSSCSSCPLSKILLA RLFLYALALLLLA [SEQ ID NO:37], wherein $Xaa_1$ is absent or is S or a hydrophilic amino acid, $Xaa_2$ is absent or is a hydrophilic amino acid, and $Xaa_3$ is absent or is from one to ten hydrophilic amino acids, (ll) 8 or more contiguous amino acid residues from the sequence $Xaa_1Xaa_2$LLICSSCSSCPLSKILLARLFLYALALLLLA [SEQ ID NO:38], wherein $Xaa_1$ is absent or is S or a hydrophilic amino acid, and $Xaa_2$ is absent or is from one to four hydrophilic amino acids, (mm) 8 or more contiguous amino acid residues from the sequence SKKKKLLICSSCSSCPLSKILLARLFLYALALLLLA [SEQ ID NO:39], (nn) 8 or more contiguous amino acid residues from the sequence LLICSSCSSCPLSKILLARLFLYALALLLLA [SEQ ID NO:40], (oo) 8 or more contiguous amino acid residues from the sequence $Xaa_1Xaa_2Xaa_3Xaa_4$LNLTTMFLLMLLWT LVVLLICSSCSSCPLSKILLARLFLYALALLLLA-SALIA GGSI [SEQ ID NO:41], wherein $Xaa_1$ is absent or is S or a hydrophilic amino acid, $Xaa_2$ is absent or is a hydrophilic amino acid, $Xaa_3$ is absent or is a hydrophilic amino acid, and $Xaa_4$ is absent or is one or more hydrophilic amino acids, (pp) 8 or more contiguous amino acid residues from the sequence $Xaa_1Xaa_2Xaa_3$LNLTTMFLLMLLWTLVVL-LICSSCSSCPLSKILLARLFLYALALLLLA-SALIAGGSI [SEQ ID NO:42], wherein $Xaa_1$ is absent or is S or a hydrophilic amino acid, $Xaa_2$ is absent or is a hydrophilic amino acid, and $Xaa_3$ is absent or is from one to ten hydrophilic amino acids, (qq) 8 or more contiguous amino acid residues from the sequence $Xaa_1Xaa_2$LNLTTMFLLMLLWTLVVLLI CSSCSSCPLSKILLARLFLYALALLLLASALIAGGSI [SEQ ID NO:43], wherein $Xaa_1$ is absent or is S or a hydrophilic amino acid, and $Xaa_2$ is absent or is from one to four hydrophilic amino acids, (rr) 8 or more contiguous amino acid residues from the sequence SKKKKLNLTTMFLLMLLWTLVVLLICSS-CSSCPLSKILLARLFLYALALLLLASALIAGGSI [SEQ ID NO:44], (ss) 8 or more contiguous amino acid residues from the sequence LNLTTMFLLMLLWTLVVLLICSSCSSCPL-SKILLARLFLYALALLLLASALIAGGSI [SEQ ID NO:45], (tt) 8 or more contiguous amino acid residues from the sequence $Xaa_1Xaa_2Xaa_3Xaa_4$FLLMLLWTLVVLL ICSS-CSSCPLSKILLARLFLYALALLLLASA [SEQ ID NO:46], wherein $Xaa_1$ is absent or is S or a hydrophilic amino acid, $Xaa_2$ is absent or is a hydrophilic amino acid, $Xaa_3$ is absent or is a hydrophilic amino acid, and $Xaa_4$ is absent or is one or more hydrophilic amino acids, (uu) 8 or more contiguous amino acid residues from the sequence $Xaa_1Xaa_2Xaa_3$FLLMLLWTLVVLLIC SSCSSCPLSKILLARLFLYALALLLLASA [SEQ ID NO:47], wherein $Xaa_1$ is absent or is S or a hydrophilic amino acid, $Xaa_2$ is absent or is a hydrophilic amino acid, and $Xaa_3$ is absent or is from one to ten hydrophilic amino acids, (vv) 8 or more contiguous amino acid residues from the sequence $Xaa_1Xaa_2$FLLMLLWTLVVLLICSSCS SCPL-SKILLARLFLYALALLLLASA [SEQ ID NO:48], wherein $Xaa_1$ is absent or is S or a hydrophilic amino acid, and $Xaa_2$ is absent or is from one to four hydrophilic amino acids, (ww) 8 or more contiguous amino acid residues from the sequence SKKKKFLLMLLWTLVVLLICSSCSSCPL-SKILLARLFLYALALLLLASA [SEQ ID NO:49], (xx) 8 or more contiguous amino acid residues from the sequence FLLMLLWTLVVLLICSSCSSCPLSKIL-LARLFLYALALLLLASA [SEQ ID NO:50], (yy) 8 or more contiguous amino acid residues from the sequence $Xaa_1Xaa_2Xaa_3Xaa_4$LQGIYVLVMLVLLIL AYRRRWRRLTVCGGIMFLACVLVLIVDAVLQL-SPLL [SEQ ID NO:51], wherein $Xaa_1$ is absent or is S or a hydrophilic amino acid, $Xaa_2$ is absent or is a hydrophilic amino acid, $Xaa_3$ is absent or is a hydrophilic amino acid, and $Xaa_4$ is absent or is one or more hydrophilic amino acids, (zz) 8 or more contiguous amino acid residues from the sequence $Xaa_1Xaa_2Xaa_3$LQGIYVLVMLVLLILA YRRRWRRLTVCGGIMFLACVLVLIVDAVLQLSPLL [SEQ ID NO:52], wherein $Xaa_1$ is absent or is S or a hydrophilic amino acid, $Xaa_2$ is absent or is a hydrophilic amino acid, and $Xaa_3$ is absent or is from one to ten hydrophilic amino acids, (aaa) 8 or more contiguous amino acid residues from the sequence $Xaa_1Xaa_2$LQGIYVLVMLVLLILAYR RRWRRLTVCGGIMFLACVLVLIVDAVLQLSPLL [SEQ ID NO:53], wherein $Xaa_1$ is absent or is S or a hydrophilic amino acid, and $Xaa_2$ is absent or is from one to four hydrophilic amino acids, (bbb) 8 or more contiguous amino acid residues from the sequence SKKKKLQGIYVLVMLVLLILAY-RRRWRRLTVCGGIMFLACVLVLIVDAVLQLSPLL [SEQ ID NO:54], (ccc) 8 or more contiguous amino acid residues from the sequence LQGIYVLVMLVLLILAYRRRWRRLTVCG-GIMFLACVLVLIVDAVLQLSPLL [SEQ ID NO:55], (ddd) 8 or more contiguous amino acid residues from the sequence $Xaa_1Xaa_2Xaa_3Xaa_4$SGNRTYGPVFM(C)(S) LGGLLTMVAGAVWLTVMSNTLLSAWILTAGFLI FLIGFA [SEQ ID NO:56], wherein $Xaa_1$ is absent or is S or a hydrophilic amino acid, $Xaa_2$ is absent or is a hydrophilic amino acid, $Xaa_3$ is absent or is a hydrophilic amino acid, and $Xaa_4$ is absent or is one or more hydrophilic amino acids, (eee) 8 or more contiguous amino acid residues from the sequence $Xaa_1Xaa_2Xaa_3$SGNRTYGPVFM(C)(S)LG-GLLTMVAGAVWLTVMSNTLLSAWILTAGFLIFLIG FA [SEQ ID NO:57], wherein $Xaa_1$ is absent or is S or a hydrophilic amino acid, $Xaa_2$ is absent or is a hydrophilic amino acid, and $Xaa_3$ is absent or is from one to ten hydrophilic amino acids, (fff) 8 or more contiguous amino acid residues from the sequence $Xaa_1Xaa_2$SGNRTYGPVFM(C)(S)LG-GLLTMVAGAVWLTVMSNTLLSAWILT-AGFLIFLIGFA [SEQ ID NO:58], wherein $Xaa_1$ is absent or is S or a hydrophilic amino acid, and $Xaa_2$ is absent or is from one to four hydrophilic amino acids, (ggg) 8 or more contiguous amino acid residues from the sequence SKKKKSGNRTYGPVFM(C)(S)LG-GLLTMVAGAVWLTVMSNTLLSAWILT-AGFLIFLIGFA [SEQ ID NO:59], (hhh) 8 or more contiguous amino acid residues from the sequence SGNRTYGPVFM(C)(S)LGGLLTMVAGA-VWLTVMSNTLLSAWILTAGFLIFLIGFA [SEQ ID NO:60], (iii) 8 or more contiguous amino acid residues from the sequence Xaa$_1$Xaa$_2$Xaa$_3$Xaa$_4$SNEEPPPPYEDPYWGNGDRHSDYQPLGTQDQSLYLGLQHDGNDG-LPP [SEQ ID NO:61], wherein Xaa$_1$ is absent or is S or a hydrophilic amino acid, Xaa$_2$ is absent or is a hydrophilic amino acid, Xaa$_3$ is absent or is a hydrophilic amino acid, and Xaa$_4$ is absent or is one or more hydrophilic amino acids, (jjj) 8 or more contiguous amino acid residues from the sequence Xaa$_1$Xaa$_2$Xaa$_3$SNEEPPPPYEDPYWGNGDRHSDYQPLGTQDQSLYLGLQHDGNDGLPP [SEQ ID NO:62], wherein Xaa$_1$ is absent or is S or a hydrophilic amino acid, Xaa$_2$ is absent or is a hydrophilic amino acid, and Xaa$_3$ is absent or is from one to ten hydrophilic amino acids, (kkk) 8 or more contiguous amino acid residues from the sequence Xaa$_1$Xaa$_2$SNEEPPPPYEDPYWGNGDRHSDYQPLGTQDQSLYLGLQHDGNDGLPP [SEQ ID NO:63], wherein Xaa$_1$ is absent or is S or a hydrophilic amino acid, and Xaa$_2$ is absent or is from one to four hydrophilic amino acids, (lll) 8 or more contiguous amino acid residues from the sequence SKKKKSNEEPPPPYEDPYWGNGDRHSDYQPLGTQDQSLYLGLQHDGNDGLPP [SEQ ID NO:64], (mmm) 8 or more contiguous amino acid residues from the sequence SNEEPPPPYEDPYWGNGDRHSDYQPLGTQDQSLYLGLQHDGNDGLPP [SEQ ID NO:65], (nnn) 8 or more contiguous amino acid residues from the sequence Xaa$_1$Xaa$_2$Xaa$_3$Xaa$_4$GNDGLPPPPYSPRDDSSQHIYEEAGRGSMNPVCLPVIVAPYLFW-LAAIAA S [SEQ ID NO:66], wherein Xaa$_1$ is absent or is S or a hydrophilic amino acid, Xaa$_2$ is absent or is a hydrophilic amino acid, Xaa$_3$ is absent or is a hydrophilic amino acid, and Xaa$_4$ is absent or is one or more hydrophilic amino acids, (ooo) 8 or more contiguous amino acid residues from the sequence Xaa$_1$Xaa$_2$Xaa$_3$GNDGLPPPPYSPRDDSSQHIYEEAGRGSMNPVCLPVIVAPYLFWLAA-IAAS [SEQ ID NO:67], wherein Xaa$_1$ is absent or is S or a hydrophilic amino acid, Xaa$_2$ is absent or is a hydrophilic amino acid, and Xaa$_3$ is absent or is from one to ten hydrophilic amino acids, (ppp) 8 or more contiguous amino acid residues from the sequence Xaa$_1$Xaa$_2$GNDGLPPPPYSPRDDSSQ HIY-EEAGRGSMNPVCLPVIVAPYLFWLAAIAAS [SEQ ID NO:68], wherein Xaa$_1$ is absent or is S or a hydrophilic amino acid, and Xaa$_2$ is absent or is from one to four hydrophilic amino acids, (qqq) 8 or more contiguous amino acid residues from the sequence SKKKKGNDGLPPPPYSPRDDSSQHIYEEA-GRGSMNPVCLPVIVAPYLFWLAAIAAS [SEQ ID NO:69], (rrr) 8 or more contiguous amino acid residues from the sequence GNDGLPPPPYSPRDDSSQHIYEEA-GRGSMNPVCLPVIVAPYLFWLAAIAAS [SEQ ID NO:70], (sss) 8 or more contiguous amino acid residues from the sequence Xaa$_1$Xaa$_2$Xaa$_3$Xaa$_4$AAIAASCFTASV STVVTATGLALSLLLLAA-VASSYAAAQRKLLTPVTVLT [SEQ ID NO:71], wherein Xaa$_1$ is absent or is S or a hydrophilic amino acid, Xaa$_2$ is absent or is a hydrophilic amino acid, Xaa$_3$ is absent or is a hydrophilic amino acid, and Xaa$_4$ is absent or is one or more hydrophilic amino acids, (ttt) 8 or more contiguous amino acid residues from the sequence Xaa$_1$Xaa$_2$Xaa$_3$AAIAASCFTASVSTVVT ATGLALSLLLLAAVASSYAAAQRKLLTPVTVLT [SEQ ID NO:72], wherein Xaa$_1$ is absent or is S or a hydrophilic amino acid, Xaa$_2$ is absent or is a hydrophilic amino acid, and Xaa$_3$ is absent or is from one to ten hydrophilic amino acids, (uuu) 8 or more contiguous amino acid residues from the sequence Xaa$_1$Xaa$_2$AAIAASCFTASVSTVVTAT GLALSLLLLAAVASSYAAAQRKLLTPVTVLT [SEQ ID NO:73], wherein Xaa$_1$ is absent or is S or a hydrophilic amino acid, and Xaa$_2$ is absent or is from one to four hydrophilic amino acids, (vvv) 8 or more contiguous amino acid residues from the sequence SKKKKAAIAASCF-TASVSTVVTATGLALSLLLLAA-VASSYAAAQRKLLTPVTVLT [SEQ ID NO:74], (www) 8 or more contiguous amino acid residues from the sequence AAIAASCFTASVSTVVTATGLALSLLL-LAAVASSYAAAQRKLLTPVTVLT [SEQ ID NO:75], (xxx) the sequence of any one of SEQ ID NOs: 1 to 75, (yyy) 8 or more contiguous amino acid residues from the sequence of any one of
ESNEEPPPPY [SEQ ID NO: 76],
SNEEPPPPY [SEQ ID NO: 77],
HSDYQPLGT [SEQ ID NO: 78],
PLGTQDQSL [SEQ ID NO: 79],
PLGTQDQSLY [SEQ ID NO: 80],
PLGTQDQSLY [SEQ ID NO: 80],
LGTQDQSLY [SEQ ID NO: 81],
GTQDQSLYL [SEQ ID NO: 82],
GTQDQSLYL [SEQ ID NO: 83],
GTQDQSLYLG [SEQ ID NO: 84],
QSLYLGLQH [SEQ ID NO: 85],
SLYLGLQHD [SEQ ID NO: 86],
SLYLGLQHD [SEQ ID NO: 86],
GLQHDGNDGL [SEQ ID NO: 87],
GNDGLPPPPY [SEQ ID NO: 88],
GLPPPPYSP [SEQ ID NO: 89],
GLPPPPYSPR [SEQ ID NO: 90],
GLPPPPYSPR [SEQ ID NO: 90],
PRDDSSQHIY [SEQ ID NO: 91],
RDDSSQHIY [SEQ ID NO: 92],
HIYEEAGRG [SEQ ID NO: 93],
ILLARLFLY [SEQ ID NO: 94],
SSCSSCPLSKI [SEQ ID NO: 95],
LLWTLVVLL [SEQ ID NO: 96],
FLYALALLL [SEQ ID NO: 97],
CLGGLLTMV [SEQ ID NO: 98],
LIVDAVLQL [SEQ ID NO: 99],
LTAGFLIFL [SEQ ID NO: 100],
TVCGGIMFL [SEQ ID NO: 101], (zzz) the sequence of any one of SEQ ID NOs: 76-101, (aaaa) or any combination of two or more of (a) to (zzz) above.

In one exemplary embodiment, the peptide comprises one or more epitopes derived from Latent Membrane Protein 2 (LMP2), for example, from full-length EBV LMP2 (amino acids 1-497). In one specifically contemplated embodiment, the peptide comprises, consists essentially of, or consists of an amino acid sequence selected from the group consisting of 8 or more contiguous amino acid residues from any one of SEQ ID NOs: 4, 5, 9, 10, 14, 15, 19, 20, 24, 25, 29, 30, 34, 35, 39, 40, 44, 45, 49, 50, 54, 55, 59, 60, 64, 65, 69, 70, 74, or 75.

In another specifically contemplated embodiment, the peptide comprises, consists essentially of, or consists of an amino acid sequence selected from the group consisting of 12 or more contiguous amino acid residues from any one of SEQ ID NOs: 4, 5, 9, 10, 14, 15, 19, 20, 24, 25, 29, 30, 34, 35, 39, 40, 44, 45, 49, 50, 54, 55, 59, 60, 64, 65, 69, 70, 74, or 75.

In another specifically contemplated embodiment, the peptide comprises, consists essentially of, or consists of an amino acid sequence selected from the group consisting of 15 or more, 18 or more, 20 or more, or 25 or more contiguous amino acid residues from any one of SEQ ID NOs: 4, 5, 9, 10, 14, 15, 19, 20, 24, 25, 29, 30, 34, 35, 39, 40, 44, 45, 49, 50, 54, 55, 59, 60, 64, 65, 69, 70, 74, or 75.

In one embodiment, the peptide comprises, consists essentially of, or consists of an amino acid sequence selected from the group consisting of any one of SEQ ID NOs: 4, 5, 9, 10, 14, 15, 19, 20, 24, 25, 29, 30, 34, 35, 39, 40, 44, 45, 49, 50, 54, 55, 59, 60, 64, 65, 69, 70, 74, or 75.

In another specifically contemplated embodiment, the peptide comprises, consists essentially of, or consists of an amino acid sequence selected from the group consisting of 15 or more, 18 or more, 20 or more, or 25 or more contiguous amino acid residues from any one of SEQ ID NOs: 1 to 75.

In one embodiment, the peptide comprises, consists essentially of, or consists of an amino acid sequence selected from the group consisting of any one of SEQ ID NOs: 1 to 75.

In one embodiment, the peptide comprises an amino acid sequence selected from the group consisting of any one of SEQ ID NOs: 76 to 101. In one example, the peptide comprises an amino acid sequence selected from the group consisting of any one of SEQ ID NOs: 76 to 93.

In one embodiment, the peptide comprises an amino acid sequence selected from the group consisting of any two or more of SEQ ID NOs: 76 to 101. In one example, the peptide comprises an amino acid sequence selected from the group consisting of any two or more of SEQ ID NOs: 76 to 93.

In one specifically contemplated embodiment, the reactive functional groups of the amino acids of the peptide-containing conjugation partner are unprotected.

In certain embodiments, one or more reactive functional groups of one or more amino acids of the peptide conjugate are unprotected.

In certain embodiments, one or more reactive functional groups of the amino acid of the amino acid conjugate are unprotected.

In certain embodiments, one or more reactive functional groups of one or more amino acids of the amino acid-comprising conjugation partner are unprotected.

In certain embodiments, the amino acid-comprising conjugation partner comprises a peptide, wherein the reactive functional groups of the side chains of the amino acids of the peptide are unprotected, with the exception of any thiols other than the thiol to be reacted.

In one specifically contemplated embodiment, the reactive functional groups of the amino acids of the peptide of the peptide-containing conjugation partner are unprotected. In one specifically contemplated embodiment, the reactive functional groups of the amino acids of the peptide of the peptide-containing conjugation partner are unprotected, with the exception of any thiols other than the thiol to be reacted.

In one aspect, the invention relates to a method of making a peptide-conjugate comprising a structure of the formula (A):

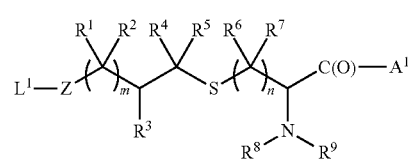

wherein
Z is selected from the group consisting of —O—, —NR—, —S—, —S(O)—, —SO$_2$—, —C(O)O—, —OC(O)—, —C(O)NR—, —NRC(O)—, —OC(O)O—, —NRC(O)O—, —OC(O)NR—, and —NRC(O)NR—;
R is hydrogen, C1-6alkyl, or C3-6cycloalkyl, wherein the alkyl or cycloalkyl is optionally substituted;
m is an integer from 0 to 4;
n is 1 or 2;
R1 and R2 at each instance of m are each independently hydrogen, C1-6alkyl, or C3-6cycloalkyl; or R1 is L2-C(O)—OC1-6alkyl;
R3, R4, R5, R8, and R9 are each independently hydrogen, C1-6alkyl, or C3-6cycloalkyl; or R3 is L2-C(O)—OC1-6alkyl;
or R9 is an amino protecting group, L3-C(O), or A2;
R6 and R7 at each instance of n are each independently hydrogen, C1-6alkyl, or C3-6cycloalkyl;
L1 and L2 are each independently C5-21alkyl or C4-20heteroalkyl;
L3 is C1-21alkyl or C4-20heteroalkyl;
A1 and A2 are each independently an amino acid or a peptide; or A1 is OH or OP1, wherein P1 is a carboxyl protecting group, and wherein A1 or A2 comprise one or more EBV LMP2 epitopes, or wherein A1, A2 or both A1 and A2 comprise one or more peptides selected from the group consisting of SEQ ID NOs: 1-101;
provided that:
    when R3 is L2-C(O)—OC1-6alkyl, R1 is not L2-C(O)—OC1-6alkyl; and
    when m is an integer from 2 to 4, no more than one R1 is L2-C(O)—OC1-6alkyl; and
wherein any alkyl, cycloalkyl or heteroalkyl present in any of R1, R2, R3, R4, R5, R6, R7, R8, R9, L1, L2 and L3 is optionally substituted;
or a pharmaceutically acceptable salt or solvate thereof.

In one embodiment, the method comprises making a peptide-conjugate comprising a structure of the formula (A):

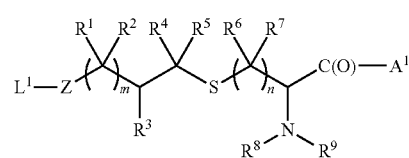

wherein
Z is selected from the group consisting of —O—, —NR—, —S—, —S(O)—, —SO$_2$—, —C(O)O—, —OC(O)—, —C(O)NR—, —NRC(O)—, —OC(O)O—, —NRC(O)O—, —OC(O)NR—, and —NRC(O)NR—;

R is hydrogen, C1-6alkyl, or C3-6cycloalkyl, wherein the alkyl or cycloalkyl is optionally substituted;
m is an integer from 0 to 4;
n is 1 or 2;
R1 and R2 at each instance of m are each independently hydrogen, C1-6alkyl, or C3-6cycloalkyl; or R1 is L2-C(O)—OC1-6alkyl;
R3, R4, R5, R8, and R9 are each independently hydrogen, C1-6alkyl, or C3-6cycloalkyl; or R3 is L2-C(O)—OC1-6alkyl;
or R9 is L3-C(O) or A2;
R6 and R7 at each instance of n are each independently hydrogen, C1-6alkyl, or C3-6cycloalkyl;
L1 and L2 are each independently C5-21alkyl or C4-20heteroalkyl;
L3 is C1-21alkyl or C4-20heteroalkyl;
A1 and A2 are each independently a peptide; or A1 is OH, and wherein A1 or A2 comprise one or more EBV LMP2 epitopes, or wherein A1, A2 or both A1 and A2 comprise one or more peptides selected from the group consisting of SEQ ID NOs: 1-101;
provided that:
when R9 is not A2, A1 is a peptide;
when R3 is L2-C(O)—OC1-6alkyl, R1 is not L2-C(O)—OC1-6alkyl; and
when m is an integer from 2 to 4, no more than one R1 is L2-C(O)—OC1-6alkyl; and wherein any alkyl, cycloalkyl or heteroalkyl present in any of R1, R2, R3, R4, R5, R6, R7, R8, R9, L1, L2 and L3 is optionally substituted;
or a pharmaceutically acceptable salt or solvate thereof.
In one embodiment, the method comprises making an amino acid or peptide-conjugate comprising a structure of the formula (B):

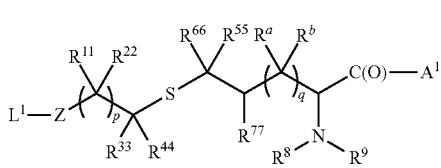

(B)

wherein
Z is selected from the group consisting of —O—, —NR—, —S—, —S(O)—, —SO$_2$—, —C(O)O—, —OC(O)—, —C(O)NR—, —NRC(O)—, —OC(O)O—, —NRC(O)O—, —OC(O)NR—, and —NRC(O)NR—;
R is hydrogen, C1-6alkyl, or C3-6cycloalkyl, wherein the alkyl or cycloalkyl is optionally substituted;
p is an integer from 0 to 4;
q is an integer from 0 to 2;
R11 and R22 at each instance of p are each independently hydrogen, C1-6alkyl, or C3-6cycloalkyl; or R11 is L2-C(O)—OC1-6alkyl;
R33, R44, R55, R66, R77, R8, and R9 are each independently hydrogen, C1-6alkyl, or C3-6cycloalkyl; or R33 is L2-C(O)—OC1-6alkyl;
or R9 is an amino protecting group, L3-C(O), or A2;
Ra and Rb at each instance of q are each independently hydrogen, C1-6alkyl, or C3-6cycloalkyl;
L1 and L2 are each independently C5-21alkyl or C4-20heteroalkyl;
L3 is C1-21alkyl or C4-20heteroalkyl;

A1 and A2 are each independently an amino acid or a peptide; or A1 is OH or OP1, wherein P1 is a carboxyl protecting group, and wherein A1 or A2 comprise one or more EBV LMP2 epitopes, or wherein A1, A2 or both A1 and A2 comprise one or more peptides selected from the group consisting of SEQ ID NOs: 1-101;
provided that:
when R33 is L2-C(O)—OC1-6alkyl, R11 is not L2-C(O)—OC1-6alkyl; and
when p is an integer from 2 to 4, no more than one R11 is L2-C(O)—OC1-6alkyl; and
wherein any alkyl, cycloalkyl, or heteroalkyl present in any of R11, R22, R 33, R44, R55, R66, R77, R8, R9, Ra, Rb, L1, L2, and L3 is optionally substituted;
or a pharmaceutically acceptable salt or solvate thereof.
In one embodiment, the method comprises making a peptide-conjugate comprising a structure of the formula (B):

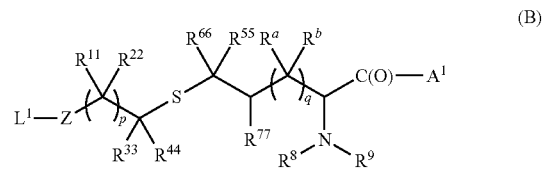

(B)

wherein
Z is selected from the group consisting of —O—, —NR—, —S—, —S(O)—, —SO$_2$—, —C(O)O—, —OC(O)—, —C(O)NR—, —NRC(O)—, —OC(O)O—, —NRC(O)O—, —OC(O)NR—, and —NRC(O)NR—;
R is hydrogen, C1-6alkyl, or C3-6cycloalkyl, wherein the alkyl or cycloalkyl is optionally substituted;
p is an integer from 0 to 4;
q is an integer from 0 to 2;
R11 and R22 at each instance of p are each independently hydrogen, C1-6alkyl, or C3-6cycloalkyl; or R11 is L2-C(O)—OC1-6alkyl;
R33, R44, R55, R66, R77, R8, and R9 are each independently hydrogen, C1-6alkyl, or C3-6cycloalkyl; or R33 is L2-C(O)—OC1-6alkyl;
or R9 is L3-C(O) or A2;
Ra and Rb at each instance of q are each independently hydrogen, C1-6alkyl, or C3-6cycloalkyl;
L1 and L2 are each independently C5-21alkyl or C4-20heteroalkyl;
L3 is C1-21alkyl or C4-20heteroalkyl;
A1 and A2 are each independently a peptide; or A1 is OH, and wherein A1 or A2 comprise one or more EBV LMP2 epitopes, or wherein A1, A2 or both A1 and A2 comprise one or more peptides selected from the group consisting of SEQ ID NOs: 1-101;
provided that:
when R9 is not A2, A1 is a peptide;
when R33 is L2-C(O)—OC1-6alkyl, R11 is not L2-C(O)—OC1-6alkyl; and
when p is an integer from 2 to 4, no more than one R11 is L2-C(O)—OC1-6alkyl; and
wherein any alkyl, cycloalkyl, or heteroalkyl present in any of R11, R22, R 33, R44, R55, R66, R77, R8, R9, Ra, Rb, L1, L2, and L3 is optionally substituted;
or a pharmaceutically acceptable salt or solvate thereof.
In one embodiment, the lipid-containing conjugation partner is a compound of the formula (A1):

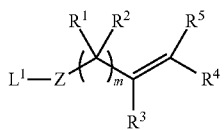

(A1)

wherein
- Z is selected from the group consisting of —O—, —NR—, —S—, —S(O)—, —SO$_2$—, —C(O)O—, —OC(O)—, —C(O)NR—, —NRC(O)—, —OC(O)O—, —NRC(O)O—, —OC(O)NR—, and —NRC(O)NR—;
- R is hydrogen, C1-6alkyl, or C3-6cycloalkyl, wherein the alkyl or cycloalkyl is optionally substituted;
- m is an integer from 0 to 4;
- R1 and R2 at each instance of m are each independently hydrogen, C1-6alkyl, or C3-6cycloalkyl; or R1 is L2-C(O)—OC1-6alkyl; R3, R4, and R5 are each independently hydrogen, C1-6alkyl, or C3-6cycloalkyl; or R3 is L2-C(O)—OC1-6alkyl;
- L1 and L2 are each independently C5-21alkyl or C4-20heteroalkyl;
- provided that:
  - when R3 is L2-C(O)—OC1-6alkyl, R1 is not L2-C(O)—OC1-6alkyl; and
  - when m is an integer from 2 to 4, no more than one R1 is L2-C(O)—OC1-6alkyl; and
- wherein any alkyl, cycloalkyl or heteroalkyl present in any of R1, R2, R3, R4, R5, L1, and L2 is optionally substituted,
- or a pharmaceutically acceptable salt or solvate thereof.

In another embodiment, the lipid containing conjugation partner is a compound of the formula (B1):

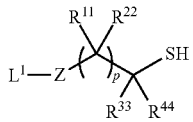

(B1)

wherein
- Z is selected from the group consisting of —O—, —NR—, —S—, —S(O)—, —SO$_2$—, —C(O)O—, —OC(O)—, —C(O)NR—, —NRC(O)—, —OC(O)O—, —NRC(O)O—, —OC(O)NR—, and —NRC(O)NR—;
- R is hydrogen, C1-6alkyl, or C3-6cycloalkyl, wherein the alkyl or cycloalkyl is optionally substituted;
- p is an integer from 0 to 4;
- R11 and R22 at each instance of p are each independently hydrogen, C1-6alkyl, or C3-6cycloalkyl; or R11 is L2-C(O)—OC1-6alkyl;
- R33 and R44 are each independently hydrogen, C1-6alkyl, or C3-6cycloalkyl; or R33 is L2-C(O)—OC1-6alkyl;
- L1 and L2 are each independently C5-21alkyl or C4-20heteroalkyl;
- provided that:
  - when R33 is L2-C(O)—OC1-6alkyl, R11 is not L2-C(O)—OC1-6alkyl; and
  - when p is an integer from 2 to 4, no more than one R11 is L2-C(O)—OC1-6alkyl; and
- wherein any alkyl, cycloalkyl, or heteroalkyl present in any of R11, R22, R 33, R44, L1, and L2 is optionally substituted;
- or a pharmaceutically acceptable salt or solvate thereof.

In one embodiment, the lipid-containing conjugation partner is a compound of the formula (II) as defined in any of the embodiments described herein.

In one embodiment, the lipid-containing conjugation partner is a compound of the formula (IIA) as defined in any of the embodiments described herein.

In one embodiment, the amino acid-comprising conjugation partner is a compound of the formula (III) as defined in any of the embodiments described herein.

In one embodiment, the peptide-containing conjugation partner is a compound of the formula (III) as defined in any of the embodiments described herein.

In one embodiment, the amino acid-comprising conjugation partner is a compound of the formula (IIIA) as defined in any of the embodiments described herein.

In one embodiment, the peptide-containing conjugation partner is a compound of the formula (IIIA) as defined in any of the embodiments described herein.

In one embodiment, the method comprises making an amino acid or peptide conjugate comprising a structure of the formula (I)

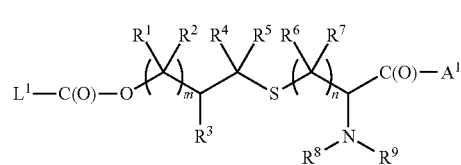

(I)

wherein
- m is an integer from 0 to 4;
- n is 1 or 2;
- R1 and R2 at each instance of m are each independently hydrogen, C1-6alkyl, or C3-6cycloalkyl; or R1 is L2-C(O)—OC1-6alkyl; R3, R4, R5, R8, and R9 are each independently hydrogen, C1-6alkyl, or C3-6cycloalkyl; or R3 is L2-C(O)—OC1-6alkyl;
- or R9 is an amino protecting group, L3-C(O), or A2; R6 and R7 at each instance of n are each independently hydrogen, C1-6alkyl, or C3-6cycloalkyl;
- L1 and L2 are each independently C5-21alkyl or C4-20heteroalkyl;
- L3 is C1-21alkyl or C4-20heteroalkyl;
- A1 and A2 are each independently an amino acid or a peptide; or A1 is OH or OP1, wherein P1 is a carboxyl protecting group, and wherein A1 or A2 comprise one or more EBV LMP2 epitopes, or wherein A1, A2 or both A1 and A2 comprise one or more peptides selected from the group consisting of SEQ ID NOs: 1-101;
- provided that:
  - when R3 is L2-C(O)—OC1-6alkyl, R1 is not L2-C(O)—OC1-6alkyl; and
  - when m is an integer from 2 to 4, no more than one R1 is L2-C(O)—OC1-6alkyl; and
- wherein any alkyl, cycloalkyl or heteroalkyl present in any of R1, R2, R3, R4, R5, R6, R7, R8, R9, L1, L2 and L3 is optionally substituted;
- or a pharmaceutically acceptable salt or solvate thereof;
the method comprising reacting a lipid-containing conjugation partner of the formula (II)

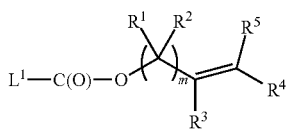

wherein m, R1, R2, R3, R4, R5, and L1 are as defined in the compound of formula (I);
and a peptide-containing conjugation partner comprising a structure of the formula (III)

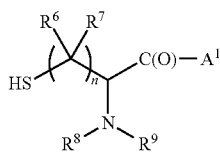

wherein n, R6, R7, R8, R9 and A1 are as defined in the compound of formula (I);
under conditions effective to conjugate the compound of formula (II) with the compound of formula (III) by hydrothiolation of the carbon-carbon double bond in the compound of formula (II) with the thiol in the compound of formula (III).

In one embodiment, the method comprises making a peptide conjugate comprising a structure of the formula (I)

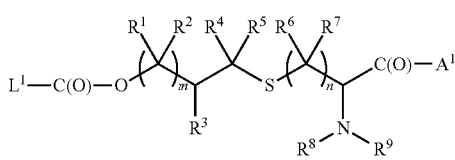

wherein
m is an integer from 0 to 4;
n is 1 or 2;
R1 and R2 at each instance of m are each independently hydrogen, C1-6alkyl, or C3-6cycloalkyl; or R1 is L2-C(O)—OC1-6alkyl;
R3, R4, R5, R8, and R9 are each independently hydrogen, C1-6alkyl, or C3-6cycloalkyl; or R3 is L2-C(O)—OC1-6alkyl;
or R9 is L3-C(O) or A2;
R6 and R7 at each instance of n are each independently hydrogen, C1-6alkyl, or C3-6cycloalkyl;
L1 and L2 are each independently C5-21alkyl or C4-20heteroalkyl;
L3 is C1-21alkyl or C4-20heteroalkyl;
A1 and A2 are each independently a peptide; or A1 is OH, and wherein A1 or A2 comprise one or more EBV LMP2 epitopes, or wherein A1, A2 or both A1 and A2 comprise one or more peptides selected from the group consisting of SEQ ID NOs: 1-101;
provided that:
when R9 is not A2, A1 is a peptide;
when R3 is L2-C(O)—OC1-6alkyl, R1 is not L2-C(O)—OC1-6alkyl; and when m is an integer from 2 to 4, no more than one R1 is L2-C(O)—OC1-6alkyl;
and wherein any alkyl, cycloalkyl or heteroalkyl present in any of R1, R2, R3, R4, R5, R6, R7, R8, R9, L1, L2 and L3 is optionally substituted;
or a pharmaceutically acceptable salt or solvate thereof;
the method comprising reacting a lipid-containing conjugation partner of the formula (II)

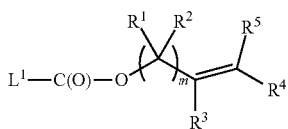

wherein m, R1, R2, R3, R4, R5, and L1 are as defined in the compound of formula (I);
and a peptide-containing conjugation partner comprising a structure of the formula (III)

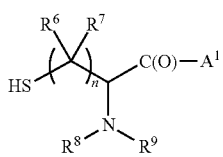

wherein n, R6, R7, R8, R9 and A1 are as defined in the compound of formula (I);
under conditions effective to conjugate the compound of formula (II) with the compound of formula (III) by hydrothiolation of the carbon-carbon double bond in the compound of formula (II) with the thiol in the compound of formula (III).

In one embodiment, the method comprises making an amino acid or peptide conjugate comprising a structure of the formula (IA),

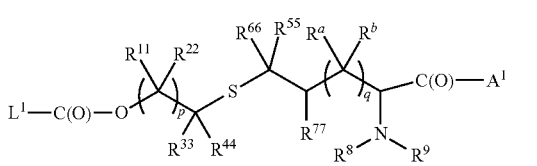

wherein
p is an integer from 0 to 4;
q is an integer from 0 to 2;
R11 and R22 at each instance of p are each independently hydrogen, C1-6alkyl, or C3-6cycloalkyl; or R11 is L2-C(O)—OC1-6alkyl;
R33, R44, R55, R66, R77, R8, and R9 are each independently hydrogen, C1-6alkyl, or C3-6cycloalkyl; or R33 is L2-C(O)—OC1-6alkyl;
or R9 is an amino protecting group, L3-C(O), or A2;
Ra and Rb at each instance of q are each independently hydrogen, C1-6alkyl, or C3-6cycloalkyl;
L1 and L2 are each independently C5-21alkyl or C4-20heteroalkyl;
L3 is C1-21alkyl or C4-20heteroalkyl;
A1 and A2 are each independently an amino acid or a peptide; or A1 is OH or OP1, wherein P1 is a carboxyl protecting group, and wherein A1 or A2 comprise one or more EBV LMP2 epitopes, or wherein A1, A2 or both A1 and A2 comprise one or more peptides selected from the group consisting of SEQ ID NOs: 1-101;
provided that:
when R33 is L2-C(O)—OC1-6alkyl, R11 is not L2-C(O)—OC1-6alkyl; and
when p is an integer from 2 to 4, no more than one R11 is L2-C(O)—OC1-6alkyl; and
wherein any alkyl, cycloalkyl, or heteroalkyl present in any of R11, R22, R 33, R44, R55, R66, R77, R8, R9, Ra, Rb, L1, L2, and L3 is optionally substituted;
or a pharmaceutically acceptable salt or solvate thereof;
the method comprising reacting a compound of the formula (IIA)

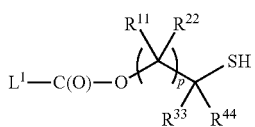

wherein p, R11, R22, R33, R44, and L1 are as defined in the compound of formula (IA);
and a compound of the formula (IIIA)

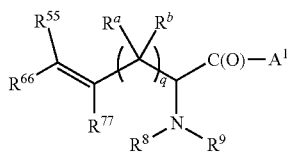

wherein q, R55, R66, R77, R8, R9, Ra, Rb, and A1 are as defined in the compound of formula (IA);
under conditions effective to conjugate the compound of formula (IIA) with the compound of formula (IIIA) by hydrothiolation of the carbon-carbon double bond in the compound of formula (IIIA) with the thiol in the compound of formula (IIA).

In one embodiment, the method comprises making a peptide conjugate comprising a structure of the formula (IA),

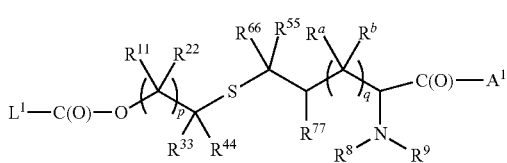

wherein
p is an integer from 0 to 4;
q is an integer from 0 to 2;
R11 and R22 at each instance of p are each independently hydrogen, C1-6alkyl, or C3-6cycloalkyl; or R11 is L2-C(O)—OC1-6alkyl;
R33, R44, R55, R66, R77, R8, and R9 are each independently hydrogen, C1-6alkyl, or C3-6cycloalkyl; or R33 is L2-C(O)—OC1-6alkyl;
or R9 is L3-C(O) or A2;

Ra and Rb at each instance of q are each independently hydrogen, C1-6alkyl, or C3-6cycloalkyl;
L1 and L2 are each independently C5-21alkyl or C4-20heteroalkyl;
L3 is C1-21alkyl or C4-20heteroalkyl;
A1 and A2 are each independently a peptide; or A1 is OH, and wherein A1 or A2 comprise one or more EBV LMP2 epitopes, or wherein A1, A2 or both A1 and A2 comprise one or more peptides selected from the group consisting of SEQ ID NOs: 1-101;
provided that:
when R9 is not A2, A1 is a peptide;
when R33 is L2-C(O)—OC1-6alkyl, R11 is not L2-C(O)—OC1-6alkyl; and
when p is an integer from 2 to 4, no more than one R11 is L2-C(O)—OC1-6alkyl; and
wherein any alkyl, cycloalkyl, or heteroalkyl present in any of R11, R22, R 33, R44, R55, R66, R77, R8, R9, Ra, Rb, L1, L2, and L3 is optionally substituted;
or a pharmaceutically acceptable salt or solvate thereof;
the method comprising reacting a compound of the formula (IIA)

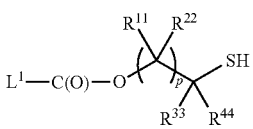

wherein p, R11, R22, R33, R44, and L1 are as defined in the compound of formula (IA);
and a compound of the formula (IIIA)

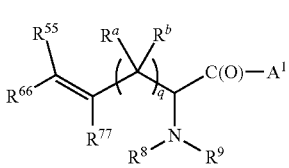

wherein q, R55, R66, R77, R8, R9, Ra, Rb, and A1 are as defined in the compound of formula (IA);
under conditions effective to conjugate the compound of formula (IIA) with the compound of formula (IIIA) by hydrothiolation of the carbon-carbon double bond in the compound of formula (IIIA) with the thiol in the compound of formula (IIA).

In one embodiment, at least one of L1 and L2 is C5-22alkyl.

In one embodiment, p is an integer from 0 to 2. In another embodiment, p is 0 or 1.

In some embodiments, R11 and R22 at each instance of p are each independently hydrogen; or R11 is L2-C(O)—OCH2. In one embodiment, R11 on the carbon adjacent to L1-C(O)—O is L2-C(O)—OCH2.

In one specifically contemplated embodiment, R11 and R22 at each instance of p are each independently hydrogen.

In one embodiment, R33 is hydrogen or L2-C(O)—OCH2.

In one embodiment, R33 and R44 are each hydrogen.

In one specifically contemplated embodiment, q is 0 or 1. In one specifically contemplated embodiment, q is 0.

In one specifically contemplated embodiment, R55, R66, and R77 are each hydrogen.

In some embodiments, Ra and Rb are at each instance of q are each hydrogen.

In one embodiment, L1 is C11-21alkyl; p is 1; R11 is hydrogen or L2-C(O)—OCH2; R22 is hydrogen; R33 is hydrogen or L2-C(O)—OCH2; R44 is hydrogen; and L2 is C11-21alkyl.

In one embodiment, R55, R66, R77, Ra, Rb and R8 are each hydrogen; and R9 is hydrogen, L3-C(O), or A2. In one embodiment, R55, R66, R77, Ra, Rb and R8 are each hydrogen; and R9 is hydrogen or L3-C(O).

In one embodiment, L1 is C11-21alkyl; p is 1; R11 is hydrogen or L2-C(O)—OCH2; R22 is hydrogen; R33 is hydrogen or L2-C(O)—OCH2; R44 is hydrogen; L2 is C11-21alkyl; R55, R66, R77, Ra, Rb and R8 are each hydrogen; and R9 is hydrogen, L3-C(O), or A2.

In one embodiment, L1 is C5-21alkyl. In another embodiment, L1 is C9-21alkyl. In yet another embodiment, L1 is C11-21alkyl. In one exemplary embodiment, L1 is C11, C13, C15, C17, or C19alkyl. In one specifically contemplated embodiment, L1 is C15alkyl.

In one embodiment, L1 comprises a linear chain of 9-21 carbon atoms. In one specifically contemplated embodiment, L1 is linear C15alkyl.

In one embodiment, m is an integer from 0 to 2. In another embodiment, m is 0 or 1.

In one specifically contemplated embodiment, m is 0.

In some embodiments, R1 and R2 at each instance of m are each independently hydrogen; or R1 is L2-C(O)—OCH2. In one embodiment, R1 on the carbon atom adjacent to L1-C(O)—O is L2-C(O)—OCH2.

In one specifically contemplated embodiment, R1 and R2 at each instance of m are each independently hydrogen.

In one embodiment, R3 is hydrogen or L2-C(O)—OCH2. In one specifically contemplated embodiment, R3 is hydrogen.

In one embodiment, L2 is C5-21alkyl. In another embodiment, L2 is C9-21alkyl. In yet another embodiment, L2 is C11-21 alkyl. In one exemplary embodiment, L2 is C11, C13, C15, C17, or C19alkyl. In another exemplary embodiment, L2 is C15alkyl.

In one specifically contemplated embodiment, R4 and R5 are each hydrogen.

In one specifically contemplated embodiment, n is 1.

In one specifically contemplated embodiment, R6 and R7 are each hydrogen.

In exemplary embodiments, R8 is hydrogen.

In one embodiment, R8 and R9 are each hydrogen; or R9 is L3-C(O) or A2. In one exemplary embodiment R8 is hydrogen and R9 is L3-C(O).

In some embodiments, L3 is C1-21alkyl. In one specifically contemplated embodiment, L3 is methyl or linear C15alkyl. In exemplary embodiments, L3 is methyl.

Those skilled in the art will appreciate that the structures of formula (III) and (IIIA) may comprise a peptide of the peptide-containing conjugation partner. As described herein, the peptide may be optionally substituted, modified, or bound to various other moieties as described herein to provide the peptide-containing conjugation partner.

In one embodiment, A1 is a peptide comprising an EBV LMP2 epitope. In one embodiment A2 is a peptide comprising an EBV LMP2 epitope.

In one embodiment, A1 is a peptide substituted with an epitope. In one embodiment, A2 is a peptide substituted with an epitope.

In one embodiment, the epitope is bound to the peptide via a linker group.

In one embodiment, the epitope is a peptide epitope.

In some embodiments, A1 and/or A2 are each independently a peptide comprising from about 8 to 220, 8 to 200, 8 to 175, 8 to 150, 8 to 125, 8 to 100, 8 to 90, 8 to 80, 8 to 70, 8 to 60, 8 to 50, 8 to 40, 8 to 30, 8 to 25, 8 to 20, or 8 to 15 amino acids. In one exemplary embodiment, A1 and A2 are each independently a peptide comprising from about 8 to 60 amino acids.

In other embodiments, A1 and/or A2 are each independently a peptide comprising from about 5 to 150, 5 to 125, 5 to 100, 5 to 75, 5 to 60, 5 to 50, 5 to 40, 5 to 30, 5 to 25, 5 to 20, 8 to 150, 8 to 125, 8 to 100, 8 to 75, 8 to 60, 8 to 50, 8 to 40, 8 to 30, 8 to 25, or 8 to 20 amino acids.

In some embodiments, A1 and/or A2 are each independently a peptide, wherein the peptide comprises 8 to 60 amino acids.

In some embodiments, A1 and/or A2 are each independently a peptide comprising or substituted with a peptide epitope, wherein the peptide epitope comprises from 8 to 60 amino acids.

In some embodiments, A1 and/or A2 are each independently a peptide comprising or substituted with a peptide epitope, wherein the peptide comprises, consists of, or consists essentially of an amino acid sequence selected from the group consisting of 8 or more, 10 or more, 12 or more, 15 or more, 20 or more, or 25 or more contiguous amino acids from the sequence of any one of SEQ ID NOs: 1-101, for example from the sequence of any one of SEQ ID NOs: 1-75.

In one embodiment, L1 is C11-21alkyl; m is 0; R3 is hydrogen or L2-C(O)—OCH2; L2 is C11-21alkyl; and R4 and R5 are each hydrogen.

In one embodiment, n is 1; R6, R7, and R8 are each hydrogen; and R9 is hydrogen, L3-C(O), or A2. In one embodiment, n is 1; R6, R7, and R8 are each hydrogen; and R9 is hydrogen or L3-C(O). In one embodiment, L3 is methyl or linear C15alkyl.

In one embodiment, L1 is C11-21alkyl; m is 0; R3 is hydrogen or L2-C(O)—OCH2; L2 is C11-21alkyl; R4 and R5 are each hydrogen; n is 1; R6, R7, and R8 are each hydrogen; R9 is hydrogen, L3-C(O), or A2. In one embodiment, L1 is C11-21alkyl; m is 0; R3 is hydrogen or L2-C(O)—OCH2; L2 is C11-21alkyl; R4 and R5 are each hydrogen; n is 1; R6, R7, and R8 are each hydrogen; R9 is hydrogen or L3-C(O).

In one embodiment, L1 is C11-21alkyl; m is 0; R3 is hydrogen; and R4 and R5 are each hydrogen.

In one embodiment, n is 1; R6, R7, and R8 are each hydrogen; and R9 is hydrogen, L3-C(O), or A2. In one embodiment, n is 1; R6, R7, and R8 are each hydrogen; and R9 is hydrogen or L3-C(O). In one embodiment, n is 1; R6, R7, and R8 are each hydrogen; and R9 is hydrogen or L3-C(O), wherein L3 is methyl.

In one embodiment, L1 is C11-21alkyl; m is 0; R3 is hydrogen; R4 and R5 are each hydrogen; n is 1; R6, R7, and R8 are each hydrogen; R9 is hydrogen, L3-C(O), or A2. In one embodiment, L1 is C11-21alkyl; m is 0; R3 is hydrogen; R4 and R5 are each hydrogen; n is 1; R6, R7, and R8 are each hydrogen; R9 is hydrogen or L3-C(O).

In one embodiment, L1 is C11-21alkyl; m is 0; R3 is hydrogen; R4 and R5 are each hydrogen; n is 1; R6, R7, and R8 are each hydrogen; R9 is hydrogen or L3-C(O), wherein L3 is methyl.

In one embodiment, L1 is C11-21alkyl; m is 0; R3 is hydrogen; and R4 and R5 are each hydrogen.

In one embodiment, n is 1; R6, R7, and R8 are each hydrogen; and R9 is hydrogen, 13-C(O), or A2. In one embodiment, n is 1; R6, R7, and R8 are each hydrogen; and R9 is hydrogen or L3-C(O). In one embodiment, n is 1; R6, R7, and R8 are each hydrogen; and R9 is hydrogen or L3-C(O), wherein L3 is methyl.

In one embodiment, L1 is C11-21alkyl; m is 0; R3 is hydrogen; R4 and R5 are each hydrogen; n is 1; R6, R7, and R8 are each hydrogen; R9 is hydrogen, L3-C(O), or A2. In one embodiment, L1 is C11-21alkyl; m is 0; R3 is hydrogen; R4 and R5 are each hydrogen; n is 1; R6, R7, and R8 are each hydrogen; R9 is hydrogen or L3-C(O).

In one embodiment, L1 is C11-21alkyl; m is 0; R3 is hydrogen; R4 and R5 are each hydrogen; n is 1; R6, R7, and R8 are each hydrogen; R9 is hydrogen or L3-C(O), wherein L3 is methyl.

In some embodiments, A1 is a peptide comprising serine as the first N-terminal amino acid residue. In some embodiments, A1 and/or A2 is a peptide comprising a solubilising group. In some embodiments, the solubilising group comprises an amino acid sequence comprising two or more hydrophilic amino acid residues in the peptide chain. In certain embodiments, A1 is a peptide comprising a solubilising group comprising an amino acid sequence comprising two or more hydrophilic amino acid residues in the peptide chain.

In some embodiments, A1 is a peptide comprising serine as the first N-terminal amino acid residue and a solubilising group comprising an amino acid sequence comprising two or more hydrophilic amino acid residues in the peptide chain adjacent to the serine.

In some embodiments, the solubilising group comprises an amino acid sequence comprising two or more consecutive hydrophilic amino acid residues in the peptide chain.

In one embodiment, the hydrophilic amino acid residues are cationic amino acid residues.

In one embodiment, the cationic amino acid residues are arginine or lysine residues. In one specifically contemplated embodiment, the cationic amino acid residues are lysine residues. In one embodiment, the sequence comprises from 2 to 20, 2 to 15, 2 to 10, 3 to 7, or 3 to 5 amino acids. In one embodiment, the solubilising group is a tri-, tetra-, penta-, hexa-, or hepta-lysine sequence. In one specifically contemplated embodiment, the solubilising group is a tetralysine sequence.

In some embodiments, R9 is hydrogen, an amino protecting group or L3-C(O). In some embodiments, R9 is hydrogen or L3-C(O).

In some embodiments, R9 is hydrogen or an amino protecting group, and the method further comprises acylating the amino acid conjugate or peptide conjugate so as to replace the hydrogen or amino protecting group at R9 with L3-C(O). In some embodiments, acylating the amino acid conjugate or peptide conjugate so as to replace the amino protecting group at R9 with L3-C(O) comprises removing the amino protecting group at R9 to provide a hydrogen at R9.

In some embodiments, A1 and/or A2 is an amino acid or a peptide. In some embodiments, A1 and/or A2 is a peptide.

In some embodiments, A1 is OH or OP1 and/or R9 is hydrogen, an amino protecting group or L3-C(O). In some embodiments, A1 is OP1 or OH and/or R9 is hydrogen, an amino protecting group or L3-C(O). In some embodiments, A1 is a OP1 or OH and R9 is hydrogen, an amino protecting group or L3-C(O).

In some embodiments, A1 is a OP1 or OH and/or R9 is hydrogen, an amino protecting group or L3-C(O), and the method comprises coupling an amino acid or a peptide so as to replace A1 and/or R9 with the amino acid or peptide.

In some embodiments, A1 is a OP1 or OH and R9 is hydrogen, an amino protecting group or L3-C(O) and the method further comprises coupling an amino acid or a peptide so as to replace A1 and/or R9 with the amino acid or peptide.

In some embodiments, coupling a peptide comprises individually coupling one or more amino acids and/or one or more peptides.

In some embodiments, coupling the amino acid or peptide provides a peptide conjugate comprising a peptide epitope. In some embodiments, the coupling the amino acid or peptide provides a peptide conjugate comprising a linker group or one or more amino acids thereof. In some embodiments, coupling the amino acid or peptide provides a peptide conjugate comprising a peptide epitope bound to the amino acid to which lipid-containing conjugation partner is conjugated via a linker group.

In some embodiments, the amino protecting group is Boc, Fmoc, Cbz (carboxybenzyl), Nosyl (o- or p-nitrophenylsulfonyl), Bpoc (2-(4-biphenyl)isopropoxycarbonyl) and Dde (1-(4,4-dimethyl-2,6-dioxohexylidene)ethyl). In some embodiments, the amino protecting group is Boc or Fmoc.

In some embodiments, the carboxyl protecting group is tert-butyl or benzyl. In one embodiment, the compound of the formula (I) is a compound of the formula (IV):

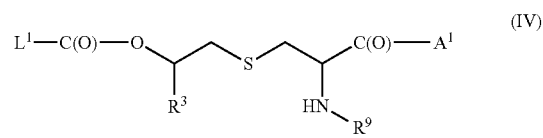

wherein
R3 is hydrogen or L2-C(O)—OCH2;
R9 is hydrogen, an amino protecting group, L3-C(O), or A2; and
L1 and L2 are each independently C5-21alkyl or C4-20heteroalkyl;
L3 is C1-21alkyl or C4-20heteroalkyl;
A1 and A2 are each independently an amino acid or a peptide; or A1 is OH or OP1, wherein P1 is a carboxyl protecting group, and wherein A1 or A2 comprise one or more EBV LMP2 epitopes, or wherein A1, A2 or both A1 and A2 comprise one or more peptides selected from the group consisting of SEQ ID NOs: 1-101;
or a pharmaceutically acceptable salt or solvate thereof.

In one embodiment, the compound of the formula (I) is a compound of the formula (IV):

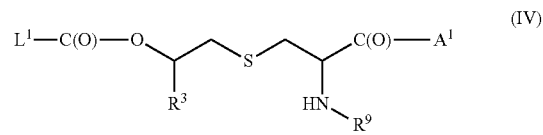

wherein
R3 is hydrogen or L2-C(O)—OCH2;
R9 is hydrogen, L3-C(O), or A2; and
L1 and L2 are each independently C5-21alkyl or C4-20heteroalkyl;
L3 is C1-21alkyl or C4-20heteroalkyl;

A1 and A2 are each independently a peptide; or A1 is OH, and wherein A1 or A2 comprise one or more EBV LMP2 epitopes, or wherein A1, A2 or both A1 and A2 comprise one or more peptides selected from the group consisting of SEQ ID NOs: 1-101;
provided that:
when R9 is not A2, A1 is a peptide;
or a pharmaceutically acceptable salt or solvate thereof.

In one embodiment, L1, A1, A2, L2, and L3 in the compound of formula (IV) are each independently as defined in any of the embodiments relating to the compound of the formula (I).

In one specifically contemplated embodiment, R3 is hydrogen.

In another specifically contemplated embodiment, R9 is acetyl.

In another specifically contemplated embodiment, R3 is hydrogen and R9 is acetyl.

In some embodiments, the method is for making a compound of the formula (IV), wherein L1 is C15 linear alkyl, R3 is hydrogen, R9 is Fmoc, and A1 is OH, and the method comprises reacting vinyl palmitate and Fmoc-Cys-OH.

In some embodiments, the amino protecting group is not Fmoc. In some embodiments, the amino protecting group is Boc.

In some embodiments, the amino acid-comprising conjugation partner is not Fmoc-Cys-OH.

In some embodiments, the peptide conjugate comprises 3 or more, 4 or more, or 5 or more contiguous amino acids. In some embodiments, the compound of formula (I) comprises 3 or more, 4 or more, or 5 or more contiguous amino acids.

In one embodiment, the conditions effective to conjugate the lipid-containing conjugation partner to the amino acid-comprising conjugation partner comprises the generation of one or more free radicals. In one embodiment, the conditions effective to conjugate the lipid-containing conjugation partner to the peptide-containing conjugation partner comprises the generation of one or more free radicals.

In some embodiments, the generation of one or more free radicals is initiated thermally and/or photochemically. In certain embodiments, the generation of one or more free radicals is initiated by the thermal and/or photochemical degradation of a free radical initiator. In exemplary embodiments, the generation of one or more free radicals is initiated by the thermal degradation of a thermal initiator or the photochemical degradation of a photochemical initiator.

In some embodiments, thermal degradation of the free radical initiator comprises heating the reaction mixture at a suitable temperature. In some embodiments, the reaction mixture is heated at a temperature from about 40° C. to about 200° C., from about 50° C. to about 180° C., from about 60° C. to about 150° C., from about 65° C. to about 120° C., from about 70° C. to about 115° C., from about 75° C. to about 110° C., or from about 80° C. to about 100° C. In other embodiments, the reaction mixture is heated at a temperature of at least about 40° C., at least about 50° C., at least about 60° C., or at least about 65° C. In one specifically contemplated embodiment, the reaction mixture is heated at a temperature of about 90° C.

In some embodiments, photochemical degradation of the free radical initiator comprises irradiation with ultraviolet light. In a specifically contemplated embodiment, the ultraviolet light has a wavelength of about 365 nm. In exemplary embodiments, photochemical degradation of the free radical initiator is carried out at about ambient temperature.

In one specifically contemplated embodiment, the thermal initiator is 2,2'-azobisisobutyronitrile (AIBN). In one specifically contemplated embodiment, the photoinitiator is 2,2-dimethoxy-2-phenylacetophenone (DMPA).

In certain embodiments, the reaction is carried out in a liquid medium. In one embodiment, the liquid medium comprises a solvent. In one embodiment, the solvent is selected from the group consisting of N-methylpyrrolidone (NMP), dimethylsulfoxide (DMSO), N,N-dimethylformamide (DMF), dichloromethane (DCM), 1,2-dichloroethane, and mixtures thereof. In one specifically contemplated embodiment, the solvent comprises NMP, DMSO, or a mixture thereof.

In one specifically contemplated embodiment, the solvent comprises DMSO.

In some embodiments, the reaction is carried out in the presence of one or more additives that inhibit dimerisation, telomerisation, or polymerisation. In some exemplary embodiments, the additive is selected from the group consisting of reduced glutathione (GSH), 2,2'-(ethylenedioxy) diethanethiol (DODT), 1,4-dithiothreitol (DTT), and protein. In a specifically contemplated embodiment, the additive is DTT. In some embodiments, the additive is DTT or tert-butyl mercaptan.

In some embodiments, the one or more additive is selected from the group consisting of TFA, tert-butyl mercaptan, and a combination thereof. In certain embodiments, the one or more additive is a combination of TFA and tert-butyl mercaptan. In some embodiments, the reaction is carried out for a period of time from about 5 minutes to about 48 h, 5 minutes to about 24 h, from about 5 minutes to about 12 hours, from about 5 minutes to about 6 hours, from about 5 minutes to about 3 hours, 5 minutes to 2 hours, or form about 5 minutes to about 1 hour. In exemplary embodiments, the reaction is carried out for a period of time from about 5 minutes to about 1 h. In some embodiments, the reaction is carried out until one of the conjugation partners is at least about 70%, 80%, 90%, 95%, 97%, 99%, or 100% consumed.

In certain embodiments, the reaction is carried out under substantially oxygen free conditions.

In some embodiments, the method comprises
reacting the lipid-containing conjugation partner and an amino acid-comprising conjugation partner to provide an amino acid or peptide conjugate;
synthesising the amino acid sequence of a peptide by solid phase peptide synthesis (SPPS);
coupling the amino acid of the amino acid conjugate or an amino acid of the peptide conjugate to the solid phase bound peptide by SPPS so as to provide a peptide conjugate comprising a peptide epitope, a peptide conjugate comprising a linker group or one or more amino acids thereof, or a peptide conjugate comprising a peptide epitope bound to the amino acid to which lipid-containing conjugation partner is conjugated via a linker group.

In some embodiments, the method further comprises acylating the Nα-amino group of the amino acid of the amino acid conjugate or the amino acid to which the lipid-containing conjugation partner is conjugated of any one of the peptide conjugates.

In some embodiments, the method comprises cleaving the peptide conjugate from the solid phase support.

In some embodiments, the method comprises
synthesising the amino acid sequence of the peptide of the peptide-containing conjugation partner by solid phase peptide synthesis (SPPS); and reacting the lipid-containing conjugation partner and peptide-containing conjugation partner in accordance with any of the embodiments described herein.

In exemplary embodiments, the method comprises synthesising the amino acid sequence of the peptide of the peptide-containing conjugation partner by SPPS, cleaving the peptide from the solid phase support; and reacting the lipid-containing conjugation partner and peptide-containing conjugation partner in accordance with any of the embodiments described herein.

In one embodiment, the peptide-containing conjugation partner is not purified prior to reaction with the lipid-containing conjugation partner.

In some embodiments, one or more protecting groups are removed on cleaving the peptide from the solid phase support. In certain embodiments, all of the protecting groups present in the peptide are removed.

In one embodiment, the SPPS is Fmoc-SPPS.

In some embodiments, the amino acid residue in the peptide of the peptide-containing conjugation partner bearing the carbon-carbon double bond or thiol to be reacted is an N-terminal amino acid residue and the method comprises acylating the N-terminal amino group prior to cleaving the peptide from the solid phase. In exemplary embodiments, the amino acid residue is an N-terminal residue. In specifically contemplated embodiments, the N-terminal residue is a cysteine residue.

In one embodiment, the method further comprises separating the peptide conjugate from the reaction medium and optionally purifying the peptide conjugate.

In another aspect, the present invention provides a compound of the formula (V):

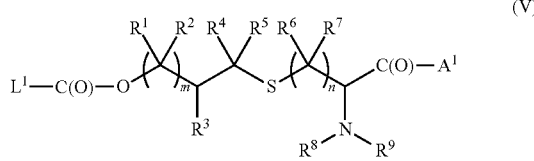

wherein
m is an integer from 0 to 4;
n is 1 or 2;
R1 and R2 at each instance of m are each independently hydrogen, C1-6alkyl, or C3-6cycloalkyl;
R3, R4, R5, R8, and R9 are each independently hydrogen, C1-6alkyl, or C3-6cycloalkyl; or R9 is an amino protecting group, L3-C(O), or A2;
R6 and R7 at each instance of n are each independently hydrogen, C1-6alkyl, or C3-6cycloalkyl;
L1 is C5-21alkyl or C4-20heteroalkyl;
L3 is C1-6alkyl or C3-6cycloalkyl;
A1 and A2 are each independently an amino acid or a peptide; or A1 is OH or OP1, wherein P1 is a carboxyl protecting group, and wherein A1 or A2 comprise one or more EBV LMP2 epitopes, or wherein A1, A2 or both A1 and A2 comprise one or more peptides selected from the group consisting of SEQ ID NOs: 1-101; and
wherein any alkyl, cycloalkyl or heteroalkyl present in any of R1, R2, R3, R4, R5, R6, R7, R8, R9, L1, and L3 is optionally substituted, and or a pharmaceutically acceptable salt or solvate thereof.

In another aspect, the present invention provides a compound of the formula (V):

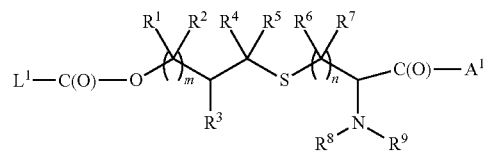

wherein
m is an integer from 0 to 4;
n is 1 or 2;
R1 and R2 at each instance of m are each independently hydrogen, C1-6alkyl, or C3-6cycloalkyl;
R3, R4, R5, R8, and R9 are each independently hydrogen, C1-6alkyl, or C3-6cycloalkyl; or R9 is L3-C(O) or A2;
R6 and R7 at each instance of n are each independently hydrogen, C1-6alkyl, or C3-6cycloalkyl;
L1 is C5-21alkyl or C4-20heteroalkyl;
L3 is C1-6alkyl or C3-6cycloalkyl;
A1 and A2 are each independently a peptide; or A1 is OH, and wherein A1 or A2 comprise one or more EBV LMP2 epitopes, or wherein A1, A2 or both A1 and A2 comprise one or more peptides selected from the group consisting of SEQ ID NOs: 1-101;
provided that:
when R9 is not A2, A1 is a peptide; and
wherein any alkyl, cycloalkyl or heteroalkyl present in any of R1, R2, R3, R4, R5, R6, R7, R8, R9, L1, and L3 is optionally substituted, and or a pharmaceutically acceptable salt or solvate thereof.

In one embodiment, m, n, R6, R7, A1 and A2 are each independently as defined in any of the embodiments relating to the compound of formula (I).

In one embodiment, L1 is C5-21alkyl. In one embodiment, L1 is C5-21alkyl. In another embodiment, L1 is C9-21alkyl. In yet another embodiment, L1 is C11-21alkyl. In one exemplary embodiment, L1 is C11, C13, C15, C17, or C19alkyl. In one specifically contemplated embodiment, L1 is C15alkyl.

In one embodiment, L1 comprises a linear chain of 9-21 carbon atoms. In one specifically contemplated embodiment, L1 is linear C15alkyl.

In one embodiment, m is an integer from 0 to 2. In another embodiment, m is 0 or 1.

In one specifically contemplated embodiment, m is 0.

In one specifically contemplated embodiment, R1 and R2 at each instance of m are each independently hydrogen.

In one specifically contemplated embodiment, R3 is hydrogen.

In one specifically contemplated embodiment, R4 and R5 are each hydrogen.

In one specifically contemplated embodiment, n is 1.

In one specifically contemplated embodiment, R6 and R7 are each hydrogen.

In exemplary embodiments, R8 is hydrogen.

In some embodiments, R8 is hydrogen and R9 is hydrogen, an amino protecting group, L3-C(O), or A2. In one embodiment, R8 and R9 are each hydrogen; or R9 is L3-C(O) or A2. In one exemplary embodiment R8 is hydrogen and R9 is L3-C(O). In one specifically contemplated embodiment, L3 is methyl.

In some embodiments, A1 is OP1 or OH and R9 is hydrogen, an amino protecting group or L3-C(O).

In some embodiments, A1 and/or A2 is an amino acid or a peptide. In some embodiments, the peptide comprises an epitope.

In some embodiments, A1 is serine or a peptide comprising serine as the first N-terminal amino acid residue.

In some embodiments, A1 and/or A2 is a peptide comprising a solubilising group comprising an amino acid sequence comprising two or more hydrophilic amino acid residues in the peptide chain.

In some embodiments, A1 is a peptide comprising serine as the first N-terminal amino acid residue and a solubilising group comprising an amino acid sequence comprising two or more hydrophilic amino acid residues in the peptide chain adjacent to the serine.

In one embodiment, L1 is C11-21alkyl; m is 0; R3 is hydrogen; and R4 and R5 are each hydrogen.

In one embodiment, n is 1; R6, R7, and R8 are each hydrogen; and R9 is hydrogen, L3-C(O), or A2. In one embodiment, n is 1; R6, R7, and R8 are each hydrogen; and R9 is hydrogen or L3-C(O). In one embodiment, n is 1; R6, R7, and R8 are each hydrogen; and R9 is hydrogen or L3-C(O), wherein L3 is methyl.

In one embodiment, L1 is C11-21alkyl; m is 0; R3 is hydrogen; R4 and R5 are each hydrogen; n is 1; R6, R7, and R8 are each hydrogen; R9 is hydrogen, L3-C(O), or A2. In one embodiment, L1 is C11-21alkyl; m is 0; R3 is hydrogen; R4 and R5 are each hydrogen; n is 1; R6, R7, and R8 are each hydrogen; R9 is hydrogen or L3-C(O).

In one embodiment, L1 is C11-21alkyl; m is 0; R3 is hydrogen; R4 and R5 are each hydrogen; n is 1; R6, R7, and R8 are each hydrogen; R9 is hydrogen or L3-C(O), wherein L3 is methyl.

In some embodiments, L1 is C15 linear alkyl; m is 0; n is 1; R3, R4, R5, R6, R7, and R8 are each hydrogen; R9 is Fmoc, and A1 is OH in the compound of the formula (V).

In some embodiments, the amino protecting group of R9 is not Fmoc. In some embodiments, the amino protecting group of R9 is Boc.

In some embodiments, the compound of formula (V) comprises 3 or more, 4 or more, or 5 or more contiguous amino acids.

In some embodiments, the amino and/or carboxyl protecting groups are as defined in any of the embodiments relating to the compound of formula (I).

Those skilled in the art will appreciate that compound of formula (V) is a peptide conjugate and certain embodiments relating to the peptide conjugates of the conjugation method described herein also apply to the compounds of formula (V).

In some embodiments, the compound of formula (V) is a self adjuvanting peptide.

In some embodiments, the compound comprises a linker or one or more amino acids thereof. In some embodiments, the peptide comprises a linker or one or more amino acids thereof. In some embodiments, the peptide comprises a peptide epitope bound to via a linker to the amino acid to which L1 is bound. In some embodiments, the peptide comprises two or more epitopes. In some embodiments, the linker is an amino acid sequence from about 2 to 20, 2 to 18, 2 to 16, 2 to 14, 2 to 12, 2 to 10, or 2 to 8 amino acids in length.

In another aspect, the present invention provides a pharmaceutical composition comprising an effective amount of a peptide conjugate of the present invention or a pharmaceutically acceptable salt or solvate thereof, and a pharmaceutically acceptable carrier.

In one embodiment, the pharmaceutical composition is an immunogenic composition.

In one embodiment, the composition does not include an extrinsic adjuvant.

In some embodiments, the composition is a vaccine.

In one embodiment, the pharmaceutical composition comprises an effective amount of two or more peptide conjugates of the present invention, for example the pharmaceutical composition comprises an effective amount of three or more peptide conjugates of the present invention. In one example, the pharmaceutical composition comprises an effective amount of two or more peptide conjugates of the invention, wherein the two or more peptide conjugates comprise substantially all of the immunogenic regions of LMP2.

In another aspect, the present invention provides a pharmaceutical composition comprising an effective amount of a peptide of the present invention or a pharmaceutically acceptable salt or solvate thereof, and a pharmaceutically acceptable carrier.

In one embodiment, the pharmaceutical composition comprises an effective amount of two or more peptides of the present invention, for example the pharmaceutical composition comprises an effective amount of three or more peptides of the present invention.

In one embodiment, the pharmaceutical composition comprises an effective amount of one or more peptide conjugates of the present invention together with one or more peptides of the present invention, or any combination thereof. For example, the pharmaceutical composition comprises an effective amount of two or more peptide conjugates of the present invention and one or more peptides of the present invention, or an effective amount of one or more peptide conjugates of the present invention and two or more peptides of the present invention.

In another aspect, the present invention provides a method of vaccinating or eliciting an immune response in a subject comprising administering to the subject an effective amount of a peptide conjugate or peptide of the present invention.

In another aspect, the present invention provides use of a peptide conjugate or peptide of the invention for vaccinating or eliciting an immune response in a subject.

In another aspect, the present invention provides use of a peptide conjugate or a peptide of the invention in the manufacture of a medicament for vaccinating or eliciting an immune response in a subject.

In another aspect, the present invention provides a method of vaccinating or eliciting an immune response in a subject comprising administering to the subject an effective amount of the pharmaceutical composition of the present invention.

In another aspect, the present invention provides use of a pharmaceutical composition of the invention for vaccinating or eliciting an immune response in a subject.

In another aspect, the present invention provides use of one or more peptides of the present invention or one or more peptide conjugates of the present invention in the manufacture of a medicament for vaccinating or eliciting an immune response in a subject.

In another aspect, the present invention provides a method of eliciting an immune response in a subject comprising administering to the subject an effective amount of a peptide conjugate of the present invention or a pharmaceutically acceptable salt or solvate thereof.

In another aspect, the present invention provides use of a peptide conjugate of the invention or a pharmaceutically acceptable salt or solvate thereof for eliciting an immune response in a subject.

In another aspect, the present invention provides use of a peptide conjugate of the invention or a pharmaceutically acceptable salt or solvate thereof in the manufacture of a medicament for eliciting an immune response in a subject.

In another aspect, the present invention provides a method of vaccinating a subject comprising administering to the subject an effective amount of a peptide conjugate of the present invention or a pharmaceutically acceptable salt or solvate thereof.

In another aspect, the present invention provides use of a peptide conjugate of the present invention for vaccinating a subject or a pharmaceutically acceptable salt or solvate thereof.

In another aspect, the present invention provides use of a peptide conjugate of the invention or a pharmaceutically acceptable salt or solvate thereof in the manufacture of a medicament for vaccinating a subject.

In some embodiments, the method comprises the administration of one or more peptides of the present invention and/or one or more peptide conjugates of the present invention, for example one or more peptides in combination with one or more peptide conjugates to the subject.

In some embodiments, one or more peptides of the present invention and/or one or more peptide conjugates of the present invention, for example one or more peptides in combination with one or more peptide conjugates are used for vaccinating or eliciting an immune response in the subject or in the manufacture of a medicament for vaccinating or eliciting an immune response in the subject.

In some embodiment, two or more peptides, two or more peptide conjugates, or one or more peptides and one or more peptide conjugates are used or administered. In some embodiments the two or more peptides, two or more peptide conjugates, or one or more peptides and one or more peptide conjugates are used or administered simultaneously, sequentially, or separately.

Asymmetric centers may exist in the compounds described herein. The asymmetric centers may be designated as (R) or (S), depending on the configuration of substituents in three dimensional space at the chiral carbon atom. All stereochemical isomeric forms of the compounds, including diastereomeric, enantiomeric, and epimeric forms, as well as d-isomers and l-isomers, and mixtures thereof, including enantiomerically enriched and diastereomerically enriched mixtures of stereochemical isomers, are within the scope of the invention.

Individual enantiomers can be prepared synthetically from commercially available enantiopure starting materials or by preparing enantiomeric mixtures and resolving the mixture into individual enantiomers. Resolution methods include conversion of the enantiomeric mixture into a mixture of diastereomers and separation of the diastereomers by, for example, recrystallization or chromatography, and any other appropriate methods known in the art. Starting materials of defined stereochemistry may be commercially available or made and, if necessary, resolved by techniques well known in the art.

The compounds described herein may also exist as conformational or geometric isomers, including cis, trans, syn, anti, entgegen (E), and zusammen (Z) isomers. All such isomers and any mixtures thereof are within the scope of the invention.

Also within the scope of the invention are any tautomeric isomers or mixtures thereof of the compounds described. As would be appreciated by those skilled in the art, a wide variety of functional groups and other structures may exhibit tautomerism. Examples include, but are not limited to, keto/enol, imine/enamine, and thioketone/enethiol tautomerism.

The compounds described herein may also exist as isotopologues and isotopomers, wherein one or more atoms in the compounds are replaced with different isotopes.

Suitable isotopes include, for example, $^1$H, $^2$H (D), $^3$H (T), $^{12}$C, $^{13}$C, $^{14}$C, $^{16}$O, and $^{18}$O. Procedures for incorporating such isotopes into the compounds described herein will be apparent to those skilled in the art. Isotopologues and isotopomers of the compounds described herein are also within the scope of the invention.

Also within the scope of the invention are pharmaceutically acceptable salts and solvates, including hydrates of the compounds described herein. Such salts include, acid addition salts, base addition salts, and quaternary salts of basic nitrogen-containing groups.

Acid addition salts can be prepared by reacting compounds, in free base form, with inorganic or organic acids. Examples of inorganic acids include, but are not limited to, hydrochloric, hydrobromic, nitric, sulfuric, and phosphoric acid. Examples of organic acids include, but are not limited to, acetic, trifluoroacetic, propionic, succinic, glycolic, lactic, malic, tartaric, citric, ascorbic, maleic, fumaric, pyruvic, aspartic, glutamic, stearic, salicylic, methanesulfonic, benzenesulfonic, isethionic, sulfanilic, adipic, butyric, and pivalic.

Base addition salts can be prepared by reacting compounds, in free acid form, with inorganic or organic bases. Examples of inorganic base addition salts include alkali metal salts, alkaline earth metal salts, and other physiologically acceptable metal salts, for example, aluminium, calcium, lithium, magnesium, potassium, sodium, or zinc salts. Examples of organic base addition salts include amine salts, for example, salts of trimethylamine, diethylamine, ethanolamine, diethanolamine, and ethylenediamine.

Quaternary salts of basic nitrogen-containing groups in the compounds may be may be prepared by, for example, reacting the compounds with alkyl halides such as methyl, ethyl, propyl, and butyl chlorides, bromides, and iodides, dialkyl sulfates such as dimethyl, diethyl, dibutyl, and diamyl sulfates, and the like.

The general chemical terms used in the formulae herein have their usual meaning.

The term "aliphatic" is intended to include saturated and unsaturated, nonaromatic, straight chain, branched, acyclic, and cyclic hydrocarbons. Those skilled in the art will appreciate that aliphatic groups include, for example, alkyl, alkenyl, alkynyl, cycloalkyl, and cycloalkenyl groups. In some embodiments, the aliphatic group is saturated.

The term "heteroaliphatic" is intended to include aliphatic groups, wherein one or more chain carbon atoms are replaced with a heteroatom. In some embodiments, the heteroaliphatic is saturated.

The term "alkyl" is intended to include saturated or unsaturated straight chain and branched chain hydrocarbon groups. Examples of saturated hydrocarbon groups include methyl, ethyl, n-propyl, isopropyl, n-butyl, t-butyl, isobutyl, sec-butyl, and the like. Unsaturated alkyl groups have one or more carbon-carbon double bonds or triple bonds. Examples of unsaturated alkyl groups include vinyl, prop-2-enyl, crotyl, isopent-2-enyl, 2-butadienyl, penta-2,4-dienyl, penta-1,4-dienyl, ethynyl, prop-3-ynyl, but-3-ynyl, and the like. In some embodiments, the alkyl is saturated.

The term "heteroalkyl" is intended to include alkyl groups, wherein one or more chain carbon atoms are replaced with a heteroatom. In some embodiments, the heteroalkyl is saturated.

The term "cycloalkyl" is intended to include non-aromatic cyclic alkyl groups. Examples of cycloalkyl groups include but are not limited to cyclopentyl, cyclohexyl, cyclohex-1-enyl, cyclohex-3-enyl, cycloheptyl. In some embodiments, the cycloalkyl is saturated.

The term "heteroatom" is intended to include oxygen, nitrogen, sulfur, or phosphorus. In some embodiments, the heteroatom is selected from the group consisting of oxygen, nitrogen, and sulfur.

The term "aryl" is intended to include aromatic radicals. Examples include, but are not limited to, phenyl, tolyl, naphthyl, indanyl, and the like. In some embodiments, aryl groups comprise from 4 to 8 or from 6 to 8 carbon atoms in the aromatic ring system.

As used herein, the term "substituted" is intended to mean that one or more hydrogen atoms in the group indicated is replaced with one or more independently selected suitable substituents, provided that the normal valency of each atom to which the substituent/s are attached is not exceeded, and that the substitution results in a stable compound.

Examples of optional substituents for aliphatic, heteroaliphatic, alkyl, heteroalkyl, and cycloalkyl groups in the compounds described herein include but are not limited to halo, CN, $NO_2$, OH, $NH_2$, NHR1, NR1R2, C1-6haloalkyl, C1-6haloalkoxy, $C(O)NH_2$, C(O)NHR1, C(O)NR1R1, $SO_2R1$, OR1, SR1, S(O)R1, C(O)R1, and C1-6aliphatic; wherein R1 and R2 are each independently C1-6alkyl.

The term "carboxyl protecting group" as used herein means a group that is capable of readily removed to provide the OH group of a carboxyl group and protects the carboxyl group against undesirable reaction during synthetic procedures. Such protecting groups are described in Protective Groups in Organic Synthesis edited by T. W. Greene et al. (John Wiley & Sons, 1999) and 'Amino Acid-Protecting Groups' by Fernando Albericio (with Albert Isidro-Llobet and Mercedes Alvarez) Chemical Reviews 2009 (109) 2455-2504. Examples include, but are not limited to, alkyl and silyl groups, for example methyl, ethyl, tert-butyl, methoxymethyl, 2,2,2-trichloroethyl, benzyl, diphenylmethyl, trimethylsilyl, and tert-butyldimethylsilyl, and the like.

The term "amine protecting group" as used herein means a group that is capable of being readily removed to provide the $NH_2$ group of an amine group and protects the amine group against undesirable reaction during synthetic procedures. Such protecting groups are described in Protective Groups in Organic Synthesis edited by T. W. Greene et al. (John Wiley & Sons, 1999) and 'Amino Acid-Protecting Groups' by Fernando Albericio (with Albert Isidro-Llobet and Mercedes Alvarez) Chemical Reviews 2009 (109) 2455-2504. Examples include, but are not limited to, acyl and acyloxy groups, for example acetyl, chloroacetyl, trichloroacetyl, o-nitrophenylacetyl, o-nitrophenoxy-acetyl, trifluoroacetyl, acetoacetyl, 4-chlorobutyryl, isobutyryl, picolinoyl, aminocaproyl, benzoyl, methoxy-carbonyl, 9-fluorenylmethoxycarbonyl, 2,2,2-trifluoroethoxycarbonyl, 2-trimethylsilylethoxy-carbonyl, tert-butyloxycarbonyl, benzyloxycarbonyl, p-nitrobenzyloxycarbonyl, 2,4-dichloro-benzyloxycarbonyl, and the like. Further examples include Cbz (carboxybenzyl), Nosyl (o- or p-nitrophenylsulfonyl), Bpoc (2-(4-biphenyl)isopropoxycarbonyl) and Dde (1-(4,4-dimethyl-2,6-dioxohexylidene)ethyl).

As used herein, the term "and/or" means "and", or "or", or both.

The term "(s)" following a noun contemplates the singular and plural form, or both.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner. The "containing" is also to be interpreted in the same manner.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9, and 10) and also any range of rational numbers within that range (for example, 2 to 8, 1.5 to 5.5, and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

Although the present invention is broadly as defined above, those persons skilled in the art will appreciate that the invention is not limited thereto and that the invention also includes embodiments of which the following description gives examples.

BRIEF DESCRIPTION OF THE FIGURES

The invention will be described with reference to the accompanying figures in which.

DETAILED DESCRIPTION OF THE INVENTION

Figure 1:
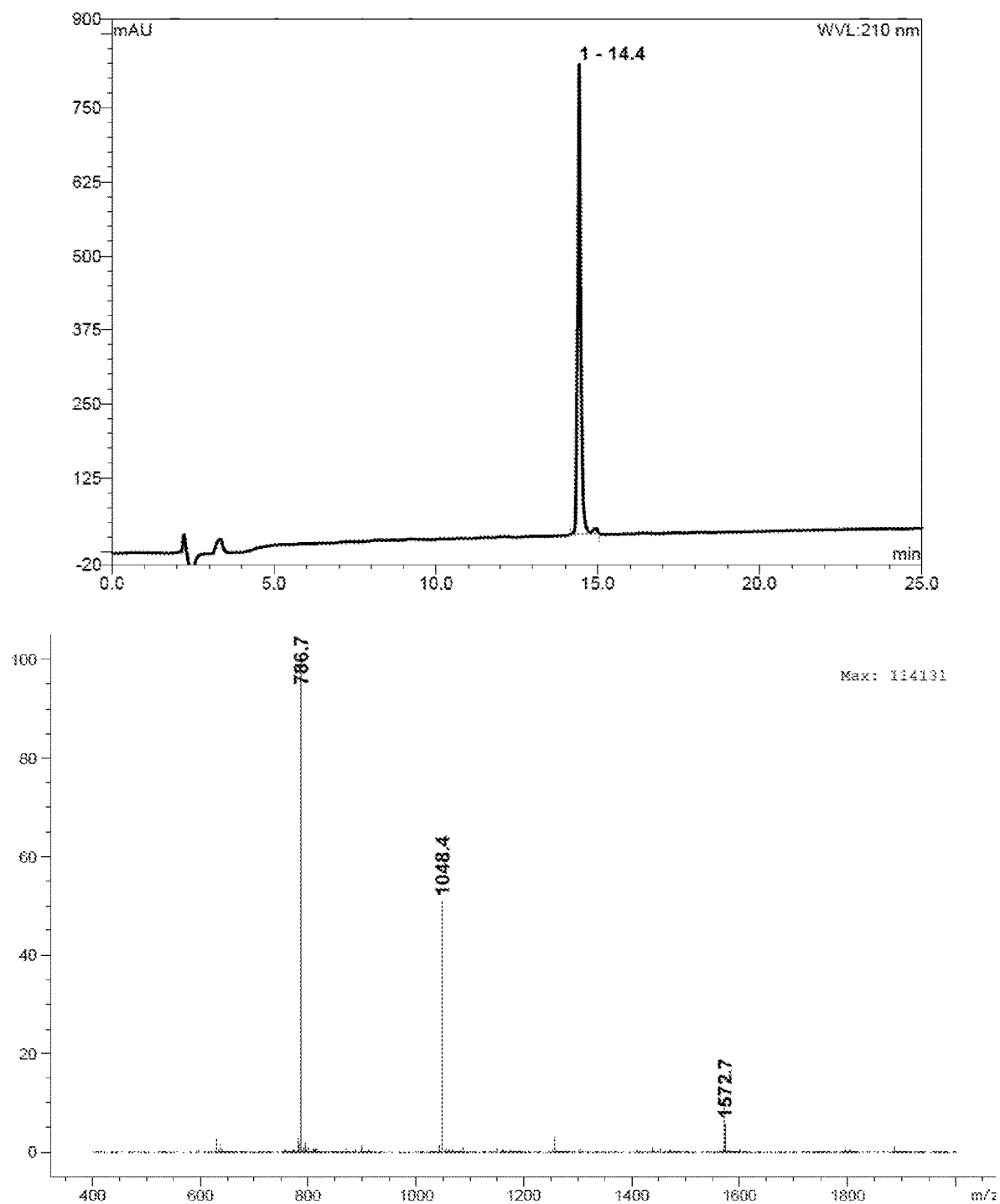
FIG. 1 shows an RP-HPLC trace of LMP2 S1, as described herein in Example 4.

The present invention relates to amino acid and peptide conjugates, and methods of making peptide conjugates and using the peptides and peptide conjugates in immunotherapeutic treatments, particularly immunotherapeutic treatments of conditions associated with EBV. Particular methods of making the conjugates comprises reacting an lipid-containing conjugation partner and an amino acid-comprising conjugation partner under conditions effective to conjugate the lipid-containing conjugation partner to the amino acid-comprising conjugation partner in a thiol-ene reaction. In some embodiments, the method comprises reacting an lipid-containing conjugation partner and a peptide-containing conjugation partner under conditions effective to conjugate the lipid-containing conjugation partner to the peptide of the peptide-containing conjugation partner in a thiol-ene reaction.

The thiol-ene reaction involves the addition of a thiol across a non-aromatic carbon-carbon double bond (i.e. hydrothiolation of the carbon-carbon double bond). The reaction proceeds via a free radical mechanism. There are three distinct phases in the reaction: initiation, polymerisation or coupling, and termination. Radical generation gives rise to an electrophilic thiyl radical which propagates across the ene group, forming a carbon-centred radical. Chain transfer from an additional thiol molecule then quenches the radical on carbon to give the final product.

In the method the present invention, one conjugation partner comprises the thiol and the other comprises the carbon carbon double bond.

One or more free radicals may be generated in the method of the present invention by any method known in the art. The free radicals may be generated thermally and/or photochemically. One or more free radical initiators may be used to initiate the generation of free radicals. Suitable free radical initiators include thermal initiators and photoinitiators.

Free radicals are generated from thermal initiators by heating. The rate of degradation of the thermal initiator and resulting free radical formation depends on the initiator and the temperature at which the initiator is heated. Higher temperatures generally result in faster decomposition. A person skilled in the art will be able to select an appropriate temperature for heating the initiator without undue experimentation.

Numerous thermal initiators are commercially available. Examples of thermal initiators include but are not limited to tert-amyl peroxybenzoate, 1,1'-azobis(cyclohexanecarbonitrile), 2,2'-azobisisobutyronitrile (AIBN), benzoyl peroxide, tert-butyl hydroperoxide, tert-butyl peracetate, tert-butyl peroxide, tert-butyl peroxybenzoate, tert-butylperoxy isopropyl carbonate, lauroyl peroxide, peracetic acid, and potassium persulfate.

Free radicals may be generated from photoinitiators by irradiation with light. The frequency of light necessary to induce degradation of the photoinitiators and free radical formation depends on the initiator. Many photoinitiators can be initiated with ultraviolet light.

Light of a specific wavelength or wavelength range may be used to selectively irradiate the initiator, where the lipid-containing conjugation partner or amino acid-comprising conjugation partner, for example a peptide-containing conjugation partner, comprises photosensitive groups. In certain embodiments of the method of the present invention, a frequency of about 365 nm is used. Light of this frequency is generally compatible with the side chains of naturally occurring amino acids.

A wide range of photoinitiators are commercially available. Examples of photoinitiators include but are not limited to acetophenone, anisoin, anthraquinone, anthraquinone-2-sulfonic acid, benzil, benzoin, benzoin ethyl ether, benzoin isobutyl ether, benzoin methyl ether, benzophenone, 3,3',4,4'-benzophenonetetracarboxylic dianhydride, 4-benzoylbiphenyl, 2-benzyl-2-(dimethylamino)-4'-morpholinobutyrophenone, 4'-bis(diethylamino)benzophenone, 4,4'-bis(dimethylamino)benzophenone, camphorquinone, 2-chlorothioxanthen-9-one, dibenzosuberenone, 2,2-diethoxyacetophenone, 4,4'-dihydroxybenzophenone, 2,2-dimethoxy-2-phenylacetophenone (DMPA), 4-(dimethylamino)benzophenone, 4,4'-dimethylbenzil, 2,5-dimethylbenzophenone, 3,4-dimethylbenzophenone, 4'-ethoxyacetophenone, 2-ethylanthraquinone, 3'-hydroxyacetophenone, 4'-hydroxyacetophenone, 3-hydroxybenzophenone, 4-hydroxybenzophenone, 1-hydroxycyclohexyl phenyl ketone, 2-hydroxy-2-methylpropiophenone, 2-methylbenzophenone, 3-methylbenzophenone, methybenzoylformate, 2-methyl-4'-(methylthio)-2-morpholinopropiophenone, phenanthrenequinone, 4'-phenoxyacetophenone, and thioxanthen-9-one.

A person skilled in the art will be able to select appropriate free radical initiators for use in the method having regard to, for example, the nature of the lipid-containing conjugation partner, amino acid-comprising conjugation partner, for example a peptide-containing conjugation partner, and any other components present in the reaction mixture. In some embodiments, the initiator is present in the reaction in a stoichiometric ratio relative to the starting material comprising the thiol of from about 20:1 to about 0.05:1, from about 10:1 to about 0.05:1, from about 5:1 to about 0.05:1, from about 3:1 to about 0.5:1.

The lipid-containing conjugation partner and amino acid-comprising conjugation partner, for example a peptide-containing conjugation partner, in the reaction are as defined in any of the embodiments described herein.

The lipid-containing conjugation partner and amino acid-comprising conjugation partner, for example a peptide-containing conjugation partner, may be prepared using known synthetic chemistry techniques (for example, the methods generally described in Louis F Fieser and Mary F, Reagents for Organic Synthesis v. 1-19, Wiley, New York (1967-1999 ed.) or Beilsteins Handbuch der organischen Chemie, 4, Aufl. Ed. Springer-Verlag Berlin, including supplements (also available via the Beilstein online database)) or, in some embodiments, may be commercially available.

Lipid-Containing Conjugation Partner Compounds of the Formula (II)

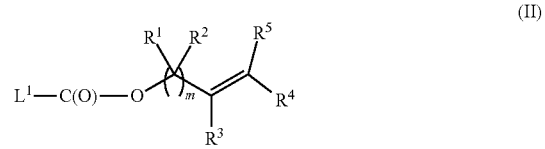

wherein m, R1, R2, R3, R4, R5, and L1 are each independently as defined in any of the embodiments described for the compound of formula (I) may be prepared by reacting a compound of the formula (VI)

wherein X is OH or a suitable leaving group with a compound of the formula (VII):

under conditions effective for esterification. Methods for esterification are well known in the art. For example, when X is chloro, the reaction may be carried out in the presence of a base, such as pyridine or triethylamine, in a suitable solvent. The acid chloride may be converted in situ to a more reactive species (e.g. to the corresponding iodide, using sodium iodide). The temperature at which the reaction is carried out depends on the reactivity of the acid species and the solvent used.

Numerous compounds of formula (VI) are commercially available. Others may be prepared using standard synthetic chemistry techniques from commercially available precursors. For example, compounds of formula (VI) wherein X is chloro may be prepared treating the corresponding carboxylic acid with thionyl chloride in a suitable solvent or mixture of solvents.

Lipid Containing Conjugation Partner Compounds of the Formula (IIA)

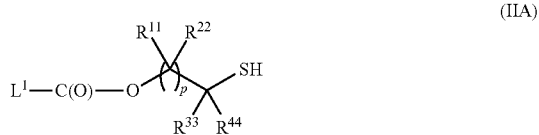
(IIA)

wherein p, R11, R22, R33, R44, and L1 are as defined in the compound of formula (IA) may be prepared by reacting a compound of the formula (VI) as defined above with a compound of the formula (VIII):

(VIII)

wherein P is a suitable protecting group under conditions effective for esterification, and then removing the protecting group.

Alternatively, compounds of the formula (IIA) may be prepared by reacting a compound of the formula (VI) as defined above with a compound of the formula (IX):

(IX)

wherein P is a suitable protecting group under conditions effective for esterification, removing the protecting group, and then converting the corresponding alcohol to a thiol. Suitable methods for converting the alcohol to a thiol will be apparent to those skilled in the art.

Preparation of the compounds may involve the protection and deprotection of various chemical groups. The need for protection and deprotection, and the selection of appropriate protecting groups, can be readily determined by a person skilled in the art.

Protecting groups and methods for protection and deprotection are well known in the art (see e.g. T. W. Greene and P. G. M. Wuts, *Protective Groups in Organic Synthesis*, 3$^{rd}$ Ed., Wiley & Sons, Inc., New York (1999)).

Similarly, compounds of formula (VII), (VIII), and (IX) are also commercially available or may be prepared from commercially available precursors using standard synthetic chemistry techniques.

The order in which the lipid-containing conjugation partner and amino acid-comprising conjugation partner, for example a peptide-containing conjugation partner, and any other components present in the reaction mixture are introduced into the reaction vessel may vary. The reaction may be carried out as a one-pot procedure.

The stoichiometry of the lipid-containing conjugation partner and amino acid-comprising conjugation partner, for example a peptide-containing conjugation partner, in the reaction may vary. In some embodiments, the stoichiometric ratio of amino acid-comprising conjugation partner to lipid-containing conjugation partner is from about 1:0.5 to about 1:20, from about 1:1 to about 1:10, from about 1:1 to about 1:5, from about 1:1 to about 1:3. In some embodiments, the stoichiometric ratio of peptide-containing conjugation partner to lipid-containing conjugation partner is from about 1:0.5 to about 1:20, from about 1:1 to about 1:10, from about 1:1 to about 1:5, from about 1:1 to about 1:3.

The reaction may be carried out at any suitable temperature. In some embodiments, the reaction is carried out at a temperature from about −25° C. to about 200° C., from about −10° C. to about 150° C., from about 0° C. to about 125° C., from about ambient temperature to about 100° C. In some embodiments, the reaction is carried out at a temperature of less than about 200° C., less than about 175° C., less than about 150° C., less than about 125° C., or less than about 100° C.

In some embodiments, the reaction is carried out at a temperature above ambient temperature. In one embodiment, the reaction is carried out at a temperature from 40 to 200° C., from 50 to 150° C., from 60 to 100° C., from 65 to 90° C., or from 70 to 80° C. In some embodiments, the reaction is carried out at a temperature greater than 40° C., greater than 50° C., greater than 75° C., greater than 100° C., or greater than 150° C.

The temperature at which the reaction is carried out may depend on how free radicals are generated in the reaction. The temperature used may be selected to control the rate of the reaction. The temperature may be adjusted during the course of the reaction to control the rate of the reaction. By controlling the rate of the reaction it may be possible to minimise or obviate the formation of undesirable by products (e.g. telomerisation or polymerisation products).

If free radicals are generated thermally (e.g. using a thermal initiator), the reaction will generally be carried out at a temperature above ambient temperature. The temperature will depend on the reactivity of the species from which free radicals are generated.

If free radicals are generated photochemically the reaction may be carried out, advantageously, at ambient temperature. In certain embodiments, it may be desirable to cool the reaction mixture to slow the rate of reaction or conversely heat the reaction mixture to increase the rate of reaction.

A person skilled in the art will be able to select appropriate temperatures for carrying out the method having regard to the reactivity of the lipid-containing conjugation partner, amino acid-comprising conjugation partner, for example a peptide-containing conjugation partner, and free radical initiator if used.

The temperature at which the reaction is carried out may be controlled by heating or cooling the reaction mixture. The temperature of the reaction mixture may be controlled by suitable method known in the art. Heat may be applied to the reaction mixture, for example, using a heat exchanger within the reaction vessel, a heating jacket surrounding the reaction vessel, or by immersing the reaction vessel in a heated liquid (e.g. an oil or sand bath). In certain exemplary embodiments, the reaction mixture is heated by microwave irradiation.

The progress of the reaction may be monitored by any suitable means, for example, by thin layer chromatography (TLC) or high performance liquid chromatography (HPLC). The reaction may be allowed to proceed to substantial completion, as monitored by the consumption of at least one of the starting materials. In some embodiments, the reaction is allowed to proceed for a period of time from 1 minute to 7 days, 5 minutes to 72 hours, 10 minutes to 48 hours, 10 minutes to 24 hours. In other embodiments, the reaction is allowed to proceed for a period of time less than 72 h, less than 48 h, less than 24 h, less than 12 h, less than 6 h, less than 4 h, less than 2 h, or less than 1 h.

In some embodiments, the reaction is carried out until at least about 50%, at least about 60%, at least about 70%, at least about 75%, at least about 80%, at least about 85%, at least about 90%, at least about 95%, at least about 97%, at least about 99% of the lipid-containing conjugation partner or amino acid-comprising conjugation partner, whichever is stoichiometrically less, has been consumed. In some embodiments, the reaction is carried out until at least about 50%, at least about 60%, at least about 70%, at least about 75%, at least about 80%, at least about 85%, at least about 90%, at least about 95%, at least about 97%, at least about 99% of the lipid-containing conjugation partner or peptide-containing conjugation partner, whichever is stoichiometrically less, has been consumed. The consumption of starting materials may be monitored by any suitable method, for example, HPLC.

The reaction mixture may be mixed by any suitable method known in the art, for example, using a magnetic or mechanical stirrer. The method used may depend on the scale on which the reaction is carried out.

The reaction is generally carried out in a liquid reaction medium. The liquid reaction medium may comprise a solvent. Examples of suitable solvents include dimethylformamide, dichloromethane, 1,2-dichloroethane, chloroform, carbon tetrachloride, water, methanol, ethanol, dimethylsulfoxide, trifluoroacetic acid, acetic acid, acetonitrile, and mixtures thereof.

The solvent may be selected based on the solubility of the lipid-containing conjugation partner and amino acid-comprising conjugation partner, for example a peptide-containing conjugation partner, in the solvent. The solubility of the free radical initiator may also be relevant. In some embodiments, the lipid-containing conjugation partner is hydrophobic. The hydrophobicity or hydrophilicity of an amino acid-comprising conjugation partner, for example a peptide-containing conjugation partner, may vary depending on, for example, amino acid sequence of the peptide of a peptide-containing conjugation partner. The presence of a solubilising group in the peptide-containing conjugation partner may increase solubility in polar solvents, such as water. A person skilled in the art will be able to select an appropriate solvent without undue experimentation.

The reaction may be carried out under substantially oxygen-free conditions. Oxygen may quench free radicals formed in the reaction. The reaction mixture may be degassed with an inert gas (e.g. nitrogen or argon) that is substantially oxygen-free to remove any dissolved oxygen before free radicals are generated. Alternatively, individual components of the reaction mixture may be degassed with inert gas that is substantially oxygen-free prior to being combined in the reaction vessel. The reaction may be carried out under an atmosphere of inert gas that is substantially oxygen-free.

The method of the present invention may be carried out at ambient pressure.

If the rate of chain transfer relative to propagation in the thiol-ene reaction is slow, undesirable dimerisation, telomerisation, or polymerisation may occur.

An additive that inhibits dimerisation, telomerisation, or polymerisation may be included in the reaction mixture in the method of the present invention. The inventors have found that in some embodiments the inclusion of an extraneous thiol that facilitates chain transfer as an additive in the reaction mixture reduces the formation of undesirable by products. The extraneous thiol may, in some embodiments, increase the efficiency of the desired thiol ene reaction. Examples of suitable extraneous thiols include but are not limited to reduced glutathione, DODT, DTT, protein, and the like. The inventors have found that in some embodiments the inclusion of DTT resulted in no undesirable by products.

In certain embodiments, the extraneous thiol is a sterically hindered thiol. Non-limiting examples of a suitable sterically hindered extraneous thiol include tert-butyl mercaptan and 1-methylpropyl mercaptan.

The inclusion of an acid in some embodiments may also inhibit dimerisation, telomerisation, or polymerisation. The acid may be a strong inorganic acid, for example HCl, or organic acid, for example TFA. In certain embodiments, the additive is TFA.

The inventors have found that in some embodiments including both tert-butyl mercaptan and TFA as additives in the reaction mixture can reduce the the formation of oligomers, and increase the conversion of starting material to the desired product. Accordingly, in certain exemplary embodiments, the reaction mixture comprises a combination of TFA and tert-butyl mercaptan.

The additive is generally used in an amount sufficient to minimise the formation of undesirable by products without adversely affecting the reaction or any, optional, subsequent steps in the method. In some embodiments, the additive is present in the reaction a stoichiometric ratio relative to the starting material comprising the thiol of from about 20:1 to about 0.05:1, from about 10:1 to about 0.5:1, from about 5:1 to about 1:1, from about 3:1 to about 1:1.

In some embodiments, less than about 50%, less than about 40%, less than about 30%, less than about 25%, less than about 20%, less than about 15%, less than about 10%, less than about 5%, less than about 3%, or less than about 1% by weight of the lipid-containing conjugation partner and amino acid-comprising conjugation partner starting materials used in the reaction are undesirable by products resulting from dimerisation, telomerisation, or polymerisation. In some embodiments, less than about 50%, less than about 40%, less than about 30%, less than about 25%, less than about 20%, less than about 15%, less than about 10%, less than about 5%, less than about 3%, or less than about 1% by weight of the lipid-containing conjugation partner and peptide-containing conjugation partner starting materials used in the reaction are undesirable by products resulting from dimerisation, telomerisation, or polymerisation. The purity of the products of the reaction may be determined by, for example, HPLC.

The concentration of the lipid-containing conjugation partner and amino acid-comprising conjugation partner, for example a peptide-containing conjugation partner, respectively, in the reaction mixture may also affect the reaction. Those skilled in the art will be able to vary the concentration of the lipid-containing conjugation partner and peptide-containing conjugation partner in the reaction mixture to e.g. optimise yield and purity without undue experimentation.

In some embodiments, the starting material comprising the thiol is present in a concentration from about 0.05 mM to about 1 M, from about 0.5 mM to about 1 M, from about 1 mM to about 1 M. In some embodiments, the concentration is at least about 0.05 mM, 0.5 mM, or 1 mM.

In some embodiments, the concentration of the starting material comprising the alkene is at least about 0.05 mM, 0.5 mM, or 1 mM.

In some embodiments, the amino acid conjugate or peptide conjugate may be separated from the reaction medium after the reaction and optionally purified. In some embodiments, the peptide conjugate may be separated from the reaction medium after the reaction and optionally purified. The conjugate may be separated from the reaction medium using any suitable method known in the art, for example, by precipitation.

In some embodiments, the amino acid or peptide conjugate is purified after separating it from the reaction medium. In some embodiments, the peptide conjugate is purified after separating it from the reaction medium. In specifically contemplated embodiments, the conjugate is purified by HPLC using one or more suitable solvents.

The peptide conjugate produced by and/or the peptide-containing conjugation partner in the method of the present invention may comprise a synthetic peptide. Synthetic peptides may be prepared using solid phase peptide synthesis (SPPS).

The basic principle for solid phase peptide synthesis (SPPS) is a stepwise addition of amino acids to a growing polypeptide chain anchored via a linker molecule to a solid phase support, typically a resin particle, which allows for cleavage and purification once the polypeptide chain is complete. Briefly, a solid phase resin support and a starting amino acid are attached to one another via a linker molecule. Such resin-linker-acid matrices are commercially available.

The amino acid to be coupled to the resin is protected at its Nα-terminus by a chemical protecting group.

The amino acid may also have a side-chain protecting group. Such protecting groups prevent undesired or deleterious reactions from taking place during the process of forming the new peptide bond between the carboxyl group of the amino acid to be coupled and the unprotected Nα-amino group of the peptide chain attached to the resin.

The amino acid to be coupled is reacted with the unprotected Nα-amino group of the N-terminal amino acid of the peptide chain, increasing the chain length of the peptide chain by one amino acid. The carboxyl group of the amino acid to be coupled may be activated with a suitable chemical activating agent to promote reaction with the Nα-amino group of the peptide chain. The Nα-protecting group of N-terminal amino acid of the peptide chain is then removed in preparation for coupling with the next amino acid residue. This technique consists of many repetitive steps making automation attractive whenever possible. Those skilled in the art will appreciate that peptides may be coupled to the Nα-amino group of the solid phase bound amino acid or peptide instead of an individual amino acid, for example where a convergent peptide synthesis is desired.

When the desired sequence of amino acids is achieved, the peptide is cleaved from the solid phase support at the linker molecule.

SPPS may be carried out using a continuous flow method or a batch flow method. Continuous flow permits real-time monitoring of reaction progress via a spectrophotometer, but has two distinct disadvantages—the reagents in contact with the peptide on the resin are diluted, and scale is more limited due to physical size constraints of the solid phase resin. Batch flow occurs in a filter reaction vessel and is useful because reactants are accessible and can be added manually or automatically.

The types of protecting groups are commonly used for protecting the N-alpha-amino terminus: "Boc" (tert-butyloxycarbonyl) and "Fmoc" (9-fluorenylmethyloxycarbonyl). Reagents for the Boc method are relatively inexpensive, but they are highly corrosive and require expensive equipment and more rigorous precautions to be taken. The Fmoc method, which uses less corrosive, although more expensive, reagents is typically preferred.

For SPPS, a wide variety of solid support phases are available. The solid phase support used for synthesis can be a synthetic resin, a synthetic polymer film or a silicon or silicate surface (e.g. controlled pore glass) suitable for synthesis purposes. Generally, a resin is used, commonly polystyrene suspensions, or polystyrene-polyethyleneglycol, or polymer supports for example polyamide. Examples of resins functionalized with linkers suitable for Boc-chemistry include PAM resin, oxime resin SS, phenol resin, brominated Wang resin and brominated PPOA resin. Examples of resins suitable for Fmoc chemistry include AMPB-BHA resin, Sieber amide resin, Rink acid resin, Tentagel S AC resin, 2-chlorotrityl chloride resin, 2-chlorotrityl alcohol resin, TentaGel S Trt-OH resin, Knorr-2-chlorotrityl resin, hydrazine-2-chlorotrityl resin, ANP resin, Fmoc photolabile resin, HMBA-MBHA resin, TentaGel S HMB resin, Aromatic Safety Catch resinBAl resin and Fmoc-hydroxylamine 2 chlorotrityl resin. Other resins include PL Cl-Trt resin, PL-Oxime resin and PL-HMBA Resin.

For each resin appropriate coupling conditions are known in the literature for the attachment of the starting monomer or sub-unit.

Preparation of the solid phase support includes solvating the support in an appropriate solvent (e.g. dimethylformamide). The solid phase typically increases in volume during solvation, which in turn increases the surface area available to carry out peptide synthesis.

A linker molecule is then attached to the support for connecting the peptide chain to the solid phase support. Linker molecules are generally designed such that eventual cleavage provides either a free acid or amide at the C-terminus. Linkers are generally not resin-specific. Examples of linkers include peptide acids for example 4-hydroxymethylphenoxyacetyl-4'-methylbenzhydrylamine (HMP), or peptide amides for example benzhydrylamine derivatives.

The first amino acid of the peptide sequence may be attached to the linker after the linker is attached to the solid phase support or attached to the solid phase support using a linker that includes the first amino acid of the peptide sequence. Linkers that include amino acids are commercially available.

The next step is to deprotect the Nα-amino group of the first amino acid. For Fmoc SPPS, deprotection of the Nα-amino group may be carried out with a mild base treatment (piperazine or piperidine, for example). Side-chain protecting groups may be removed by moderate acidolysis (trifluoroacetic acid (TFA), for example). For Boc SPPS, deprotection of the Nα-amino group may be carried out using for example TFA.

Following deprotection, the amino acid chain extension, or coupling, proceeds by the formation of peptide bonds. This process requires activation of the C-α-carboxyl group of the amino acid to be coupled. This may be accomplished using, for example, in situ reagents, preformed symmetrical anhydrides, active esters, acid halides, or urethane-protected N-carboxyanhydrides. The in situ method allows concurrent activation and coupling. Coupling reagents include carbodiimide derivatives, for example N,N'-dicyclohexylcarbodiimide or N,N-diisopropylcarbodiimide. Coupling reagents also include uronium or phosphonium salt derivatives of benzotriazol. Examples of such uronium and phosphonium salts include HBTU (O-1H-benzotriazole-1-yl)-N,N,N',N'-tetramethyluronium hexafluorophosphate), BOP (benzotriazole-1-yl-oxy-tris-(dimethylamino)-phosphonium hexafluorophosphate), PyBOP (Benzotriazole-1-yl-oxytripyrrolidinophosphonium hexafluorophosphate), PyAOP, HCTU (O-(1H-6-chloro-benzotriazole-1-yl)-1,1,3,3-tetramethyluronium hexafluorophosphate), TCTU (O-1H-6-chlorobenzotriazole-1-yl)-1,1,3,3-tetramethyluronium tetrafluoroborate), HATU (O-(7-azabenzotriazol-1-yl)-1,1,3,3-tetramethyluronium hexafluorophosphate), TATU (O-(7-azabenzotriazol-1-yl)-1,1,3,3-tetramethyluronium tetrafluoroborate), TOTU (O-[cyano(ethoxycarbonyl)methyleneamino]-N,N,N',N"-tetramethyluronium tetrafluoroborate), and HAPyU (O-(benzotriazol-1-yl)oxybis-(pyrrolidino)-uronium hexafluorophosphate. In some embodiments, the coupling reagent is HBTU, HATU, BOP, or PyBOP.

After the desired amino acid sequence has been synthesized, the peptide is cleaved from the resin. The conditions used in this process depend on the sensitivity of the amino acid composition of the peptide and the side-chain protecting groups. Generally, cleavage is carried out in an environment containing a plurality of scavenging agents to quench the reactive carbonium ions that originate from the protective groups and linkers. Common cleaving agents include, for example, TFA and hydrogen fluoride (HF). In some embodiments, where the peptide is bound to the solid phase support via a linker, the peptide chain is cleaved from the solid phase support by cleaving the peptide from the linker.

The conditions used for cleaving the peptide from the resin may concomitantly remove one or more side-chain protecting groups.

The use of protective groups in SPPS is well established. Examples of common protective groups include but are not limited to acetamidomethyl (Acm), acetyl (Ac), adamantyloxy (AdaO), benzoyl (Bz), benzyl (Bzl), 2-bromobenzyl, benzyloxy (BzlO), benzyloxycarbonyl (Z), benzyloxymethyl (Bom), 2-bromobenzyloxycarbonyl (2-Br—Z), tert-butoxy (tBuO), tert-butoxycarbonyl (Boc), tert-butoxymethyl (Bum), tert-butyl (tBu), tert-butylthio (tButhio), 2-chlorobenzyloxycarbonyl (2-Cl—Z), cyclohexyloxy (cHxO), 2,6-dichlorobenzyl (2,6-DiCl-Bzl), 4,4'-dimethoxybenzhydryl (Mbh), 1-(4,4-dimethyl-2,6-dioxo-cyclohexylidene) 3-methyl-butyl (ivDde), 4-{N-[1-(4,4-dimethyl-2,6-dioxo-cyclohexylidene)3-methylbutyl]-amino} benzyloxy (ODmab), 2,4-dinitrophenyl (Dnp), fluorenylmethoxycarbonyl (Fmoc), formyl (For), mesitylene-2-sulfonyl (Mts), 4-methoxybenzyl (MeOBzl), 4-methoxy-2,3,6-trimethyl-benzenesulfonyl (Mtr), 4-methoxytrityl (Mmt), 4-methylbenzyl (MeBzl), 4-methyltrityl (Mtt), 3-nitro-2-pyridinesulfenyl (Npys), 2,2,4,6,7-pentamethyldihydrobenzofurane-5-sulfonyl (Pbf), 2,2,5,7,8-pentamethyl-chromane-6-sulfonyl (Pmc), tosyl (Tos), trifluoroacetyl (Tfa), trimethylacetamidomethyl (Tacm), trityl (Trt) and xanthyl (Xan).

Where one or more of the side chains of the amino acids of the peptide contains functional groups, such as for example additional carboxylic, amino, hydroxy or thiol groups, additional protective groups may be necessary. For example, if the Fmoc strategy is used, Mtr, Pmc, Pbf may be used for the protection of Arg; Trt, Tmob may be used for the protection of Asn and Gln; Boc may be used for the protection of Trp and Lys; tBu may be used for the protection of Asp, Glu, Ser, Thr and Tyr; and Acm, tBu, tButhio, Trt and Mmt may be used for the protection of Cys. A person skilled in the art will appreciate that there are numerous other suitable combinations.

The methods for SPPS outlined above are well known in the art. See, for example, Atherton and Sheppard, "Solid Phase Peptide Synthesis: A Practical Approach," New York: IRL Press, 1989; Stewart and Young: "Solid-Phase Peptide Synthesis 2nd Ed.," Rockford, Ill.: Pierce Chemical Co., 1984; Jones, "The Chemical Synthesis of Peptides," Oxford: Clarendon Press, 1994; Merrifield, *J. Am. Soc.* 85:2146-2149 (1963); Marglin, A. and Merrifield, R. B. *Annu. Rev. Biochem.* 39:841-66 (1970); and Merrifield R. B. JAMA. 210(7):1247-54 (1969); and "Solid Phase Peptide Synthesis—A Practical Approach" (W. C. Chan and P. D. White, eds. Oxford University Press, 2000). Equipment for automated synthesis of peptides or polypeptides is readily commercially available from suppliers such as Perkin Elmer/Applied Biosystems (Foster City, Calif.) and may be operated according to the manufacturer's instructions.

Following cleavage from the resin, the peptide may be separated from the reaction medium, e.g. by centrifugation or filtration. The peptide may then be subsequently purified, e.g. by HPLC using one or more suitable solvents.

Advantageously, the inventors have found that in some embodiments the peptide-containing conjugation partner may be used in the method of the present invention without purification following cleavage of the peptide from the resin.

The inventors have also advantageously found that the method of the present invention can be carried out using a peptide-containing conjugation partner, wherein the peptide does not contain an Nα-amino group protecting group or any side chain protecting groups. The reaction is generally selective for reaction of a thiol and a non-aromatic carbon-carbon double bond.

It may be necessary to protect thiol groups present in the peptide-containing conjugation partner (e.g. in cysteine residues of the peptide) with a protective group to prevent undesirable competing reactions in the method of the present invention. The thiol groups may be protected with a protective group that is not removable under the conditions used to remove one or more other protecting groups present in the peptide or to cleave the peptide from the resin. Typically, the peptide will be synthesised using amino acids bearing the appropriate protecting groups. A person skilled in the art will be able to select appropriate protecting groups without undue experimentation.

In certain embodiments, the amino acid-comprising conjugation partner and lipid-containing conjugation partner comprise one or more unsaturated carbon-carbon bonds in addition to the carbon-carbon double bond to be reacted. In certain embodiments, the peptide-containing conjugation partner and lipid-containing conjugation partner comprise one or more unsaturated carbon-carbon bonds in addition to the carbon-carbon double bond to be reacted. Those skilled in the art will appreciate that the selectivity of the thiol for the carbon-carbon double bond to be reacted in such embodiments may depend on, for example, the steric and/or electronic environment of the carbon-carbon double bond relative to the one or more unsaturated carbon-carbon bonds. In certain embodiments, the carbon-carbon double bond to be reacted is activated relative to any other unsaturated carbon-carbon bonds in the amino acid-comprising conjugation partner and lipid-containing conjugation partner. In certain embodiments, the carbon-carbon double bond to be reacted is activated relative to any other unsaturated carbon-carbon bonds in the peptide-containing conjugation partner and lipid-containing conjugation partner.

In some embodiments, the Nα-amino group of the amino acid of the amino acid-comprising conjugation partner comprising the carbon-carbon double bond or thiol is acylated, for example acetylated. In some embodiments, the method of the present invention may comprise acylating, for example acetylating, the Nα-amino group of the amino acid of the amino acid-comprising conjugation partner comprising the carbon-carbon double bond or thiol to be reacted.

Where a peptide-containing conjugation partner has been synthesised by SPPS, acylation may be carried out prior to or after cleavage from the resin. In some embodiments, the amino acid residue of the peptide-containing conjugation partner bearing the carbon-carbon double bond or thiol to be reacted is an N-terminal amino acid residue, and the method comprises acylating the N-terminal amino group prior to cleaving the peptide.

In some embodiments, the method further comprises acylating the Nα-amino group of the amino acid of the amino acid conjugate or the amino acid residue of the peptide conjugate to which the lipid-containing conjugation partner is conjugated.

Acylation of the Nα-amino group of an amino acid may be carried out by reacting an amino acid or peptide with an acylating agent in the presence of base in a suitable solvent, for example DMF. Non-limiting examples of acylating agents include acid halides, for example acid chlorides such as acetyl chloride, and acid anhydrides, for example acetic anhydride. Such agents maybe commercially available or may be prepared by methods well known in the art. Non-limiting examples of suitable bases include triethylamine, diisopropylethylamine, 4-methylmorpholine, and the like.

In other embodiments, the synthesising the peptide of the peptide-containing conjugation partner comprises coupling an amino acid or a peptide comprising an amino acid that is acylated at the Nα-amino group and comprises the carbon-carbon double bond or thiol to be reacted to one or more amino acids and/or one or more peptides.

In some embodiments, the method comprises coupling the amino acid of the amino acid conjugate to an amino acid or a peptide to provide a peptide conjugate. In some embodiments, the method comprises coupling the amino acid of the amino acid conjugate to an amino acid or peptide bound to a solid phase resin support by SPPS. In some embodiments, the method comprises coupling the amino acid conjugate to a peptide bound to a solid phase resin support by SPPS. The method may comprise synthesising the peptide bound to the solid phase resin support by SPPS.

In some embodiments, the method further comprises coupling the amino acid of the amino acid conjugate or an amino acid of the peptide conjugate to one or more amino acids or peptides so as to provide a peptide conjugate comprising one or more EBV LMP2 epitopes. In some embodiments, the peptide to be coupled comprises one or more EBV LMP2 epitopes. In other embodiments, one or more EBV LMP2 epitopes is formed on coupling. The coupling may be carried out by SPPS as described herein.

In some embodiments, the method comprises coupling the amino acid of the amino acid conjugate to a peptide bound to a solid phase resin support by SPPS so as to provide a peptide conjugate comprising one or more EBV LMP2 epitopes.

In one embodiment, the peptide of the peptide conjugate to be coupled is bound to a solid phase resin support, and the method comprises coupling an amino acid of the peptide conjugate to be coupled to an amino acid or a peptide so as to provide a peptide conjugate comprising one or more EBV LMP2 epitopes.

In an alternate embodiment, the method comprises coupling an amino acid of the peptide conjugate to an amino acid or peptide bound to a solid phase resin support by SPPS so as to provide peptide conjugate comprising a peptide epitope.

In some embodiments, the method further comprises coupling an epitope, for example a peptide epitope, to the amino acid conjugate or peptide conjugate. Where the method comprises coupling a peptide epitope, the coupling may be carried out by SPPS as described herein.

In certain embodiments, the epitope, for example one or more EBV LMP2 epitopes, is coupled or bound via a linker group. In certain embodiments, the linker group is an amino sequence, for example a sequence of two or more, three or more, or four or more contiguous amino acids. In certain embodiments, the linker comprises from about 2 to 20, 2 to 18, 2 to 16, 2 to 14, 2 to 12, 2 to 10, 4 to 20, 4 to 18, 4 to 16, 4 to 14, 4 to 12, or 4 to 10 amino acids.

It will be appreciate by those skilled in the art that coupling an amino acid or a peptide to another amino acid or peptide as described herein may comprise forming a peptide bond between the Nα-terminus of the amino acid or an amino acid of the peptide of one coupling partner and the C-terminus of the amino acid or an amino acid of the peptide of the other coupling partner.

In some embodiments, the method of the present invention comprises synthesising the amino acid sequence of the peptide of the peptide-containing conjugation partner by SPPS; and reacting the lipid-containing conjugation partner with the peptide-containing conjugation partner.

In some embodiments, synthesising the amino acid sequence of the peptide of the peptide-containing conjugation partner by SPPS comprises coupling an amino acid or peptide to an amino acid or peptide bound to a solid phase resin support to provide the amino acid sequence of the peptide or a portion thereof. In certain embodiments, the amino acid sequence of the entire peptide of the peptide-containing conjugation partner is synthesised by SPPS.

The peptide-containing conjugation partner may be reacted with the lipid-containing conjugation partner while bound to a solid phase resin support. Alternatively, the peptide may be cleaved from the solid phase resin support, and optionally purified, prior to reaction with the lipid-containing conjugation partner.

The peptide conjugate and/or amino acid-comprising conjugation partner, for example a peptide-containing conjugation partner, may comprise one or more solubilising groups.

The one or more solubilising groups increase the solubility of, for example, the peptide-containing conjugation partner in polar solvents, such as water. In exemplary embodiments, the solubilising group does not adversely affect the biological activity of the peptide conjugate.

The presence of a solubilising group may be advantageous for formulation and/or administration of the peptide conjugate as a pharmaceutical composition.

In some embodiments, the solubilising group is bound to the peptide of the peptide conjugate and/or peptide-containing conjugation partner. In some embodiments, the solubilising group is bound to the peptide of the peptide-containing conjugation partner. In some embodiments, the peptide of the peptide conjugate and/or the peptide of the peptide-containing partner comprises a solubilising group. In some embodiments, the peptide of the peptide-containing partner comprises a solubilising group.

In some embodiments, the solubilising group is bound to the side chain of an amino acid in the peptide chain. In some embodiments, the solubilising group is bound to the C- or N-terminus of the peptide chain. In some embodiments, the solubilising group is bound between two amino acid residues in the peptide chain. In some embodiments, the solubilising group is bound to the Nα-amino group of one amino acid residue in the peptide chain and the carboxyl group of another amino acid residue in the peptide chain.

Examples of suitable solubilising groups include, but are not limited to, hydrophilic amino acid sequences or polyethylene glycols (PEGs).

In one embodiment, the solubilising group is a hydrophilic amino acid sequence comprising two or more hydrophilic amino acid residues in the peptide chain. In some embodiments, the solubilising group is an amino acid sequence comprising a sequence of two or more consecutive hydrophilic amino acid residues in the peptide chain. Such solubilising groups may be formed by adding each amino acid of the solubilising group to the peptide chain by SPPS.

In another embodiment, the solubilising group is a polyethylene glycol. In some embodiments, the polyethylene glycol is bound to the Nα-amino group of one amino acid residue in the peptide chain and the carboxyl group of another amino acid residue in the peptide chain.

In some embodiments, the polyethylene glycol comprises from about 1 to about 100, about 1 to about 50, about 1 to about 25, about 1 to about 20, about 1 to about 15, about 1 to about 10, about 2 to about 10, or about 2 to about 4 ethylene glycol monomer units. Methods for coupling polyethylene glycols to peptides are known.

In some embodiments, the peptide conjugate and/or peptide-containing conjugation partner comprises an antigen, for example, an antigenic peptide. In one embodiment, the peptide of the peptide conjugate or peptide-containing conjugation partner is or comprises an antigen; or an antigen is bound to peptide, optionally via a linker. In some embodiments, the peptide-containing conjugation partner comprises an antigen, for example, an antigenic peptide. In one embodiment, the peptide of the peptide-containing conjugation partner is or comprises an antigen; or an antigen is bound to peptide, optionally via a linker.

In one embodiment, the antigen comprises a peptide comprising an epitope. In one embodiment, the peptide comprising an epitope is a glycopeptide comprising an epitope. In one embodiment, the antigen comprises a glycopeptide comprising an epitope.

In some embodiments, the peptide conjugate and/or peptide-containing conjugation partner comprises an epitope. In some embodiments, the peptide of the peptide conjugate and/or peptide-containing conjugation partner comprises an epitope. In some embodiments, the peptide-containing conjugation partner comprises an epitope. In some embodiments, the peptide of the peptide-containing conjugation partner comprises an epitope.

In some embodiments, the peptide conjugate and/or peptide-containing conjugation partner comprises two or more EBV LMP2 epitopes, for example, the peptide of the peptide conjugate and/or peptide-containing conjugation partner comprises two or more EBV LMP2 epitopes.

In some embodiments, the peptide conjugate and/or peptide-containing conjugation partner is or comprises a glycopeptide comprising one or more EBV LMP2 epitopes. In some embodiments, the peptide of the peptide conjugate and/or peptide-containing conjugation partner is a glycopeptide. In some embodiments, the peptide conjugate and/or peptide-containing conjugation partner comprises a glycopeptide comprising one or more EBV LMP2 epitopes bound to the peptide of the peptide conjugate and/or peptide-containing conjugation partner. For example, the peptide-containing conjugation partner is or comprises a glycopeptide comprising one or more EBV LMP2 epitopes. In some embodiments, the peptide of the peptide-containing conjugation partner is a glycopeptide. In another example, the peptide-containing conjugation partner comprises a glycopeptide comprising one or more EBV LMP2 epitopes bound to the peptide of the peptide-containing conjugation partner.

In some embodiments, the peptide conjugate and/or peptide-containing conjugation partner comprises a proteolytic cleavage site. In some embodiments, the peptide of the peptide conjugate and/or peptide-containing conjugation partner comprises a proteolytic cleavage site. In some embodiments, the peptide-containing conjugation partner comprises a proteolytic cleavage site. In some embodiments, the peptide of the peptide-containing conjugation partner comprises a proteolytic cleavage site.

In some embodiments, the peptide of the peptide conjugate and/or peptide-containing conjugation partner comprises one or more linker groups. In some embodiments, the peptide of the peptide-containing conjugation partner comprises one or more linker groups.

In some embodiments, the peptide conjugate and/or peptide-containing conjugation partner comprises a linker group. In some embodiments, the peptide-containing conjugation partner comprises a linker group.

In some embodiments, the peptide conjugate and/or peptide-containing conjugation partner comprises an epitope bound to the peptide of the peptide conjugate and/or peptide-containing conjugation partner via a linker group. In some embodiments, the peptide-containing conjugation partner comprises an epitope bound to the peptide of the peptide-containing conjugation partner via a linker group.

Examples of linker groups include but are not limited to amino acid sequences (for example, a peptide), polyethylene glycol, alkyl amino acids, and the like. In some embodiments, the linker is or comprises a proteolytic cleavage site. In some embodiments, the linker is or comprises a solubilising group.

In some embodiments, the linker is bound between two amino acid residues in the peptide chain.

In some embodiments, the linker group is bound to the Nα-amino group of one amino acid residue in the peptide conjugate and/or peptide-containing conjugation partner and the carboxyl group of another amino acid residue in the peptide-containing conjugation partner. In some embodiments, the linker group is bound to the Nα-amino group of one amino acid residue in the peptide-containing conjugation partner and the carboxyl group of another amino acid residue in the peptide-containing conjugation partner.

In certain embodiments, the linker group is cleavable in vivo from the amino acids to which it is bound. In certain embodiments, the linker group is cleavable by hydrolysis in vivo. In certain embodiments, the linker group is cleavable by enzymatic hydrolysis in vivo. Linker groups may be introduced by any suitable method known in the art.

The method may further comprise coupling an epitope to the amino acid of the amino acid conjugate or the peptide of the peptide conjugate. The epitope may be bound via a linker group, as described above. In some embodiments, the epitope is a peptide epitope. In some embodiments, the method comprises coupling a glycopeptide comprising an epitope.

It will be appreciated that in certain desirable embodiments, the peptide conjugates of the invention maintain appropriate uptake, processing, and presentation by antigen presenting cells. Desirably, the lipid-containing conjugate does not interfere with presentation of any antigenic peptide present in the conjugate by antigen presenting cells. The examples presented herein establish that conjugates of the invention are presented by antigen presenting cells comparably with non-conjugated, related peptides.

Confirmation of the identity of the peptides synthesized may be conveniently achieved by, for example, amino acid analysis, mass spectrometry, Edman degradation, and the like.

The method of the present invention may further comprise separating the amino acid conjugate from the liquid reaction medium. Alternatively, the method of the present invention may further comprise separating the peptide conjugate from the liquid reaction medium. Any suitable separation methods known in the art may be used, for example, precipitation and filtration. The conjugate may be subsequently purified, for example, by HPLC using one or more suitable solvents.

The present invention also relates to amino acid conjugates and peptide conjugates made by the method of the present invention. The conjugates are as defined in any of the embodiments described herein.

The present invention also relates to a compound of the formula (V), which is an amino acid conjugate.

The present invention also relates to a compound of the formula (V), which is a peptide conjugate.

The peptide conjugates may be pure or purified, or substantially pure.

As used herein "purified" does not require absolute purity; rather, it is intended as a relative term where the material in question is more pure than in the environment it was in previously. In practice the material has typically, for example, been subjected to fractionation to remove various other components, and the resultant material has substantially retained its desired biological activity or activities. The term "substantially purified" refers to materials that are at least about 60% free, preferably at least about 75% free, and most preferably at least about 90% free, at least about 95% free, at least about 98% free, or more, from other components with which they may be associated during manufacture.

The term "α-amino acid" or "amino acid" refers to a molecule containing both an amino group and a carboxyl group bound to a carbon which is designated the α-carbon. Suitable amino acids include, without limitation, both the D- and L-isomers of the naturally-occurring amino acids, as well as non-naturally occurring amino acids prepared by organic synthesis or other metabolic routes. Unless the context specifically indicates otherwise, the term amino acid, as used herein, is intended to include amino acid analogs.

In certain embodiments the peptide-containing conjugation partner comprises only natural amino acids. The term "naturally occurring amino acid" refers to any one of the twenty amino acids commonly found in peptides synthesized in nature, and known by the one letter abbreviations A, R, N, C, D, Q, E, G, H, I, L, K, M, F, P, S, T, W, Y and V.

The term "amino acid analog" or "non-naturally occurring amino acid" refers to a molecule which is structurally similar to an amino acid and which can be substituted for an amino acid. Amino acid analogs include, without limitation, compounds which are structurally identical to an amino acid, as defined herein, except for the inclusion of one or more additional methylene groups between the amino and carboxyl group (e.g., a-amino O-carboxy acids), or for the substitution of the amino or carboxy group by a similarly reactive group (e.g., substitution of the primary amine with a secondary or tertiary amine, or substitution or the carboxy group with an ester).

Unless otherwise indicated, conventional techniques of molecular biology, microbiology, cell biology, biochemistry and immunology, which are within the skill of the art may be employed in practicing the methods described herein. Such techniques are explained fully in the literature, such as, Molecular Cloning: A Laboratory Manual, second edition (Sambrook et al., 1989); Oligonucleotide Synthesis (M. J. Gait, ed., 1984); Animal Cell Culture (R. I. Freshney, ed., 1987); Handbook of Experimental Immunology (D. M. Weir & C. C. Blackwell, eds.); Gene Transfer Vectors for Mammalian Cells (J. M. Miller & M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); The Immunoassay Handbook (David Wild, ed., Stockton Press NY, 1994); Antibodies: A Laboratory Manual (Harlow et al., eds., 1987); and Methods of Immunological Analysis (R. Masseyeff, W. H. Albert, and N. A. Staines, eds., Weinheim: VCH Verlagsgesellschaft mbH, 1993).

The term "peptide" and the like is used herein to refer to any polymer of amino acid residues of any length. The polymer can be linear or non-linear (e.g., branched), it can comprise modified amino acids or amino acid analogs. The term also encompasses amino acid polymers that have been modified naturally or by intervention, for example, by disulfide bond formation, glycosylation, lipidation, acetylation, phosphorylation, or any other modification or manipulation, for example conjugation with labeling or bioactive component.

The inventors have found that the certain peptide conjugates of the present invention have immunological activity.

Cell-mediated immunity is primarily mediated by T-lymphocytes. Pathogenic antigens are expressed on the surface of antigen presenting cells (such as macrophages, B-lymphocytes, and dendritic cells), bound to either major histocompatibility MHC Class I or MHC Class II molecules. Presentation of pathogenic antigen coupled to MHC Class II activates a helper (CD4+) T-cell response. Upon binding of the T-cell to the antigen-MHC II complex, CD4+ T-cells, release cytokines and proliferate.

Presentation of pathogenic antigens bound to MHC Class I molecules activates a cytotoxic (CD8+) T-cell response. Upon binding of the T-cell to the antigen-MHC I complex, CD8+ cells secrete perforin and other mediators, resulting in target cell death. Without wishing to be bound by any theory, the applicants believe that in certain embodiments an enhanced response by CD8+ cells is achieved in the presence of one or more epitopes recognised by CD4+ cells.

Methods to assess and monitor the onset or progression of a cell-mediated response in a subject are well known in the art. Convenient exemplary methods include those in which the presence of or the level of one or more cytokines associated with a cell-mediated response, such as those identified herein, is assessed. Similarly, cell-based methods to assess or monitor the onset and progression of a cell-mediated response are amenable to use in the present invention, and may include cell proliferation or activation assays, including assays targeted at identifying activation or expansion of one or more populations of immune cells, such as T-lymphocytes.

In certain embodiments, methods of the invention elicit both a cell-mediated immune response and a humoral response.

The humoral immune response is mediated by secreted antibodies produced by B cells. The secreted antibodies bind to antigens presented on the surface of invading pathogens, flagging them for destruction.

Again, methods to assess and monitor the onset or progression of a humoral response are well known in the art. These include antibody binding assays, ELISA, skin-prick tests and the like.

Without wishing to be bound by theory, the inventors believe that the peptide conjugates in some embodiments stimulate Toll like receptors (TLRs).

Toll-like receptors (TLRs) are highly conserved pattern recognition receptors (PRRs) that recognise pathogen-associated molecular patterns and transmit danger signals to the cell (Kawai, T., Akira, S., *Immunity* 2011, 34, 637-650). TLR2 is a cell-surface receptor expressed on a range of different cell types, including dendritic cells, macrophages and lymphocytes (Coffman, R. L., Sher, A., Seder, R. A., *Immunity* 2010, 33, 492-503).

TLR2 recognises a wide range of microbial components including lipopolysaccharides, peptidoglycans and lipoteichoic acid. It is unique amongst TLRs in that it forms heterodimers, with either TLR1 or TLR6; the ability to form complexes with other PRRs may explain the wide range of agonists for TLR2 (Feldmann, M., Steinman, L., *Nature* 2005, 435, 612-619). Upon ligand binding and heterodimerisation, signalling takes place via the MyD88 pathway, leading to NFκB activation and consequent production of inflammatory and effector cytokines.

Di- and triacylated lipopeptides derived from bacterial cell-wall components have been extensively studied as TLR2 agonists (Eriksson, E. M. Y., Jackson, D. C., *Curr. Prot. and Pept. Sci.* 2007, 8, 412-417). Lipopeptides have been reported to promote dendritic cell maturation, causing the up-regulation of co-stimulatory molecules on the cell surface and enhanced antigen-presentation. Lipopeptides have also been reported to stimulate macrophages to release cytokines and promote the activation of lymphocytes including B cells and CD8+ T cells.

In some embodiments, the peptide conjugate has TLR2 agonist activity. In some embodiments, the peptide conjugate has TLR2 agonist activity comparable to Pam3CSK4. In some embodiments, the peptide conjugate has TLR2 agonist activity at least about 50%, about 60%, about 70%, about 80%, about 90% that of Pam3CSK4. In some embodiments, for example in embodiments where a modulated immune response is desirable, the peptide conjugate has TLR2 agonist activity less that that of Pam3CSK4. For example, the peptide conjugate has TLR2 agonist activity less than about 50%, less than about 40%, less than about 30%, less than about 20%, or less than about 10% that of Pam3CSK4.

In some embodiments, the peptide of the peptide conjugate and/or peptide-containing conjugation partner comprises a serine amino acid residue adjacent to the amino acid through which the lipid-containing conjugation partner is conjugated to the peptide. In some embodiments, the peptide of the peptide-containing conjugation partner comprises a serine amino acid residue adjacent to the amino acid through which the lipid-containing conjugation partner is conjugated to the peptide. The presence of the serine amino acid residue in this position may enhance TLR2 binding. In some embodiments, the serine amino acid residue is bound to the C-termini of the amino acid through which the lipid-containing conjugation partner is conjugated to the peptide.

As will be appreciated by those skilled in the art on reading this disclosure, the peptide conjugate may comprise an epitope, including, for example two or more epitopes. In some embodiments, the epitope is a peptide epitope. A person skilled in the art will appreciate that a wide range of peptide epitopes may be employed in the present invention.

Antigens

It will be appreciated that a great many antigens, for example tumour antigens or antigens from various pathogenic organisms, have been characterised and are suitable for use in the present invention, for example in combination with compositions, vaccines and conjugates comprising the EBV LMP2 epitopes and peptides specifically recited herein. All antigens, whether or not presently characterized, that are capable of eliciting an immune response are contemplated.

The peptides and conjugates of the present invention find application in a wide range of immunotherapies, including but not limited to the treatment and prevention of conditions or diseases associated with EBV, including but not limited to the treatment and prevention of cancer and neoplastic conditions including Hodgkin's disease, non-Hodgkin's lymphoma, lymphomas, and lymphoepitheliomas including NPC, and the treatment of viral re-activation during or following immunosuppression, for example in patients who have had bone marrow transplants or haematopoietic stem cell transplants.

Also contemplated are antigens, particularly EBV LMP2 peptide antigens, comprising one or more amino acid substitutions, such as one or more conservative amino acid substitutions.

A "conservative amino acid substitution" is one in which an amino acid residue is replaced with another residue having a chemically similar or derivatised side chain. Families of amino acid residues having similar side chains, for example, have been defined in the art. These families include, for example, amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid analogs (e.g., phosphorylated or glycosylated amino acids) are also contemplated in the present invention, as are peptides substituted with non-naturally occurring amino acids, including but not limited to N-alkylated amino acids (e.g. N-methyl amino acids), D-amino acids, 1-amino acids, and γ-amino acids.

Fragments and variants of antigens are also specifically contemplated.

A "fragment" of a peptide, is a subsequence of the peptide that performs a function that is required for the enzymatic or binding activity and/or provides three dimensional structure of the peptide, such as the three dimensional structure of a polypeptide.

The term "variant" as used herein refers to peptide sequences, including for example peptide sequences different from the specifically identified sequences, wherein one or more amino acid residues is deleted, substituted, or added. Variants are naturally-occurring variants, or non-naturally occurring variants. Variants are from the same or from other species and may encompass homologues, paralogues and orthologues. In certain embodiments, variants of peptides including peptides possess biological activities that are the same or similar to those of the wild type peptides. The term "variant" with reference to peptides encompasses all forms of peptides as defined herein.

Those of skill in the art will appreciate that the conjugates of the present invention are in certain embodiments particularly suited for stimulating T-cell responses, for example in the treatment of neoplastic diseases, including cancer. Conjugates, compositions, and vaccines of the present invention comprising one or more tumour antigens are contemplated. It will be appreciated that tumour antigens contemplated for use in the preparation of compositions, vaccines, and/or peptide conjugates of the invention will generally comprise one or more peptides. In certain embodiments of the invention, including for example pharmaceutical compositions of the invention, one or more additional tumour antigens may be present, including tumour antigens wherein the one or more tumour antigens does not comprise peptide. Tumour antigens are typically classified as either unique antigens, or shared antigens, with the latter group including differentiation antigens, cancer-specific antigens, and over-expressed antigens. Examples of each class of antigens are amenable to use in the present invention. Representative tumour antigens for use in the treatment, for example immunotherapeutic treatment, or vaccination against neoplastic diseases including cancer, are discussed below.

Compounds, vaccines and compositions comprising one or more antigens prepared using those methods of immunisation are specifically contemplated.

In certain embodiments, the tumour antigen is a peptide-containing tumour antigen, such as a polypeptide tumour antigen or glycoprotein tumour antigens. In certain embodiments, the tumour antigen is a saccharide-containing tumour antigen, such as a glycolipid tumour antigen or a ganglioside tumour antigen. In certain embodiments, the tumour antigen is a polynucleotide-containing tumour antigen that expresses a polypeptide-containing tumour antigen, for instance, an RNA vector construct or a DNA vector construct, such as plasmid DNA.

Tumour antigens appropriate for the use in the present invention encompass a wide variety of molecules, such as (a) peptide-containing tumour antigens, including peptide epitopes (which can range, for example, from 8-20 amino acids in length, although lengths outside this range are also common), lipopolypeptides and glycoproteins, (b) saccharide-containing tumour antigens, including poly-saccharides, mucins, gangliosides, glycolipids and glycoproteins, including and (c) polynucleotides that express antigenic polypeptides. Again, those skilled in the art will recognise that a tumour antigen present in a conjugate or composition of the present invention will typically comprise peptide. However, embodiments of the invention where one or more conjugates comprises a tumour antigen that does not itself comprise peptide, but for example is bound to the amino acid-comprising or peptide-containing conjugation partner, are contemplated. Similarly, compositions of the invention in which one or more tumour antigens that does not itself comprise peptide is present are contemplated.

In certain embodiments, the tumour antigens are, for example, (a) full length molecules associated with cancer cells, (b) homologues and modified forms of the same, including molecules with deleted, added and/or substituted portions, and (c) fragments of the same, provided said fragments remain antigenic or immunogenic. In certain embodiments, the tumour antigens are provided in recombinant form. In certain embodiments, the tumour antigens include, for example, class I-restricted antigens recognized by CD8+ lymphocytes or class II-restricted antigens recognized by CD4+ lymphocytes.

Shared tumour antigens are generally considered to be native, unmutated sequences that are expressed by tumours due to epigenetic changes that allow de-repression of developmentally-repressed genes. Accordingly, shared antigens are typically considered preferable to over-expressed or differentiation-associated antigens because there is no expression in normal tissues. Also, the same antigens can be targeted in a number of cancer patients. For example, the cancer-testis antigen NY-ESO-1 is present in the majority of patients with many tumours, and a sizeable minority of patients with other tumours. In another example, breast differentiation tumour antigens NYBR-1 and NYBR-1.1 are found in a proportion of breast cancer sufferers. Shared tumour antigens thus represent an attractive target for development.

The use of shared tumour antigens, such cancer-testis antigens including NY-ESO-1, CTSP-1, CTSP-2, CTSP-3, CTSP-4, SSX2, and SCP1, and breast cancer antigens NYBR-1 and NYBR-1.1, in combination with peptides or conjugates of the present invention is specifically contemplated herein.

In one exemplary embodiment, the peptide of the invention, for example, the peptide of the peptide-containing conjugation partner or of the peptide conjugate, comprises one or more epitopes derived from EBV LMP2. Representative epitopes derived from LMP2 are shown in Table 1 below.

TABLE 1

| EBV LMP2 epitopes | | | | |
|---|---|---|---|---|
| LMP2 residues | AA sequence | HLA | LMP2 Long peptide | Seq ID No. |
| 51-60 | ESNEEPPPPY | A1 | | 76 |
| 52-60 | SNEEPPPPY | A1 | 1-1 | 77 |
| 71-79 | HSDYQPLGT | A1 | S-1 | 78 |
| 76-84 | PLGTQDQSL | A2 | S-1 | 79 |
| 76-85 | PLGTQDQSLY | A1 | S-1 | 80 |
| 76-85 | PLGTQDQSLY | A3 | S-1 | 80 |
| 77-85 | LGTQDQSLY | A1 | S-1 | 81 |
| 78-86 | GTQDQSLYL | A2 | S-1 | 82 |
| 78-86 | GTQDQSLYL | A11 | S-1 | 83 |

TABLE 1-continued

EBV LMP2 epitopes

| LMP2 residues | AA sequence | HLA | LMP2 Long peptide | Seq ID No. |
|---|---|---|---|---|
| 78-87 | GTQDQSLYLG | A11 | S-1 | 84 |
| 82-90 | QSLYLGLQH | A3 | S-1 | 85 |
| 83-91 | SLYLGLQHD | A2 | S-1, S-2 | 86 |
| 83-91 | SLYLGLQHD | A3 | S-1, S-2 | 86 |
| 87-96 | GLQHDGNDGL | A2 | S-1, S-2 | 87 |
| 92-101 | GNDGLPPPPY | A1 | S-2 | 88 |
| 95-103 | GLPPPPYSP | A2 | S-2 | 89 |
| 95-104 | GLPPPPYSPR | A3 | S-2 | 90 |
| 95-104 | GLPPPPYSPR | A11 | S-2 | 90 |
| 103-111 | PRDDSSQHIY | A1 | S-2 | 91 |
| 104-112 | RDDSSQHIY | A1 | S-2 | 92 |
| 110-118 | HIYEEAGRG | A3 | 2-1 | 93 |
| 350-358 | ILLARLFLY | A3/A8/A29 | 5-1, 5-2, 5-4, 5-5 | 94 |
| 340-350 | SSCSSCPLSKI | A11 | 5-1, 5-2, 5-3, 5-4, 5-5 | 95 |
| 329-337 | LLWTLVVLL | A2 | 5-1, 5-2, 5-3, 5-5 | 96 |
| 356-364 | FLYALALLL | A2 | 5-1, 5-2, 5-4, 5-5 | 97 |
| 426-434 | CLGGLLTMV | A2 | 6-1 | 98 |
| 257-265 | LIVDAVLQL | A2 | 4-1 | 99 |
| 453-461 | LTAGFLIFL | A2 | 6-1 | 100 |
| 243-251 | TVCGGIMFL | A2 | 4-1 | 101 |

In one specifically contemplated embodiment, the peptide of the invention, for example, the isolated, purified, or recombinant peptide or the peptide of the peptide-containing conjugation partner or of the peptide conjugate, comprises, consists essentially of, or consists of an amino acid sequence selected from the group consisting of 8 or more contiguous, 10 or more contiguous, 12 or more contiguous, 15 or more contiguous, 20 or more contiguous, or 25 or more contiguous amino acids from any one of SEQ ID NOs: 1 to 101, for example, from any one of SEQ ID NOs: 1 to 93, including for example any one of SEQ ID NOs: 1 to 75.

In various embodiments, the peptide comprises more that one amino acid sequence selected from the group consisting of any one of SEQ ID NOs: 1 to 101. In one embodiment, the peptide comprises one or more amino acid sequences selected from the group consisting of SEQ ID NOs: 76-101, or from the group consisting of SEQ ID NOs: 76-93.

In one specifically contemplated embodiment, the peptide of the invention, for example, the isolated, purified, or recombinant peptide or the peptide of the peptide-containing conjugation partner or of the peptide conjugate, comprises, consists essentially of, or consists of an amino acid sequence selected from the group consisting of 8 or more contiguous, 10 or more contiguous, 12 or more contiguous, 15 or more contiguous, 20 or more contiguous, or 25 or more contiguous amino acids from any one of the sequences depicted in Table 2 below.

TABLE 2

LMP2 long peptides

| NAME | LMP2 residues | SEQUENCE | SEQ ID NO. |
|---|---|---|---|
| S-1 | 69-96 | DRHSDYQPLGTQDQSLYLGLQHDGNDGL | 5 |
| S-2 | 83-115 | SLYLGLQHDGNDGLPPPPYSPRDDSSQHIYEEA | 10 |
| S-3 | 72-96 | SDYQPLGTQDQSLYLGLQHDGNDGL | 15 |
| S-4 | 69-115 | DRHSDYQPLGTQDQSLYLGLQHDGNDGLPPPPYSPRDDSSQHIYEEA | 20 |
| 5-1 | 329-364 | LLWTLVVLLICSSCSSCPLSKILLARLFLYALALLL | 25 |
| 5-2 | 327-366 | LMLLWTLVVLLICSSCSSCPLSKILLARLFLYALALLLLA | 30 |
| 5-3 | 327-352 | LMLLWTLVVLLICSSCSSCPLSKILL | 35 |
| 5-4 | 336-366 | LLICSSCSSCPLSKILLARLFLYALALLLLA | 40 |
| 5-5 | 319-375 | LNLTTMFLLMLLWTLVVLLICSSCSSCPLSKILLARLFLYALALLLLASALIAGGSI | 45 |
| 5-6 | 325-368 | FLLMLLWTLVVLLICSSCSSCPLSKILLARLFLYALALLLLASA | 50 |

TABLE 2-continued

LMP2 long peptides

| NAME | LMP2 residues | SEQUENCE | SEQ ID NO. |
|---|---|---|---|
| 4-1 | 219-269 | LQGIYVLVMLVLLILAYRRRWRRLTVCGGIM FLACVLVLIVDAVLQLSPLL | 55 |
| 6-1 | 415-465 | SGNRTYGPVFM(C)(S)LGGLLTMVAGAVWL TVMSNTLLSAWILTAGFLIFLIGFA | 60 |
| 1-1 | 52-98 | SNEEPPPPYEDPYWGNGDRHSDYQPLGTQDQSL YLGLQHDGNDGLPP | 65 |
| 2-1 | 92-142 | GNDGLPPPPYSPRDDSSQHIYEEAGRGSMNP VCLPVIVAPYLFWLAAIAAS | 70 |
| 3-1 | 137-186 | AAIAASCFTASVSTVVTATGLALSLLLLAAV ASSYAAAQRKLLTPVTVLT | 75 |

Similarly, the prostate vaccine Sipuleucel-T (APC8015, Provenge™), which comprises the antigen prostatic acid phosphatase (PAP), is present in 95% of prostate cancer cells. At least in part due to this potential for efficacy in a significant proportion of prostate cancer sufferers, Sipuleucel-T was approved by the FDA in 2010 for use in the treatment of asymptomatic, hormone-refractory prostate cancer. The use of PAP antigen in conjugates of the present invention is specifically contemplated in the present invention.

Unique antigens are considered to be those antigens that are unique to an individual or are shared by a small proportion of cancer patients, and typically result from mutations leading to unique protein sequences. Representative examples of unique tumour antigens include mutated Ras antigens, and mutated p53 antigens. As will be appreciated by those skilled in the art having read this specification, the methods of the present invention enable the ready preparation of conjugates comprising one or more unique tumour antigens, for example to elicit specific T-cell responses to one or more unique tumour antigens, for example in the preparation of patient-specific therapies.

Accordingly, representative tumour antigens include, but are not limited to, (a) antigens such as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumours), (b) mutated antigens, for example, p53 (associated with various solid tumours, for example, colorectal, lung, head and neck cancer), p21/Ras (associated with, for example, melanoma, pancreatic cancer and colorectal cancer), CDK4 (associated with, for example, melanoma), MUM1 (associated with, for example, melanoma), caspase-8 (associated with, for example, head and neck cancer), CIA 0205 (associated with, for example, bladder cancer), HLA-A2-R1701, beta catenin (associated with, for example, melanoma), TCR (associated with, for example, T-cell non-Hodgkins lymphoma), BCR-abl (associated with, for example, chronic myelogenous leukemia), triosephosphate isomerase, MA 0205, CDC-27, and LDLR-FUT, (c) over-expressed antigens, for example, Galectin 4 (associated with, for example, colorectal cancer), Galectin 9 (associated with, for example, Hodgkin's disease), proteinase 3 (associated with, for example, chronic myelogenous leukemia), Wilm's tumour antigen-1 (WT 1, associated with, for example, various leukemias), carbonic anhydrase (associated with, for example, renal cancer), aldolase A (associated with, for example, lung cancer), PRAME (associated with, for example, melanoma), HER-2/neu (associated with, for example, breast, colon, lung and ovarian cancer), alpha-fetoprotein (associated with, for example, hepatoma), KSA (associated with, for example, colorectal cancer), gastrin (associated with, for example, pancreatic and gastric cancer), telomerase catalytic protein, MUC-1 (associated with, for example, breast and ovarian cancer), G-250 (associated with, for example, renal cell carcinoma), p53 (associated with, for example, breast, colon cancer), and carcinoembryonic antigen (associated with, for example, breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, for example, melanoma), (e) prostate associated antigens such as PAP, prostatic serum antigen (PSA), PSMA, PSH-P1, PSM-P1, PSM-P2, associated with for example, prostate cancer, (f) immunoglobulin idiotypes (associated with myeloma and B cell lymphomas, for example), and (g) other tumour antigens, such as polypeptide- and saccharide-containing antigens including (i) glycoproteins such as sialyl Tn and sialyl Le.sup.x (associated with, for example, breast and colorectal cancer) as well as various mucins; glycoproteins are coupled to a carrier protein (for example, MUC-1 are coupled to KLH); (ii) lipopolypeptides (for example, MUC-1 linked to a lipid moiety); (iii) polysaccharides (for example, Globo H synthetic hexasaccharide), which are coupled to a carrier proteins (for example, to KLH), (iv) gangliosides such as GM2, GM12, GD2, GD3 (associated with, for example, brain, lung cancer, melanoma), which also are coupled to carrier proteins (for example, KLH).

Other representative tumour antigens amenable to use in the present invention include TAG-72, (See, e.g., U.S. Pat. No. 5,892,020; human carcinoma antigen (See, e.g., U.S. Pat. No. 5,808,005); TP1 and TP3 antigens from osteocarcinoma cells (See, e.g., U.S. Pat. No. 5,855,866); Thomsen-Friedenreich (TF) antigen from adenocarcinoma cells (See, e.g., U.S. Pat. No. 5,110,911); KC-4 antigen from human prostrate adenocarcinoma (See, e.g., U.S. Pat. No. 4,743, 543); a human colorectal cancer antigen (See, e.g., U.S. Pat. No. 4,921,789); CA125 antigen from cystadenocarcinoma (See, e.g., U.S. Pat. No. 4,921,790); DF3 antigen from human breast carcinoma (See, e.g., U.S. Pat. Nos. 4,963,484 and 5,053,489); a human breast tumour antigen (See, e.g., U.S. Pat. No. 4,939,240); p97 antigen of human melanoma (See, e.g., U.S. Pat. No. 4,918,164); carcinoma or orosomucoid-related antigen (CORA) (See, e.g., U.S. Pat. No. 4,914, 021); T and Tn haptens in glycoproteins of human breast carcinoma, MSA breast carcinoma glycoprotein; MFGM breast carcinoma antigen; DU-PAN-2 pancreatic carcinoma antigen; CA125 ovarian carcinoma antigen; YH206 lung carcinoma antigen, Alphafetoprotein (AFP), hepatocellular carcinoma antigen; Carcinoembryonic antigen (CEA); bowel cancer antigen; Epithelial tumour antigen (ETA); breast cancer antigen; Tyrosinase; the raf oncogene product; gp75; gp100; EBV-LMP 1 & 2; EBV-EBNA 1, 2 & 3C; HPV-E4, 6, 7; C017-1A; GA733; gp72; p53; proteinase 3; telomerase; and melanoma gangliosides. These and other tumour antigens, whether or not presently characterized, are contemplated for use in the present invention.

In certain embodiments, the tumour antigens are derived from mutated or altered cellular components. Representative examples of altered cellular components include, but are not limited to ras, p53, Rb, altered protein encoded by the Wilms' tumour gene, ubiquitin, mucin, protein encoded by the DCC, APC, and MCC genes, as well as receptors or receptor-like structures such as neu, thyroid hormone receptor, platelet derived growth factor (PDGF) receptor, insulin receptor, epidermal growth factor (EGF) receptor, and the colony stimulating factor (CSF) receptor.

Polynucleotide-containing antigens used in the present invention include polynucleotides that encode polypeptide tumour antigens such as those listed above. In certain embodiments, the polynucleotide-containing antigens include, but are not limited to, DNA or RNA vector constructs, such as plasmid vectors (e.g., pCMV), which are capable of expressing polypeptide tumour antigens in vivo.

The present invention also contemplates the preparation of conjugates comprising viral antigens that are capable of stimulating T-cell to elicit effective anti-viral immunity in patients who are or have been immunosuppressed, for example patients who have had bone marrow transplants, haematopoietic stem cell transplants, or are otherwise undergoing immunosuppression.

Similarly, antigens derived from viruses associated with increased incidence of cancer, or that are reported to be cancer-causing, such as human papillomavirus, hepatitis A virus, and hepatitis B virus, are contemplated for use in the present invention.

For example, in certain embodiments, the tumour antigens include, but are not limited to, p15, Hom/Mel-40, H-Ras, E2A-PRL, H4-RET, IGH-IGK, MYL-RAR, Epstein Barr virus antigens, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like.

The above-listed or referenced antigens are exemplary, not limiting, of the present invention.

The present invention also relates to pharmaceutical composition comprising an effective amount of a peptide conjugate of the present invention or a pharmaceutically acceptable salt or solvent thereof, and a pharmaceutically acceptable carrier.

The present invention relates to a pharmaceutical composition comprising an effective amount of a peptide of the present invention or a pharmaceutically acceptable salt or solvate thereof, and a pharmaceutically acceptable carrier.

The pharmaceutical compositions may comprise an effective amount of two or more peptides of the invention, two or more peptide conjugates of the invention, or one more peptides of the invention and one or more peptide conjugates of the invention in combination.

The term "pharmaceutically acceptable carrier" refers to a carrier (adjuvant or vehicle) that may be administered to a subject together with the peptide or peptide conjugate of the present invention, or a pharmaceutically acceptable salt or solvent thereof, and a pharmaceutically acceptable carrier.

Pharmaceutically acceptable carriers that may be used in the compositions include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α—, β—, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery. Oil solutions or suspensions may also contain a long-chain alcohol diluent or dispersant, or carboxymethyl cellulose or similar dispersing agents, which are commonly used in the formulation of pharmaceutically acceptable dosage forms such as emulsions and or suspensions.

The compositions are formulated to allow for administration to a subject by any chosen route, including but not limited to oral or parenteral (including topical, subcutaneous, intramuscular and intravenous) administration.

For example, the compositions may be formulated with an appropriate pharmaceutically acceptable carrier (including excipients, diluents, auxiliaries, and combinations thereof) selected with regard to the intended route of administration and standard pharmaceutical practice. For example, the compositions may be administered orally as a powder, liquid, tablet or capsule, or topically as an ointment, cream or lotion. Suitable formulations may contain additional agents as required, including emulsifying, antioxidant, flavouring or colouring agents, and may be adapted for immediate-, delayed-, modified-, sustained-, pulsed- or controlled-release.

The compositions may be formulated to optimize bioavailability, immunogenicity, or to maintain plasma, blood, or tissue concentrations within the immunogenic or therapeutic range, including for extended periods. Controlled delivery preparations may also be used to optimize the antigen concentration at the site of action, for example.

The compositions may be formulated for periodic administration, for example to provide continued exposure. Strategies to elicit a beneficial immunological response, for example those that employ one or more "booster" vaccinations, are well known in the art, and such strategies may be adopted.

The compositions may be administered via the parenteral route. Examples of parenteral dosage forms include aqueous solutions, isotonic saline or 5% glucose of the active agent, or other well-known pharmaceutically acceptable excipients. Cyclodextrins, for example, or other solubilising agents well-known to those familiar with the art, can be utilized as pharmaceutical excipients for delivery of the therapeutic agent.

Examples of dosage forms suitable for oral administration include, but are not limited to tablets, capsules, lozenges, or like forms, or any liquid forms such as syrups, aqueous solutions, emulsions and the like, capable of providing a therapeutically effective amount of the composition. Capsules can contain any standard pharmaceutically acceptable materials such as gelatin or cellulose. Tablets can be formulated in accordance with conventional procedures by compressing mixtures of the active ingredients with a solid carrier and a lubricant. Examples of solid carriers include starch and sugar bentonite. Active ingredients can also be administered in a form of a hard shell tablet or a capsule containing a binder, e.g., lactose or mannitol, a conventional filler, and a tabletting agent.

Examples of dosage forms suitable for transdermal administration include, but are not limited, to transdermal patches, transdermal bandages, and the like.

Examples of dosage forms suitable for topical administration of the compositions include any lotion, stick, spray, ointment, paste, cream, gel, etc., whether applied directly to the skin or via an intermediary such as a pad, patch or the like.

Examples of dosage forms suitable for suppository administration of the compositions include any solid dosage form inserted into a bodily orifice particularly those inserted rectally, vaginally and urethrally.

Examples of dosage of forms suitable for injection of the compositions include delivery via bolus such as single or multiple administrations by intravenous injection, subcutaneous, subdermal, and intramuscular administration or oral administration.

Examples of dosage forms suitable for depot administration of the compositions and include pellets of the peptides or peptide conjugates or solid forms wherein the peptides or peptide conjugates are entrapped in a matrix of biodegradable polymers, microemulsions, liposomes or are microencapsulated.

Examples of infusion devices for the compositions include infusion pumps for providing a desired number of doses or steady state administration, and include implantable drug pumps.

Examples of implantable infusion devices for compositions include any solid form in which the peptides or peptide conjugates are encapsulated within or dispersed throughout a biodegradable polymer or synthetic, polymer such as silicone, silicone rubber, silastic or similar polymer.

Examples of dosage forms suitable for transmucosal delivery of the compositions include depositories solutions for enemas, pessaries, tampons, creams, gels, pastes, foams, nebulised solutions, powders and similar formulations containing in addition to the active ingredients such carriers as are known in the art to be appropriate. Such dosage forms include forms suitable for inhalation or insufflation of the compositions, including compositions comprising solutions and/or suspensions in pharmaceutically acceptable, aqueous, or organic solvents, or mixture thereof and/or powders. Transmucosal administration of the compositions may utilize any mucosal membrane but commonly utilizes the nasal, buccal, vaginal and rectal tissues. Formulations suitable for nasal administration of the compositions may be administered in a liquid form, for example, nasal spray, nasal drops, or by aerosol administration by nebulizer, including aqueous or oily solutions of the polymer particles. Formulations may be prepared as aqueous solutions for example in saline, solutions employing benzyl alcohol or other suitable preservatives, absorption promoters to enhance bio-availability, fluorocarbons, and/or other solubilising or dispersing agents known in the art.

Examples of dosage forms suitable for buccal or sublingual administration of the compositions include lozenges, tablets and the like. Examples of dosage forms suitable for opthalmic administration of the compositions include inserts and/or compositions comprising solutions and/or suspensions in pharmaceutically acceptable, aqueous, or organic solvents.

Examples of formulations of compositions, including vaccines, may be found in, for example, Sweetman, S. C. (Ed.). Martindale. The Complete Drug Reference, 33rd Edition, Pharmaceutical Press, Chicago, 2002, 2483 pp.; Aulton, M. E. (Ed.) Pharmaceutics. The Science of Dosage Form Design. Churchill Livingstone, Edinburgh, 2000, 734 pp.; and, Ansel, H. C., Allen, L. V. and Popovich, N. G. Pharmaceutical Dosage Forms and Drug Delivery Systems, 7th Ed., Lippincott 1999, 676 pp. Excipients employed in the manufacture of drug delivery systems are described in various publications known to those skilled in the art including, for example, Kibbe, E. H. Handbook of Pharmaceutical Excipients, 3rd Ed., American Pharmaceutical Association, Washington, 2000, 665 pp. The United States Pharmacopeia also provides examples of modified-release oral dosage forms, including those formulated as tablets or capsules. See, for example, The United States Pharmacopeia 23/National Formulary 18, The United States Pharmacopeial Convention, Inc., Rockville Md., 1995 (hereinafter "the USP"), which also describes specific tests to determine the drug release capabilities of extended-release and delayed-release tablets and capsules. The USP test for drug release for extended-release and delayed-release articles is based on drug dissolution from the dosage unit against elapsed test time. Descriptions of various test apparatus and procedures may be found in the USP. Further guidance concerning the analysis of extended release dosage forms has been provided by the F.D.A. (See Guidance for Industry. Extended release oral dosage forms: development, evaluation, and application of in vitro/in vivo correlations. Rockville, Md.: Center for Drug Evaluation and Research, Food and Drug Administration, 1997).

While the composition may comprise one or more extrinsic adjuvants, advantageously in some embodiments this is not necessary. In some embodiments, the peptide conjugate comprises an epitope and is self adjuvanting.

The present invention provides a method of vaccinating or eliciting an immune response in a subject comprising administering to the subject an effective amount of a peptide conjugate or peptide of the present invention. The present invention also relates to use of a peptide conjugate or peptide of the invention for vaccinating or eliciting an immune response in a subject, and to use of a peptide conjugate or a peptide of the invention in the manufacture of a medicament for vaccinating or eliciting an immune response in a subject.

The present invention also provides a method of vaccinating or eliciting an immune response in a subject comprising administering to the subject an effective amount of the pharmaceutical composition of the present invention. The present invention also relates to use of a pharmaceutical composition of the invention for vaccinating or eliciting an immune response in a subject, and to the use of one or more peptides of the present invention or one or more peptide conjugates of the present invention in the manufacture of a medicament for vaccinating or eliciting an immune response in a subject.

The present invention provides a method of eliciting an immune response in a subject comprising administering to the subject an effective amount of a peptide of the present invention. The present invention also relates to use of a conjugate of the invention for eliciting an immune response, and to use of a peptide conjugate of the invention in the manufacture of a medicament for eliciting an immune response in a subject.

The present invention provides a method of vaccinating a subject comprising administering to the subject an effective amount of a peptide of the present invention. The present invention also relates to use of a conjugate of the invention for eliciting an immune response, and to use of a peptide conjugate of the invention in the manufacture of a medicament for eliciting an immune response in a subject.

The administration or use of one or more peptides of the present invention and/or one or more peptide conjugates of the present invention, for example one or more peptide in together with one or more peptide conjugates, for vaccinating or eliciting an immune response in the subject is contemplated herein.

Where two or more peptides, two or more peptide conjugates, or one or more peptides and one or more peptide conjugates are administered or used, the two or more peptides, two or more peptide conjugates, or one or more peptides and one or more peptide conjugates may be administered or used simultaneously, sequentially, or separately.

A "subject" refers to a vertebrate that is a mammal, for example, a human. Mammals include, but are not limited to, humans, farm animals, sport animals, pets, primates, mice and rats.

An "effective amount" is an amount sufficient to effect beneficial or desired results including clinical results. An effective amount can be administered in one or more administrations by various routes of administration.

The effective amount will vary depending on, among other factors, the disease indicated, the severity of the disease, the age and relative health of the subject, the potency of the compound administered, the mode of administration and the treatment desired. A person skilled in the art will be able to determine appropriate dosages having regard to these any other relevant factors.

The efficacy of a composition can be evaluated both in vitro and in vivo. For example, the composition can be tested in vitro or in vivo for its ability to induce a cell-mediated immune response. For in vivo studies, the composition can be fed to or injected into an animal (e.g., a mouse) and its effects on eliciting an immune response are then assessed. Based on the results, an appropriate dosage range and administration route can be determined.

The composition may be administered as a single dose or a multiple dose schedule. Multiple doses may be used in a primary immunisation schedule and/or in a booster immunisation schedule.

In certain embodiments, eliciting an immune response comprises raising or enhancing an immune response. In exemplary embodiments, eliciting an immune response comprises eliciting a humoral and a cell mediated response.

In certain embodiments, eliciting an immune response provides immunity.

The immune response is elicited for treating a disease or condition. A person skilled in the art will appreciate that the peptides and peptide conjugates described herein are useful for treating a variety of diseases and conditions associated with EBV, including one or more diseases or conditions selected from EBV-associated neoplastic conditions, including B and T cell non-Hodgkin's lymphomas, Hodgkin's disease, and lymphoepithelioma-like carcinomas, including but not limited to nasopharyngeal carcinoma (NPC).

In some embodiments, the disease or condition is an infectious disease, cancer, or viral re-activation post-bone marrow transplant or following induction of profound immunosuppression for any other reason.

The term "treatment", and related terms such as "treating" and "treat", as used herein relates generally to treatment of a human or a non-human subject, in which some desired therapeutic effect is achieved. The therapeutic effect may, for example, be inhibition, reduction, amelioration, halt, or prevention of a disease or condition.

The compositions may be used to elicit systemic and/or mucosal immunity. Enhanced systemic and/or mucosal immunity may be reflected in an enhanced TH1 and/or TH2 immune response. The enhanced immune response may include an increase in the production of IgG1 and/or IgG2a and/or IgA.

The invention consists in the foregoing and also envisages constructions of which the following gives examples only and in no way limit the scope thereof.

EXAMPLES

Example 1. Preparation of Conjugates 200, 20, 22, and 26

1.1 General Details

Commercially available starting materials are purchased from Acros Organics, Ajax Finechem, Alfa Aesar, CEM, GL-Biochem, Merck, NOVA Biochem, Sigma Aldrich and TCI and are used as supplied. Dried solvents are prepared through distillation under $N_2$ or argon atmosphere. Tetrahydrofuran (THF) is freshly distilled over sodium/benzophenone ketyl. Methanol (MeOH) and toluene are freshly distilled over calcium hydride. Yields refer to chromatographically and spectroscopically ($^1$H NMR) homogenous materials unless otherwise stated.

Thin layer chromatography (TLC) is performed on Merck Kieselgel $F_{254}$ 200 μm silica plates. Ultraviolet light is used as a visualising agent and the general developing agents of potassium permanganate in an aqueous basic solution and vanillin in an ethanolic solution. Specific developing agents used are ethanolic solutions of ninhydrin with acid for the identification of primary amines. Heating is applied when using any developing agent. Silica gel (0.063-0.100 mm) is used for flash column chromatography.

Nuclear magnetic resonance (NMR) spectra are acquired at room temperature in $CDCl_3$ or $D_2O$ on a Bruker DRX400 spectrometer operating at 400 MHz for $^1$H nuclei and 100 MHz for $^{13}$C nuclei. Reference peaks for $^1$H and $^{13}$C spectra are respectively set to 60.00 and δ 77.0 for $CDCl_3$ and δ4.79 for $^1$H spectra in $D_2O$. NMR data are reported in values of chemical shift as parts per million (ppm) on the δ scale, and coupling constants in hertz (Hz). Multiplicities are reported as s=singlet, d=doublet, t=triplet, q=quartet, dd=doublet of doublets, dt=doublet of triplets, tt=triplet of triplets, dq=doublet of quartets, dqn=doublet of quintets, sx=sextet, br s=broad singlet, and m=multiplet. The assignment of $C_q$ is used to denote a quaternary carbon.

High resolution mass spectra are obtained on a Bruker microOTOF-Q II mass spectrometer at a nominal resolution of 5000. Analytical high-performance liquid chromatography (HPLC) and liquid chromatography-mass spectrometry (LC-MS) chromatograms are acquired on either a Dionex UltiMate 3000 HPLC system with a Finnigan Surveyor MSQ Plus mass spectrometer or an Agilent 1120 Compact LC system with a Hewlett Packard Series 1100 MSD mass spectrometer. Analytical reverse phase (RP) HPLC is performed using the $MeCN/H_2O$+0.1% TFA solvent system.

Semipreparative RP HPLC is performed on a Dionex UltiMate 3000 HPLC system using the $MeCN/H_2O$+0.1% TFA solvent system. Microwave reactions are performed using a CEM Liberty Automated Microwave system.

1.2 General Method for Peptide Chain Elongation
Manual Synthesis Method

Swelled peptide-resin is treated with 20% v/v piperidine in DMF (5.0 mL) and shaken for 20 min at r.t. The solution is drained and the resin washed with DMF (×2) and DCM (×2). A coupling mixture of Fmoc-AA-OH (2.0 eq.), HBTU (2.0 eq) and iPr$_2$NEt (4.0 eq.) in DMF (1 mL) is added and the resin shaken for 1 hr. Resin is drained and washed again. The procedure is repeated for the remaining residues in the sequence.

Automated Synthesis Method (Standard, 0.2 Mmol Scale)

Peptide-resin is transferred to the reaction vessel of a Tribute automated peptide synthesiser. Automated synthesis is undertaken with cycles of Fmoc deprotection and Fmoc-AA-OH coupling steps. Deprotection is undertaken by addition of 20% v/v piperidine in DMF (6.0 mL) and agitation (2×7 min). Following resin drainage and DMF washing (4 mL×3), a coupling step is performed with 5 eq. Fmoc-AA-OH dissolved in HBTU (0.24 mM, in DMF, 4 mL). 2 M N-methylmorpholine (NMM) in DMF (4 mL) is utilised in the base-addition step. Coupling proceeded for 1 hr. After DMF washing steps, the next cycle of deprotection and coupling commenced, repeating until all amino acids are coupled.

Procedure for Coupling of Cysteine Derivatives (0.1 Mmol Scale)

Peptide-resin is swelled in 1:1 CH$_2$Cl$_2$:DMF for 30 min, then drained. A coupling mixture of a Cys amino acid (0.2 mmol, 2 eq.), BOP (0.4 mmol, 4 eq.) and HOBt.H$_2$O (0.4 mmol, 4 eq.) is dissolved in 1:1 CH$_2$Cl$_2$:DMF (2 mL). 2,4,6-collidine (0.4 mmol, 4 eq.) is then added and the resultant solution added to the peptide-resin. The resin is agitated for 1 hr, or until ninhydrin test indicated no free amines. The resin is then drained, washed with DMF (2×) and CH$_2$Cl$_2$ (2×), and dried.

Ninhydrin Test Procedure

A small portion of resin is taken, washed with CH$_2$Cl$_2$ and allowed to dry. 1 drop each of solutions of 5% v/v ninhydrin in EtOH, 80% w/v phenol in EtOH and 2% v/v KCN in pyridine are added to the resin and the mixture heated at 90° C. for 2 minutes. Blue-coloured beads and solution indicated the presence of free primary amines, while a yellow colour indicated no free amino groups present.

1.3 Preparation of Amino Add Conjugate 200

N-Fluorenylmethoxycarbonyl-[R]-cysteine

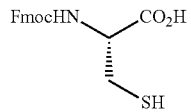

Fmoc-Cys(Trt)-OH (1.0 g, 1.7 mmol) is dissolved in CH$_2$Cl$_2$ (50 mL). TFA (1.5 mL, 19.6 mmol) and iPr$_3$SiH (0.75 mL) are added, causing the solution to turn yellow. The solution is agitated for 2 hrs at room temperature, at which point the solution turns colourless. The mixture is basified to pH 9 by addition of Na$_2$CO$_3$.H$_2$O and washed with EtOAc. The solution is acidified with 10M HCl, extracted with EtOAc and concentrated in vacuo to give a white powder and a pink residue. The powder and residue are dissolved in 4:1 MeCN:H$_2$O and lyophilised, giving a crude pink-white powder (424 mg, crude yield 73.1%). This crude product is carried through to the thiol-ene reactions described below.

(R)-2-((((9H-fluoren-9-yl)methoxy)carbonyl)
amino)-3-((2-(palmitoyloxy)ethyl)thio)propanoic
add (200)

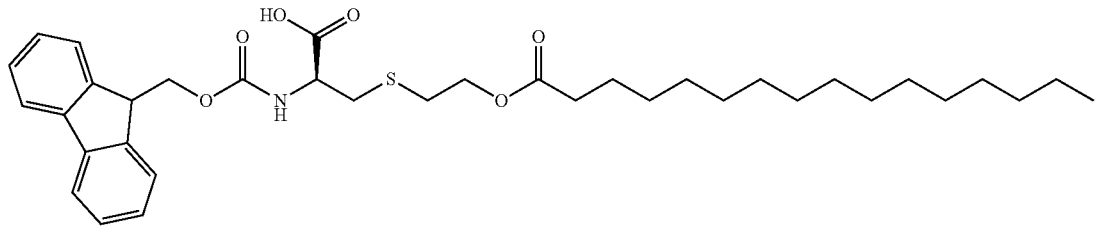 [SMILES: CCCCCCCCCCCCCCCC(=O)OCCSC[C@@H](NC(=O)OCC1c2ccccc2-c2ccccc21)C(=O)O]

*Thermal Initiation* (Li, J. Dong, S. et al. Chemistry as an Expanding Resource in Protein Science: Fully Synthetic and Fully Active Human Parathyroid Hormone-Related Protein (1-141). *Angewandte Chemie International Edition* 2012, 51 (49), 12263-12267).

Fmoc-Cys-OH (100 mg, 0.29 mmol), vinyl palmitate (476 µL, 1.5 mmol) and AIBN (9.6 mg, 59 µmol) are dissolved in degassed 1,2-dichloroethane (3 mL). The reaction mixture is then heated under reflux (90° C.) for 24 hr, after which TLC indicated complete consumption of Fmoc-Cys-OH. The solution is then allowed to cool to r.t. The solvent is removed under reduced pressure. Presence of the desired product 200 in the crude reaction mixture is confirmed by mass spectrometry.

Photo-Initiation

Fmoc-Cys-OH (100 mg, 0.29 mmol) is dissolved in degassed, anhydrous DMF (500 µL). Vinyl palmitate (90 µL, 0.3 mmol) and DMPA (5.0 mg, 20 µmol) are dissolved in degassed CH$_2$Cl$_2$ (200 µL). The two solutions are combined and the resultant mixture irradiated for 6 hr (365 nm UV) in a standard photochemical apparatus. When no further change in the reaction mixture can be observed by TLC, solvent is removed under reduced pressure. The crude product is purified by silica gel flash chromatography (3:1 EtOAc:n-hexanes+2% AcOH), followed by lyophilization from 1:1 H2O:MeCN+0.1% TFA to afford the title compound as a powdery white solid (24 mg, 13%). Structure of the desired product 200 is confirmed by mass spectrometry.

1.4 Preparation of Peptide Conjugates 20, 22, and 26 Peptides

[SEQ ID NO: 102]
AcN-Cys-Ser-Lys-Lys-Lys-Lys-Asp-Arg-His-Ser-Asp-
Tyr-Gln-Pro-Leu-Gly-Thr-Gln-Asp-Gln-Ser-Leu-Tyr-
Leu-Gly-Leu-Gln-His-Asp-Gly-Asn-Asp-Gly-Leu-OH 25

To aminomethyl polystyrene (PS) resin (0.20 g, 1.0 mmol/g loading, 0.2 mmol scale) pre-swelled in 1:1 CH$_2$Cl$_2$:DMF is added a coupling mixture of Fmoc-L-Val-O—CH$_2$-phi-OCH$_2$—CH$_2$—COOH (155.2 mg, 0.3 mmol), HBTU (113.8 mg, 0.3 mmol) and iPr$_2$NEt (104 µL, 0.6 mmol) in DMF (3 mL). The resin is shaken for 2 hrs at r.t., after which a ninhydrin test is performed to monitor complete coupling. The Fmoc-Val amino group is then deprotected by treatment of the resin with 20% v/v piperidine in DMF (5 mL) for 20 mins at r.t. The resin is transferred to a Tribute automated peptide synthesiser. Chain elongation up to and including the Ser residue is performed using the general automated coupling method. Coupling of the Fmoc-Cys(Trt)-OH residue is performed manually with addition of a mixture of Fmoc-Cys(Trt)-OH (235 mg, 0.4 mmol), BOP (360 mg, 0.8 mmol), HOBt.H$_2$O (120 mg, 0.8 mmol) and 2,4,6-collidine (120 µL, 0.8 mmol) in 1:1 CH$_2$Cl$_2$:DMF (2 mL). The resin is shaken for 1 hr at r.t., after which a ninhydrin test is performed to monitor complete coupling. Final Fmoc deprotection is accomplished by treatment of the resin with 20% v/v piperidine in DMF (5 mL) for 20 mins at r.t.

After Fmoc deprotection, N-acetylation is performed by adding acetic anhydride (50 µL) and iPr$_2$NEt (50 µL) in DMF (3 mL) to the resin. The resin is then shaken for 30 min at r.t., after which a ninhydrin test is performed to ensure no remaining free amines. The resin is drained, washed with DMF and CH$_2$Cl$_2$ and air dried. A cleavage cocktail of TFA:H2O:DODT:iPr$_3$SiH (94:2.5:2.5:1% v/v, 10.0 mL) is added to the dry resin and the mixture shaken for 4 hr at r.t. The cleavage cocktail is then treated with cold diethyl ether to precipitate the crude peptide, which is centrifuged at 4000 rpm for 5 minutes. The supernatant is discarded and the pellet washed with diethyl ether, before repeating the spinning step. The ether phase is then discarded and the peptide dried with N$_2$ flow. The crude peptide is then lyophilised from H$_2$O+0.1% TFA. The crude product is carried through to the thiol-ene reaction step outlined below.

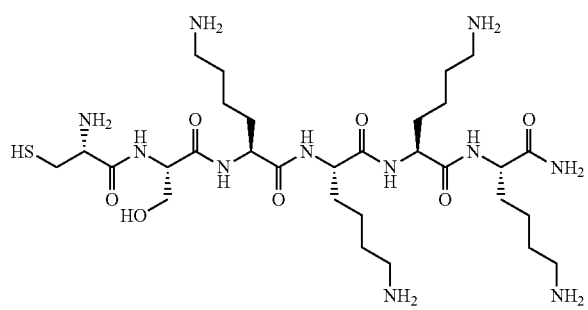

Cys-Ser-Lys-Lys-Lys-Lys-NH$_2$ [SEQ ID NO: 103]

To aminomethyl polystyrene (PS) resin (0.20 g, 1.0 mmol/g loading, 0.2 mmol scale) pre-swelled in 1:1 CH$_2$Cl$_2$:DMF is added a coupling mixture of Fmoc-Rink-Amide-OH (216 mg, 0.4 mmol), HBTU (151.8 mg, 0.4 mmol) and iPr$_2$NEt (140 µL, 0.8 mmol) in DMF (2 mL). The resin is shaken for 1 hr at r.t., after which a ninhydrin test is performed to establish complete coupling. The linker amino group is then deprotected by treatment of the resin with 20% v/v piperidine in DMF (5 mL) for 20 mins at r.t. The resin is transferred to a Tribute automated peptide synthesiser. Chain elongation up to and including the Ser residue is performed using the general automated coupling method. Coupling of the Cys residue is performed manually with addition of a mixture of Fmoc-Cys(Trt)-OH (235 mg, 0.4 mmol), BOP (360 mg, 0.8 mmol), HOBt.H$_2$O (120 mg, 0.8 mmol) and 2,4,6-collidine (120 µL, 0.8 mmol) in 1:1 CH$_2$Cl$_2$:DMF (2 mL). The resin is shaken for 1 hr at r.t., after which a ninhydrin test is performed to establish complete coupling. Final Fmoc deprotection is accomplished by treatment of the resin with 20% v/v piperidine in DMF (5 mL) for 20 mins at r.t. The resin is drained, washed with DMF and CH$_2$Cl$_2$ and air dried. A cleavage cocktail of TFA:H$_2$O:DODT:iPr$_3$SiH (94:2.5:2.5:1% v/v, 10.0 mL) is added to the dry resin and the mixture shaken for 2 hr at r.t. The cleavage cocktail is then treated with cold diethyl ether to precipitate the crude peptide, which is centrifuged at 4000 rpm for 5 minutes. The supernatant is discarded and the pellet washed with diethyl ether, before repeating the spinning step. The ether phase is then discarded and the peptide dried with N$_2$ flow. The crude peptide is then lyophilised from H$_2$O+0.1% TFA. The crude product is carried through to the thiol-ene reaction step outlined below.

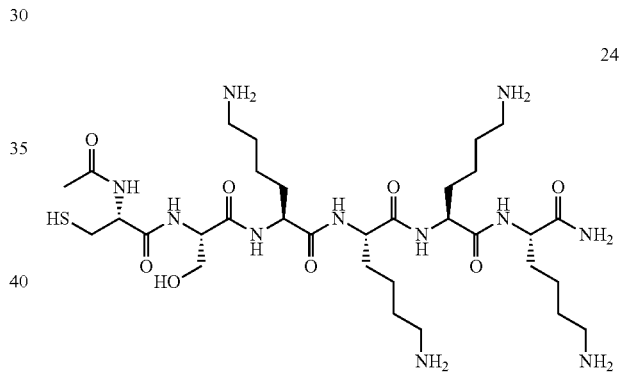

Ac-Cys-Ser-Lys-Lys-Lys-Lys-NH$_2$ 24 [SEQ ID NO: 103]

To aminomethyl polystyrene (PS) resin (0.20 g, 1.0 mmol/g loading, 0.2 mmol scale) pre-swelled in 1:1 CH$_2$Cl$_2$:DMF is added a coupling mixture of Fmoc-Rink-Amide-OH (216 mg, 0.4 mmol), HBTU (151.8 mg, 0.4 mmol) and iPr$_2$NEt (140 µL, 0.8 mmol) in DMF (2 mL). The resin is shaken for 1 hr at r.t., after which a ninhydrin test indicated complete coupling. The linker amino group is then deprotected by treatment of the resin with 20% v/v piperidine in DMF (5 mL) for 20 mins at r.t. The resin is transferred to a Tribute automated peptide synthesiser. Chain elongation up to and including the Ser(Trt) residue is performed using the general automated coupling method. Coupling of the Cys residue is performed manually with addition of a mixture of Fmoc-Cys(Trt)-OH (235 mg, 0.4 mmol), BOP (360 mg, 0.8 mmol), HOBt.H$_2$O (120 mg, 0.8 mmol) and 2,4,6-collidine (120 µL, 0.8 mmol) in 1:1 CH$_2$Cl$_2$:DMF (2 mL). The resin is shaken for 1 hr at r.t., after which a ninhydrin test is performed to establish complete coupling. After Fmoc deprotection, N-acetylation is performed by adding acetic anhydride (50 µL) and iPr$_2$NEt (50 µL) in DMF (3 mL) to the resin. The resin is then shaken for 30 min at r.t., after which a ninhydrin test is performed to establish no remaining free amines. The resin is drained, washed with DMF and $CH_2Cl_2$ and air dried. A cleavage cocktail of $TFA:H_2O:DODT:iPr_3SiH$ (94:2.5:2.5:1% v/v, 10.0 mL) is added to the dry resin and the mixture shaken for 2 hr at r.t. The cleavage cocktail is then treated with cold diethyl ether to precipitate the crude peptide, which is centrifuged at 4000 rpm for 5 minutes. The supernatant is discarded and the pellet washed with diethyl ether, before repeating the spinning step. The ether phase is then discarded and the peptide dried with $N_2$ flow. The crude peptide is then lyophilised from $H_2O+0.1\%$ TFA. The crude product is carried through to the thiol-ene reaction step outlined below.

Peptide Conjugates

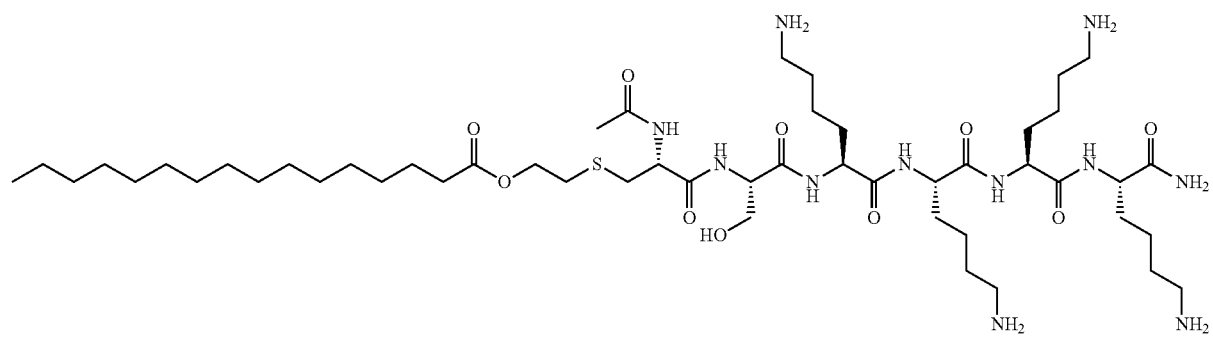

22

Thiol-ene reaction product of Ac-Cys-Ser-Lys-Lys-Lys-Lys-$NH_2$ 24 [SEQ ID NO: 103] and vinyl palmitate 22

To crude peptide 24 (25 mg, 32.6 μmol) and DMPA (3.3 mg, 13.1 μmol) in a solution of NMP (4 mL) is added vinyl palmitate (52.9 μL, 0.16 mmol). The resultant mixture is irradiated, with agitation, at 365 nm for 1 hr in a standard UV photochemical apparatus. The desired product 22 is detected by mass analysis. The crude product 22 is purified via semi-preparative RP HPLC on a Phenomenex Gemini C18 column running a gradient of 5-65% $MeCN:H_2O+0.1\%$ TFA (3% MeCN per min, 50° C.). Mass spectrometry is used to confirm the structure of the desired product 22.

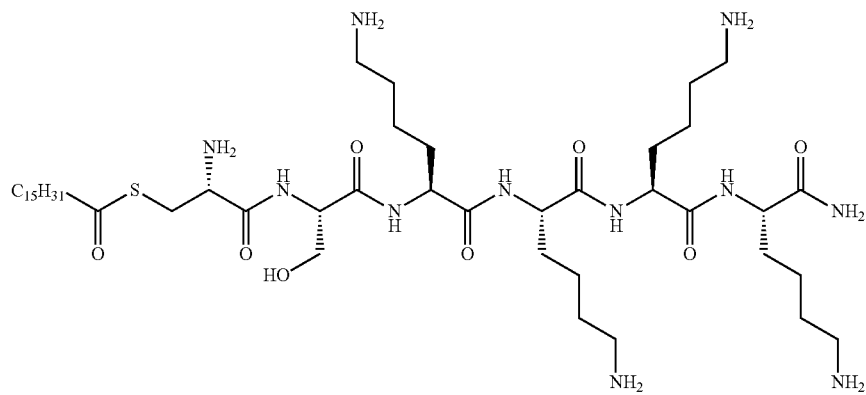

Thiol-ene reaction product of Cys-Ser-Lys-Lys-Lys-Lys-$NH_2$ [SEQ ID NO: 103] and vinyl palmitate 20

The thiol-ene reaction of crude Cys-Ser-Lys-Lys-Lys-Lys-$NH_2$ with 5 eq. vinyl palmitate, 0.4 eq. DMPA in NMP, 1 hr irradiation at 365 nm gives the desired product 20 (Pam-$CSK_4$), the identity of which is determined by MS analysis.

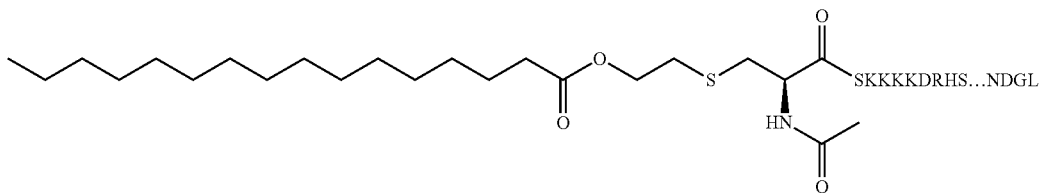

Thiol-ene reaction product of AcN-Cys-Ser-Lys-Lys-Lys-Lys-Asp-Arg-His-Ser-Asp-Tyr-Gln-Pro-Leu-Gly-Thr-Gln-Asp-Gln-Ser-Leu-Tyr-Leu-Gly-Leu-Gln-His-Asp-Gly-Asn-Asp-Gly-Leu-OH 25 [SEQ ID NO: 102] and vinyl palmitate 26

To crude peptide 25 (20 mg) and DMPA (1.2 mg, 4.74 µmol) in a solution of NMP (3 mL) is added vinyl palmitate (19.2 µL, 59.3 µmol). The resultant mixture is irradiated, with agitation, at 365 nm for 1 hr in a standard photochemical apparatus. The desired product 26 is detected by mass analysis. The crude product 26 is purified via semi-preparative RP HPLC on a Phenomenex Gemini C18 column running a gradient of 5-65% MeCN:$H_2O$+0.1% TFA (3% MeCN per min, 50° C.). Mass spectrometry is used to confirm the structure of the desired product 26 and the oxidised Met(O) by-product.

1.5 General Method for Thiol-Ene Reaction on Peptides

To crude or purified peptide (10 mM), DTT (30 mM) and DMPA (4 mM) in a solution of DMSO is added vinyl palmitate (50 mM). The resultant mixture is irradiated, with agitation, at 365 nm for 15 min in a standard UV photo-chemical apparatus. The desired product is detected by ESI mass analysis. To achieve full conversion, further addition of DMPA photoinitiator is sometimes required. The crude product is purified via semi-preparative RP HPLC on a Phenomenex Gemini C18 column running a gradient of 1-65% MeCN:$H_2O$+0.1% TFA (3% MeCN per min). Pooled fractions are lyophilised to afford the pure products as white powders.

1.6 Discussion

The thermal reaction of Fmoc-Cys-OH with vinyl palmitate is conducted in 1,2-dichloroethane, using 5 equivalents of alkene and 0.2 eq. of AIBN as radical initiator.

The reaction is performed under reflux (90 degrees) for 24 hrs. Microwave heating (100 W, 1 hr) is also used in certain embodiments. The desired product is detected by TLC. A number of by-products are in some embodiments also formed.

Photo-initiation of the reaction is conducted with 1 eq. vinyl palmitate and 0.2 eq. DMPA as the photo-initiator. Reactions are conducted in a degassed DMF:DCM solvent mixture, irradiated for 1 hr with 365 nm UV light in a standard photo-chemical apparatus. Near complete conversion of the Fmoc-Cys-OH is monitored by TLC. Desirably, minimal by-products are formed. Purification provides the product 200 in about reasonable to high yield. Using 2 eq. vinyl palmitate provides 200 in high yield after purification.

The thiol-ene reaction is carried out using NAc-CSK$_4$. The required peptide motif 24 is synthesised as described above. Following attachment of Rink-Amide linker to aminomethyl resin, the SK$_4$ sequence is built up using automated Fmoc-SPPS (standard coupling conditions). Fmoc-Cys(Trt)-OH is then coupled manually using conditions to reduce epimerisation. N-acetylation is then carried out.

Mass analysis is used to establish whether by-product formation is occurring upon cleavage of the peptide from the resin, due to tert-butylation (+56) of cysteine. Repeating the synthesis of NAc-CSK$_4$ utilising Fmoc-Ser(Trt)-OH, instead of Fmoc-Ser(t-Bu)-OH, is used in certain embodiments to produce a product free of the cysteine-alkylation product. The peptide is cleaved and then lyophilised.

The thiol-ene reaction of crude peptide 24 with vinyl palmitate is then carried out. N-methylpyrrolidone (NMP) effectively solvates both the hydrophilic CSK$_4$ peptide and the hydrophobic vinyl palmitate molecule.

Thermal initiation using AIBN and microwave heating is carried out on both crude and purified peptide using excess of vinyl palmitate (up to 20 eq.). Photo-initiation of the reaction will in certain embodiments provide better results. Using crude peptide with DMPA as photo-initiator, the reaction will in certain embodiments proceed to completion following 1 hr of irradiation (5 eq. vinyl palmitate, 0.4 eq. DMPA in 2 mL NMP). The desired product is confirmed by MS (ideally, >90% conversion, 60% purity by HPLC).

Advantageously, no purification after cleavage is required before the thiol-ene coupling. Purification by RP-HPLC is typically inefficient, with >50% loss of material being common. Generally, it is advantageous to reduce the number of HPLC purification steps required wherever possible.

Purification of the N-acetylated monoacyl lipopeptide 22 is achieved by semi-preparative RP-HPLC using a Phenomenex C18 column, running a gradient of 5-95% MeCN:$H_2O$+0.1% TFA, 3% MeCN per min. The purified peptide is then lyophilised to afford the desired product as a white powder.

Increasing the peptide concentration to 25 mM will in certain embodiments lead to a small decrease in by-product formation (for example, >90% conversion, 80% purity by HPLC). Decreasing the concentration to 5 mM will in certain cases have the opposite effect.

Carrying out the reaction in a mixture of NMP:$H_2O$:DMSO (4:2:1) in the presence of glutathione (GSH)(3 eq.) with a peptide concentration of 5 mM will in certain cases result in mixed disulfide formation (for example, 50% conversion, 75% purity by HPLC). Using 2,2'-(ethylenedioxy)diethanethiol (DODT)(3 eq.) in NMP with a peptide concentration of 5 mM will in certain cases lead to a complex mixture of products (for example, 80% conversion by HPLC).

In certain embodiments, addition of 3 eq. DTT to the reaction mixture (10 mM peptide in NMP) leads to no by-products resulting from vinyl palmitate telomerisation, or mixed disulfides, being observed and the reaction proceeds with high conversion (for example, >90% conversion, 85% purity by HPLC). Using DTT it is also possible to conduct the reaction (25 mM peptide) in DMSO, a benign and more versatile solvent (for example, to achieve 90% conversion, >95% purity by HPLC).

The thiol-ene reaction is also carried out using non-acetylated analogue CSK$_4$. Synthesis of the CSK$_4$ motif is carried out utilising the procedure described above. The peptide is then cleaved from resin and lyophilised. In certain embodiments, the thiol-ene reaction of the crude product with vinyl palmitate proceeds smoothly using 5 eq. vinyl palmitate, 0.4 eq. DMPA in NMP, 1 hr irradiation at 365 nm to give the desired product 20 (Pam-CSK$_4$), the identity of which is confirmed by MS analysis.

The thiol-ene reaction of vinyl palmitate with a long peptide comprising EBV LMP2 epitopes, LMP2 S-1 [SEQ ID NO: 5], is also carried out.

The LMP2 S-1 sequence is built up by automated Fmoc-SPPS, using standard conditions. A K$_4$ tag and a serine residue are then coupled to the N-terminus of the sequence, as depicted herein as SEQ ID NO: 4. The peptidyl resin is then removed from the synthesiser and the cysteine residue coupled manually, using standard conditions. N-acetylation is then carried out. The peptide is then cleaved from the resin and lyophilised to give a white powder in good yield.

The thiol-ene reaction of the unprotected peptide 25 and vinyl palmitate is carried out using photo-initiation, as described for peptides 20 and 22. Mass analysis is performed to establish conversion to the palmitoylated product 26. Purification is accomplished by semi-preparative RP-HPLC using a Phenomenex C18 column, running a gradient of 5-95% MeCN:H$_2$O with 0.1% TFA. The purified peptide is lyophilised to provide the desired product as a white powder, along with the corresponding Met(O) product.

The thiol-ene reaction of crude 25 with vinyl palmitate is also carried out following the general procedure described above. ESI-MS and HPLC analysis are performed to establish good conversion to the palmitoylated product 26. Purification is accomplished by semi-preparative RP-HPLC, to give the desired product, for example in >95% purity.

Example 2. Biological Activity of Peptide Conjugates 20, 22, and 26

2.1 Procedures
Activation of Human Monocytes in Whole Blood

100 µl of heparinised whole blood (WB) is incubated with 100 nM, 1 µM and 10 µM of each compound, in duplicate, and incubated overnight at 37° C. in a 5% CO$_2$ humidified incubator. Pam$_3$CSK$_4$ (10 µM; EMC Microcollections) is used as a positive control. To detect activation of monocytes, WB samples are stained with anti-CD14-FITC, anti-HLA-DR-Alexa700, anti-CD80-PE-Cy7, anti-CD40-PE, anti-CD86-APC, anti-CD16-APC-Cy7 (all from Biolegend) for 20 mins at RT, protected from light. Following incubation, 2 ml of BD FACS lyse (BD Biosciences) is added, incubated for 15 mins at RT, then washed twice with ice cold wash buffer (PBS, 1% Human Serum). Data acquisition is performed on a BD FACS Aria II (Becton Dickinson) and analysed using FlowJo software version 7.6.5 (TreeStar). CD80 receptor expression on monocytes is detected by gating on CD14+ HLADR+ cells.
Toll-Like Receptor 2 (TLR2) Agonism Using HekBlue Cells HEK-Blue™-hTLR2 and HEK-Blue™-mTLR2 are purchased from Invivogen. These HEK-Blue cells are produced by co-transfection of both reporter gene SEAP (secreted embryonic alkaline phosphatase) and either human or murine TLR2, respectively. The SEAP reporter gene is under the control of the IFN-β minimal promoter fused to five AP-1 and five NFkB binding sites. Cells are cultured according to manufacturer's instructions. On the day of the assay, the constructs are added at the selected concentrations in 20 µl volume of endotoxin free water in a 96-well plate. HEK-Blue™-hTLR2 or HEK-Blue™-hTLR2 cells are resuspended at ~2.83×10$^4$ cells/ml in HEK-Blue™ Detection medium and immediately add 180 ml of the cell suspension (~5×10$^4$ cells per well.) The cells are incubated overnight at 37° C. in 5% CO$_2$. SEAP expression was quantified using an EnSpire plate reader (PerkinElmer) at 635 nM.
Method for Detection of IL-8 Secretion from TLR2-Transiently Transfected Hek293 Cells Hek-293 cells are plated 3×10$^4$ cells in 50 µl per well in 96-well plate with DMEM containing 10% FBS (the medium is not supplemented with antibiotics). Cells are transfected with either a combination of pFLAG-TLR2 plasmid and pcDNA3.1 (a kind gift from Shimizu, as reported in Shimizu, T., Y. Kida and K. Kuwano (2005). "A dipalmitoylated lipoprotein from *Mycoplasma pneumoniae* activates NF-kappa B through TLR1, TLR2, and TLR6." J Immunol 175(7): 4641-4646), or the control plasmid only (pcDNA3.1). Master mix of Lipofectamine/DNA complexes are constituted in Opti-MEM at 100 ngDNA in 0.3 µl Lipofectamine in a volume of 50 µl per sample. Following an incubation of 20 mins, the plasmid mix was added to the cells. Protein expression was induced for 24 hours prior to the addition of constructs.

The constructs are added to the wells at the selected concentrations to make a final volume of 200 µl per well. Following 18-hours of stimulation, the supernatant was harvested from each sample and stored at −20° C. until required. IL-8 secretion is determined by Cytometric Bead Array (BD Biosciences) according to manufacturer's protocol, optionally with one modification: 25 µl of conditioned medium can be used instead of 50 µl. To accurately determine the concentration of secreted IL-8, an 11-point standard curve (1-5000 ng/ml) is performed. Samples are analysed using a BD-FACS Aria II (BD Biosciences) and the data is then analysed using FCAP ARRAY Software (version 1.0.1).

2.2 Discussion

The bioactivity of lipopeptides 20, 22, and 26, is assessed by flow cytometry to measure up-regulation of the co-stimulatory molecule CD80 on human monocytes in fresh blood samples.

Monocytes are identified in donor samples by characteristic cell surface markers, and the expression of CD80 determined before and after exposure to each compound at three dosages, with commercially available Pam3CSK4 (10 µM) serving as a positive control.

Results showing test lipopeptides 20, 22 and 26 strongly upregulate expression of CD80 at all doses tested, for example at equivalent or greater potency to positive control Pam3CSK4, are indicative of effective TLR agonism.

Results showing test lipopeptides 20, 22 and 26 demonstrate TLR agonism in HekBlue™ and IL-8 reporter systems, for example, titratable TLR agonism, are indicative of effective TLR agonism.

Results showing high potency of 20, 22 and 26 are supportive of the finding that conjugation of antigenic peptides does not affect TLR2 agonism.

Example 3. Preparation of Conjugates 200, 120, 121, 110-112, 112A, and 113-116

3.1 General Details

Protected amino acids and coupling reagents are purchased from GL-Biochem (Shanghai). The resins used in the solid-supported syntheses are preloaded tentagel resins from Rapp Polymere GmbH (Tuebingen) and other solvents and reagents are obtained from Sigma (St Louis, Mo.) and Novabiochem.

The peptide syntheses described below are carried out using standard iterative Fmoc Solid-Phase Peptide Synthesis techniques on a Tribute peptide synthesiser (Protein Technologies International, Tucson, Ariz.). A typical deprotection and coupling cycle carried out on a 0.1 mmol scale entails removal of the Fmoc protecting group from the resin-bound amino-acid using two treatments of 20% piperidine in DMF (4 mL×5 min) then washing the resin with DMF. In a separate vessel the Fmoc amino acid (0.5 mmol) and coupling agent (1-[bis(dimethylamino)methylene]-1H-1,2,3-triazolo[4,5-b]pyridinium 3-oxide hexafluorophosphate (HATU), 0.45 mmol) are dissolved in DMF (1.5 mL) and base (4-methylmorpholine, 1 mmol) is added. After mixing for 1 minute, this solution is transferred to the resin, which is agitated at RT for 1 hour, drained and washed.

Cleavage of the peptide (0.1 mmol scale) is achieved by suspending the resin in 5 mL trifluoroacetic acid (TFA) containing 5% (v/v) ethanedithiol (EDT) and agitating at room room temperature for 3 hours. Triisopropylsilane (TIPS) is then added to 1% (v/v) and agitation continued for a further five minutes before draining the TFA into chilled diethyl ether (40 mL). The precipitated material is pelleted by centrifugation, the ether discarded, the pellet washed once with ether (25 mL) and air-dried or lyophilised.

Reverse phase (RP)-HPLC is carried out using a Dionex Ultimate 3000 HPLC system. For semi-preparative purifications, a peptide sample is injected into a reverse-phase Phenomenex Gemini C18 column (5µ, 110 Å; 10×250 mm) equilibrated in a suitable mixture of eluent A (water/0.1% TFA) and eluent B (MeCN/0.1% TFA) then an increasing gradient of eluent B is generated to elute the constituent components. Analytical HPLC is performed similarly, using a Phenomenex Gemini C18 column (3µ, 110 Å; 4.6×150 mm).

Low-resolution mass spectra are obtained using an Agilent Technologies 6120 Quadrapole mass spectrometer.

NMR spectra are obtained using a Bruker BRX400 spectrometer operating at 400 MHz for $^1$H NMR and at 100 MHz for $^{13}$C NMR.

In the amino acid conjugates and peptide conjugates described below the abbreviations AcN-C(Pam-1)- and H$_2$N—C(Pam-1)- means

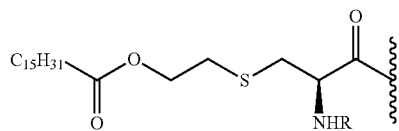

wherein R is Ac or H as appropriate.

3.2 Preparation of Peptide Conjugates by Direct Conjugation

Peptides

Peptides 100 and 102 (comprising LMP2 S-2, SEQ ID NO: 10), 103 and 104 (comprising LMP2 S-3, SEQ ID NO: 15), and 105 and 106 (comprising LMP2 5-2, SEQ ID NO: 30), as depicted in Table 3 below are synthesised as described and depicted below (Scheme 1).

Scheme 1

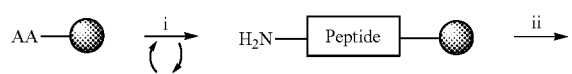

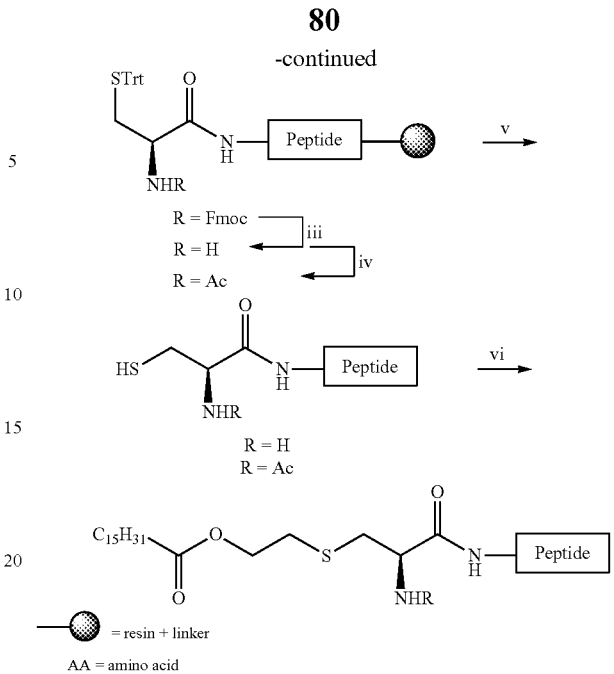

(i) Iterative Fmoc-SPPS; (ii) Fmoc-Cys(Trt)-OH, HATU, NMM, DMF; (iii) 20% piperidine/DMF; (iv) Ac$_2$O/NMM, DMF; (v) TFA/EDT; (vi) vinylpalmitate, DTT, DMPA, NMP, 365nm.

Following synthesis of the peptide sequence up to the penultimate amino acid using iterative Fmoc-SPPS, Fmoc-cysteine is introduced as the N-terminal residue of the on-resin peptide by reaction with Fmoc-Cys(Trt)-OH, HATU, and 4-methylmorpholine in DMF. The Fmoc group is removed using 20% piperidine in DMF. As required, the resulting amine group is converted to an acetamide by treatment with a mixture of 20% acetic anhydride in DMF (2 mL) and 4-methylmorpholine (1 mmol).

Following cleavage of the peptide from resin with TFA/EDT and its precipitation in ether, the solid is dissolved in 1:1 water/MeCN and lyophilised. If the peptide contained a methionine residue the solution is heated at 60° C. for 1 hour prior to freeze-drying to reverse any S-alkylation that may have occurred during cleavage. The peptides are then purified by RP-HPLC to give material of >95%.

TABLE 3

| | Sequence | SEQ ID NO: |
|---|---|---|
| 100 | AcHN-CSKKKKSLYLGLQHDGNDGLPPPPYSPRDDSSQHIYEEA(Ac)-C(O)NH2 | 104 |
| 102 | AcHN-CSKKKKSLYLGLQHDGNDGLPPPPYSPRDDSSQHIYEEA-OH | 104 |
| 103 | H$_2$N-CSKKKKSDYQPLGTQDQSLYLGLQHDGNDGL-OH | 105 |
| 104 | AcHN-CSKKKKSDYQPLGTQDQSLYLGLQHDGNDGL-OH | 105 |
| 105 | H$_2$N-CSKKKKLMLLWTLVVLLICSSCSSCPLSKILLARLFLYALALLLLA-OH | 106 |
| 106 | AcHN-CSKKKK LMLLWTLVVLLICSSCSSCPLSKILLARLFLYALALLLLA-OH | 106 |

Peptide Conjugates

The thiol-ene reaction is then performed on peptides 100 and 102-106 to generate the corresponding peptide conjugates 110, 112, and 113-116 (Table 4).

DMPA (2.6 mg), dithiothreitol (9.2 mg), and vinyl palmitate (40 mg, mmol) are dissolved in degassed NMP (2 mL). 100 µL of this solution is then added to 1 µmol of the peptide weighed into a small polypropylene vessel to give a solution containing 10 mM peptide, 5 mM DMPA, 30 mM DTT and 50 mM vinyl palmitate. NMP is compatible with the reaction conditions and effectively solvates all of the components of the reaction mixture.

The reaction vessel is flushed with nitrogen and the vigorously stirred mixture irridiated with a hand-held 6 watt UV lamp (Spectronics, NY) operating at 365 nm. After 30 minutes the reaction is analysed by HPLC and conversion to the desired product is determined. The product is then isolated by RP-HPLC and unreacted starting material recovered.

The peptides with non-acetylated N-terminal cysteine will in certain embodiments form significant amounts of the disulfide dimer, despite the presence of the reducing agent DTT. This is not typically observed with the corresponding N-acetylated peptides.

Peptide conjugates 110 and 113-116 are also prepared from peptides 100 and 103-106 by the following alternative procedure (Table 4B).

In this procedure, tert-butyl mercaptan (tBuSH) thiol is used in place of DTT. In certain embodiments, this result in increased and cleaner conversion of the substrate peptides to the desired peptide conjugate.

Trifluoroacetic acid (TFA) is also introduced to the reaction mixture. In certain embodiments, this further improves the reaction profile. The formation of oligomers, minor by-products formed by reaction of the product peptide conjugate with a second molecule of vinyl palmitate to give a bis-palmitoylated species, is largely suppressed by the addition of TFA.

Any apparent propensity of methionine to oxidise to the corresponding sulfoxide under these conditions, can be resolved by lypophilising the crude product mixtures of those peptides possessing methionine groups, followed by dissolution in TFA and treatment with tetrabutylammonium iodide to reduce methionine oxide back to methionine.

A typical procedure is as follows. DMPA (6.5 mg) is dissolved in degassed NMP (0.5 mL) and tert-butyl mercaptan (17 µL) added and in a separate vessel vinyl palmitate (11.3 mg) is dissolved in degassed N-methylpyrrolidinone (NMP) (0.5 mL). The peptide (1 µmol) is weighed into a small polypropylene vessel equipped with a small stirrer and 10 µL of the DMPA/tBuSH solution added followed by 100 µL of the vinyl palmitate solution, to give a solution of approximately 10 mM peptide, 5 mM DMPA, 30 mM DTT and 80 mM vinyl palmitate. TFA (5.5 µL) is then added, to give a 5% solution. The reaction vessel is flushed with nitrogen and the vigorously stirred mixture irradiated with a hand-held 6 watt UV lamp (Spectronics, NY) operating at 365 nm. After 20 minutes further DMPA (10 µL) and vinyl palmitate (50 µL) are added and irradiation continued for 20 min.

For those peptides containing methionine, water (0.5 mL) and MeCN (0.5 mL) are added and the mixture lyophilised. The resultant solid is dissolved in neat TFA (150 µL), cooled to 0° C. and tetra-n-butylammonium iodide (3.7 mg, 10 µmol) in 25 µL TFA is added. After 1 minute chilled diethyl ether (0.5 mL) is added to precipitate the reduced lipopeptide, which is pelleted by centrifugation and lyophilised.

The reactions are analysed by HPLC to show conversion to the desired products (Table 4B), which are then isolated by RP-HPLC.

TABLE 4

| Sequence | SEQ ID NO: |
|---|---|
| 110 AcHN-C(Pam-1)SKKKSLYLGLQHDGNDGLPPPPYSPRDDSSQHIYEEA(Ac)-C(O)NH₂ | 104 |
| 112 AcHN-C(Pam-1)SKKKKSLYLGLQHDGNDGLPPPPYSPRDDSSQHIYEEA-OH<sup>a</sup> | 104 |
| 113 H₂N-C(Pam-1)SKKKKSDYQPLGTQDQSLYLGLQHDGNDGL-OH | 105 |
| 114 AcHN-C(Pam-1)SKKKKSDYQPLGTQDQSLYLGLQHDGNDGL-OH | 105 |
| 115 H₂N-C(Pam-1)SKKKKLMLLWTLVVLLICSSCSSCPLSKILLARLFLYALALLLLA-OH | 106 |
| 116 AcHN-C(Pam-1)SKKKKLMLLWTLVVLLICSSCSSCPLSKILLARLFLYALALLLLA-OH | 106 |

TABLE 4B

| Sequence | SEQ ID NO: |
|---|---|
| 110 AcHN-C(Pam-1)SKKKSLYLGLQHDGNDGLPPPPYSPRDDSSQHIYEEA(Ac)-C(O)NH2 | 104 |
| 113 H2N-C(Pam-1)SKKKKSDYQPLGTQDQSLYLGLQHDGNDGL-OH | 105 |
| 114 AcHN-C(Pam-1)SKKKKSDYQPLGTQDQSLYLGLQHDGNDGL-OH | 105 |
| 116 AcHN-C(Pam-1)SKKKKLMLLWTLVVLLICSSCSSCPLSKILLARLFLYALALLLLA-OH | 106 |

3.3 Preparation of Amino Acid Conjugates

Amino acid conjugates 200, 120, and 121 are prepared from N-α-Fmoc-, N-α-acetyl-, and N-α-Boc-protected cysteine, respectively, as described and depicted below (Scheme 2).

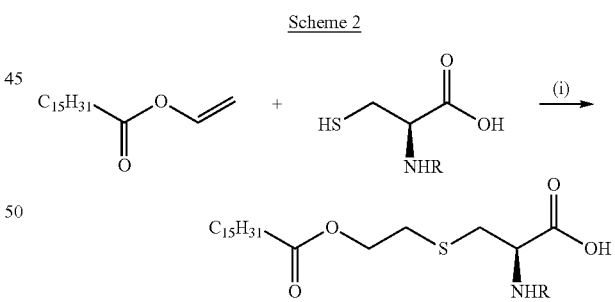

Scheme 2

R = Fmoc, R = Ac, R = Boc
200 R = Fmoc; 120 R = Ac; 121 R = Boc
(i) Radical initiator, hu (365 nm) or heat Solid N-α-protected cysteine is dissolved or suspended to a concentration of 100 mg/mL in the indicated solvent (Table 5) and vinyl palmitate (1.5 molar equivalents) added followed by the indicated quantity of initiator. For reactions conducted under photolytic conditions the solution is prepared in a polypropylene vessel, DMPA added in the indicated molar proportions (Table 5) and the stirred mixture then irradiated at 365 nm. For reactions carried out under thermal conditions, the solution is prepared in a glass tube, the indicated quantity of AIBN (azobisisobutyronitrile) added and the stirred mixture heated either in an oil bath or in a microwave oven.

Reaction progress is monitored using thin-layer chromatography and is allowed to proceed to completion based on consumption of the cysteine starting material. The solvent is then removed and the residue purified by flash column chromatography on silica gel, eluting with hexane/ethyl acetate mixtures. The identities of Fmoc-Cys(Pam-1)-OH (200), Ac-Cys(Pam-1)-OH (120) and Boc-Cys(Pam-1)-OH (121), are confirmed by $^1$H and $^{13}$C NMR and by mass spectrometry.

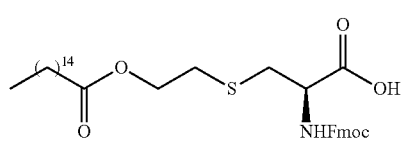

N-Fmoc-Cys(Pam-1)-OH (200)

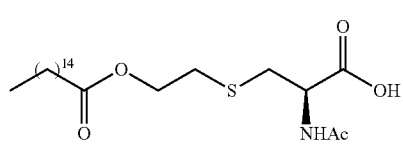

N-Ac-Cys(Pam-1)-OH (120)

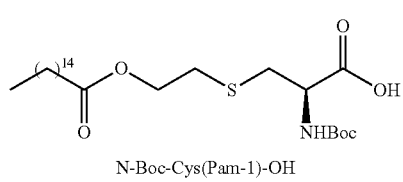

N-Boc-Cys(Pam-1)-OH (121)

The conjugation reaction is carried out under a variety of conditions, which are summarized in Table 5.

TABLE 5

| Entry | N-α-protecting group | Initiator (mol eq.) | Solvent | Conditions[a] | Time (min) |
| --- | --- | --- | --- | --- | --- |
| 1 | Fmoc | DMPA (0.2) | DCM | hu (365 nm) | 60 |
| 2 | Fmoc | DMPA (1) | DCM | hu (365 nm) | 60 |
| 3 | Fmoc | AIBN (1) | DCM | Microwave (70° C.) | 80 |
| 4 | Ac | DMPA (0.2) | DCM | hu (365 nm) | 60 |
| 5 | Ac | DMPA (0.2) | DCM | hu (365 nm), DTT | 60 |
| 6 | Ac | DMPA (1) | DCM | hu (365 nm) | 60 |
| 7 | Ac | AIBN (1) | DCM | Microwave (70° C.) | 80 |
| 8 | Boc | DMPA (0.2) | DCM | hu (365 nm) | 60 |
| 9 | Boc | DMPA (1) | DCM | hu (365 nm) | 60 |
| 10 | Boc | AIBN (1) | DCM | Microwave (70° C.) | 80 |

[a]UV irradiation used a hand-held Spectronics 6 watt lamp operating at 365 nm; microwave reactions are carried out using a CEM Discover microwave reactor operating at 100 w and 70° C.

The use of photolytic conditions or thermal conditions will in certain embodiments generate the desired products with desirably high yields.

3.4 Preparation of Peptide Conjugates Via Coupling of Amino Add Conjugates

Peptide conjugates 110-116 are prepared as described and depicted below (Scheme 3).

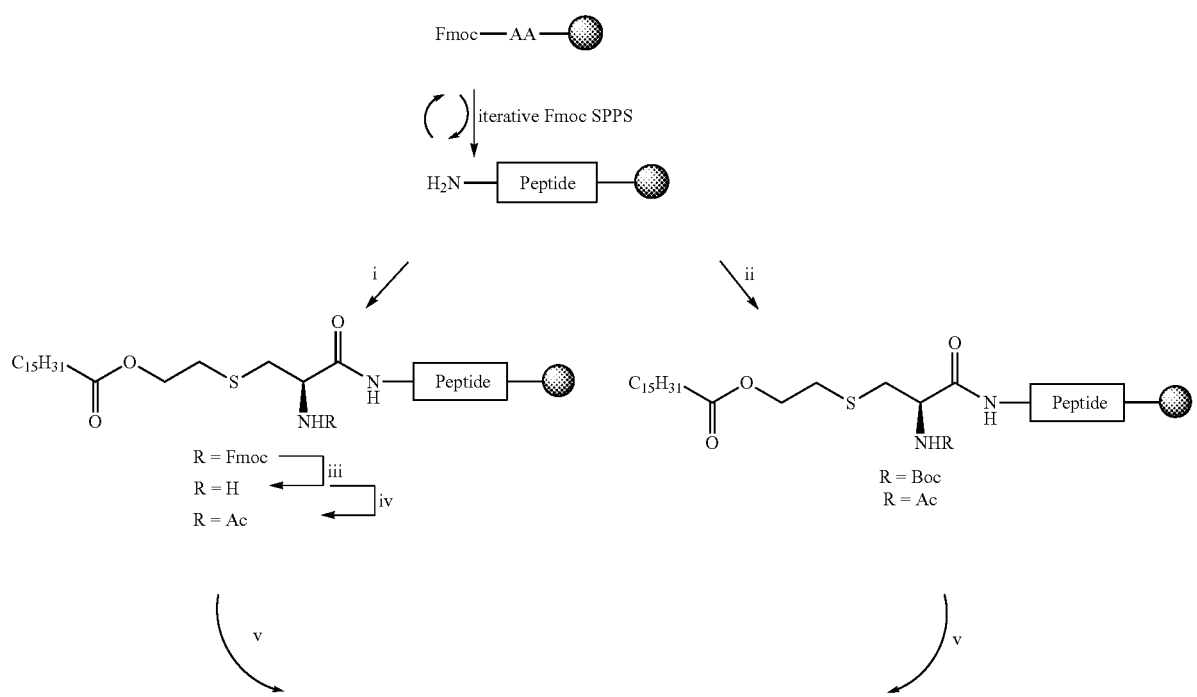

-continued

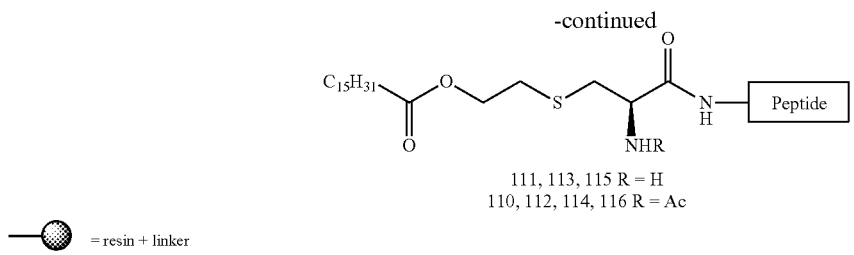

111, 113, 115 R = H
110, 112, 114, 116 R = Ac

—⬤ = resin + linker (i) Iterative Fmoc-SPPS; (ii) Fmoc-Cys(Pam-1)-OH (200), PyBOP, collidine, DMF; (iii) Ac-Cys(Pam-1-)-OH (120) or Boc- Cys(Pam-1)-OH (121), PyBOP, collidine, DMF; (iv) 20% piperidine/DMF; (v) Ac2O/NMM, DMF; (vi) TFA/EDT.

The desired peptide sequence is synthesised using standard iterative Fmoc SPPS techniques using a Tribute peptide synthesiser as previously described. After coupling the penultimate amino acid residue, the resin-bound peptide chain is then derivatised with the amino acid conjugate N-Fmoc-Cys(Pam-1)-OH 200 using PyBOP and collidine in DMF. The Fmoc group is then removed using 20% piperidine in DMF.

The resulting peptide is then cleaved from resin using TFA/EDT, with concomitant removal of protecting groups, to afford peptide conjugates 111, 113 and 115.

Alternatively, the resulting peptide is converted to the corresponding acetamide by treatment with a mixture of 20% acetic anhydride in DMF (2 mL) and 4-methylmorpholine (1 mmol) and then cleaved from resin to afford peptide conjugates 110, 112, 114 and 116.

Alternatively, the resin-bound peptides are derivatised with either the amino acid conjugate N-Boc-Cys(Pam-1)-OH 121 or N—Ac-Cys(Pam-1)-OH 120. On cleavage from resin this affords the peptide conjugates 110-116 directly, without the additional manipulations necessary due to the Fmoc group.

The conditions for coupling of the amino acid conjugate advantageously reduces the propensity of the α-carbon of the amino acid to racemise on activation. The amino acid conjugate (0.075 mmol) and PyBOP (benzotriazol-1-yloxytripyrrolidinophosphonium hexafluorophosphate) (0.1 mmol) are combined and dissolved in DMF (0.3 mL). Neat 2,4,6-trimethylpyridine (0.1 mmol) is added and after mixing for 30 seconds the solution transferred to 0.025 mmol of resin, which is then agitated for 90 minutes, drained and washed (DMF).

The peptide is then cleaved by agitating 0.015 mmol of the resin in 1 mL of trifluoroacetic acid containing 5% (v/v) ethanedithiol at room temperature for 3 hours. The supernatant is then drained through a sinter into chilled diethyl ether (10 mL) and the resin is washed with a further 1 mL of TFA, which is also added to the ether.

The precipitated material is pelleted by centrifugation and the pellet washed once with ether (5 mL) before being dissolved in 1:1 MeCN/Water (+0.1% tfa) and lyophilised. If the peptide contained a methionine residue the solution is heated at 60° C. for 1 hour prior to freeze-drying. The peptides are then purified (>95%) by RP-HPLC and their identities confirmed by analytical RP-HPLC and mass spectrometry.

Example 4. Analysis of Peptides LMP2 S1 & LMP2 S2

1.1 General Details

Peptides LMP2 S1 (DRHSDYQPLGTQDQS-LYLGLQHDGNDGL, SEQ ID NO: 5) and LMP2 S2 (SLYLGLQHDGNDGLPPPPYSPRDDSSQHIYEEA, SEQ ID NO: 10) were synthesised essentially as described above. The peptides were then purified (>95%) by RP-HPLC and their identities confirmed by analytical RP-HPLC and mass spectrometry.

Results

FIG. 1 shows an RP-HPLC trace of LMP2 S1, under the following conditions: column: Phenomenex Gemini C18 (5μ 110 Å, 4.6×150 mm); gradient: 0-1 min, 5% B then 5% B to 65% B over 30 min., eluting at 1 mL/min., Rt 14.4 min.

ESI-MS trace m/z [M+2H]2+=1572.7.

Figure 2:
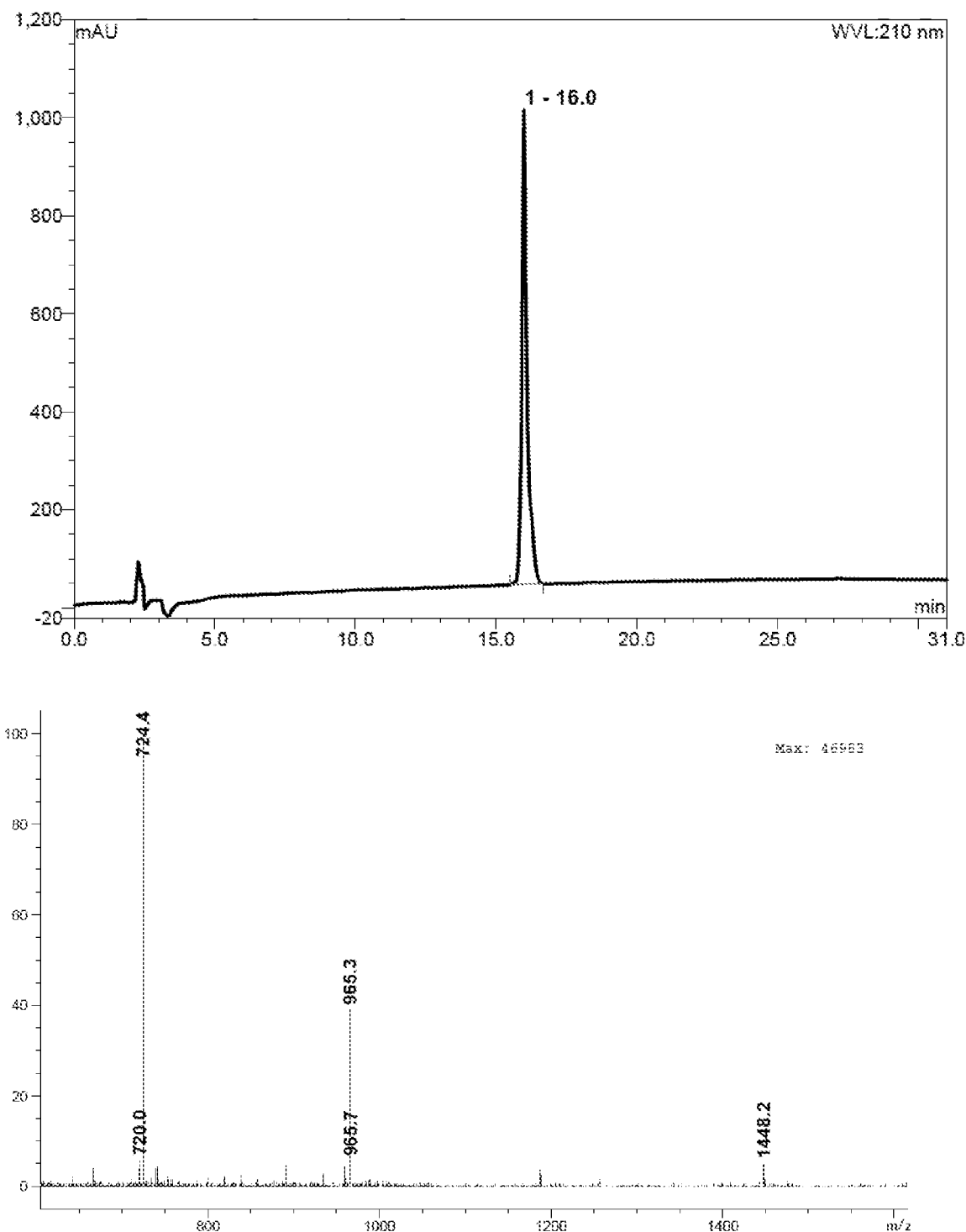
FIG. 2 shows an RP-HPLC trace of LMP2 S2, as described herein in Example 4.

FIG. 2 shows an RP-HPLC trace of LMP2 S2, under the following conditions: column: Phenomenex Gemini C18 (5μ 110 Å, 4.6×150 mm); gradient: 0-1 min, 1% B then 1% B to 61% B over 30 min., eluting at 1 mL/min., Rt 16.0 min.

ESI-MS trace m/z [M+2H]2+=1448.2.

Example 5. Analysis of Conjugated LMP2 S4(SK4)

1.1 General Details

Peptide LMP2 S4(SK4)

(SKKKKSDYQPLGTQDQSLYLGLQHDGNDGLPPP-PYSPRDDSSQHIYEEA, SEQ ID NO: 19) was synthesised, acetylated and conjugated to Pam1Cys essentially as described above, to give Pam1-C(Ac)SK4-LMP2 S4 [SEQ ID NO: 107]:

The identity of the crude peptide was then confirmed by analytical RP-HPLC and mass spectrometry.

Results

Figure 3:
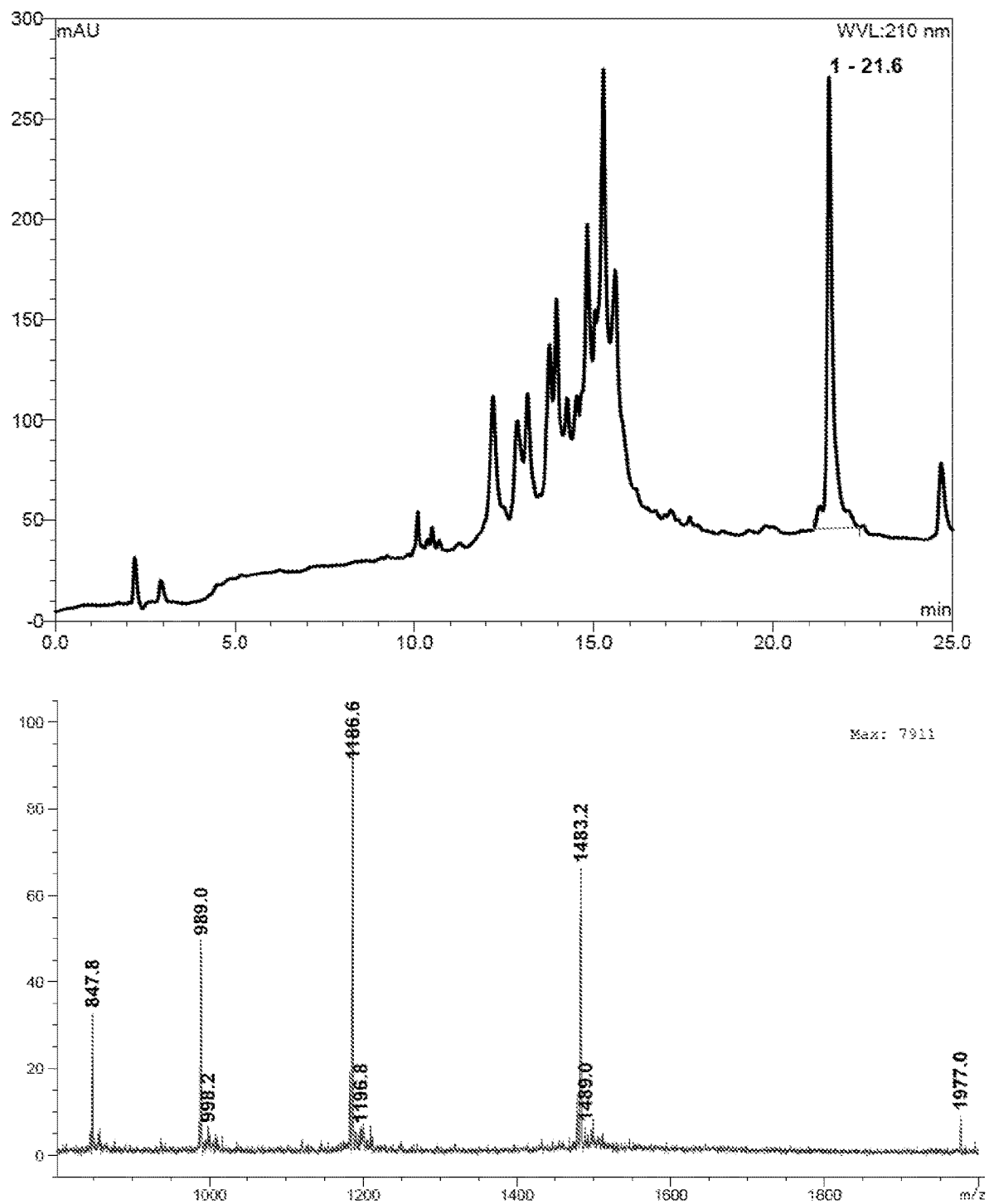
FIG. 3 shows an RP-HPLC trace of Pam1-C(Ac)SK4-LMP2 S4, as described herein in Example 5.

FIG. 3 shows an RP-HPLC trace of Pam1-C(Ac)SK4-LMP2 S4, under the following conditions: column: Phenomenex Gemini C18 (5µ 110 Å, 4.6×150 mm); gradient: 0-1 min, 5% B then 5% B to 65% B over 30 min., eluting at 1 mL/min., Rt 21.6 min.

ESI-MS trace m/z [M+3H]3+=1977.0 It is not the intention to limit the scope of the invention to the abovementioned examples only. As would be appreciated by a skilled person in the art, many variations are possible without departing from the scope of the invention.

INDUSTRIAL APPLICABILITY

The peptides, and amino acid and peptide conjugates and compositions and constructs of the invention find application in the pharmaceutical and medical fields, including application in methods of eliciting immune responses in a subject and methods of vaccinating a subject. For example, medicaments comprising the peptides or amino acid and peptide conjugates directed to treating Epstein Barr Virus (EBV) associated diseases, such as Hodgkin's Disease (HD) or Nasopharangeal Carcinoma (NPC), including, for example, self-adjuvating vaccines comprising one or more epitopes from EBV Latent Membrane Protein 2 (LMP2), are particularly contemplated.

The invention claimed is:

1. A compound of the formula (V):

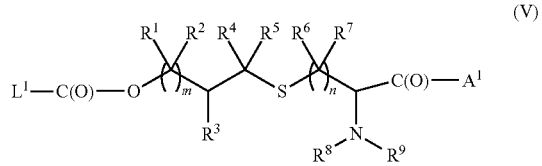

wherein m is an integer from 0 to 4;

n is 1 or 2;

R1 and R2 at each instance of m are each independently hydrogen, C1-6alkyl, or C3-6cycloalkyl;

R3, R4, R5, R8, and R9 are each independently hydrogen, C1-6alkyl, or C3-6cycloalkyl; or R9 is an amino protecting group, L3-C(O), or A2;

R6 and R7 at each instance of n are each independently hydrogen, C1-6alkyl, or C3-6cycloalkyl, L1 is C5-21alkyl or C4-20heteroalkyl;

L3 is C1-6alkyl or C3-6cycloalkyl;

A1 and A2 are each independently an amino acid or a peptide; or A1 is OH or OP1, wherein P1 is a carboxyl protecting group; and wherein A1 comprises one or more EBV LMP2 epitopes or R9 is A2 and comprises one or more EBV LMP2 epitopes, or wherein (i) A1 comprises one or more peptides selected from the group consisting of SEQ ID NOs: 1-101, (ii) R9 is A2 and comprises one or more peptides selected from the group consisting of SEQ ID NOs: 1-101, or (iii) A1 comprises one or more peptides selected from the group consisting of SEQ ID NOs: 1-101 and R9 is A2 and comprises one or more peptides selected from the group consisting of SEQ ID NOs: 1-101;

wherein any alkyl, cycloalkyl or heteroalkyl present in any of R1, R2, R4, R5, R6, R7, R8, R9, L1, and L3 and any cycloalkyl in R3 is optionally substituted with one or more substituents independently selected from the group consisting of halo, CN, NO2, OH, NH2, NH (C1-6alkyl), N (C1-6alkyl) (C1-6alkyl), C1-6haloalkyl, C1-6haloalkoxy, C(O)NH2, C(O)NH (C1-6alkyl), C(O)N(C1-6alkyl) (C1-6alkyl), SO2 (C1-6alkyl), O(C1-6alkyl), S(C1-6alkyl), S(O)(C1-6alkyl), C(O)(C1-6alkyl), and C1-6aliphatic, or a pharmaceutically acceptable salt or solvate thereof.

2. The compound of claim 1, wherein R9 is independently hydrogen, C1-6alkyl, or C3-C6cycloalkyl; or R9 is L3-C(O) or A2; and A1 and A2 are each independently a peptide; or A1 is OH; provided that:

at least one of A1 and A2 comprises an EBV LMP2 epitope; and when R9 is not A2, A1 is a peptide.

3. The compound of claim 1, wherein L1 is C5-21alkyl or linear C15alkyl.

4. The compound of claim 1, wherein m is an integer from 0 to 2 or m is 0 or 1.

5. The compound of claim 1, wherein m is 0.

6. The compound of claim 1, wherein R1 and R2 at each instance of m are each independently hydrogen.

7. The compound of claim 1, wherein R3 is hydrogen.

8. The compound of claim 1, wherein R4 and R5 are each hydrogen.

9. The compound of claim 1, wherein R6 and R7 Eire each hydrogen.

10. The compound of claim 1, wherein R8 is hydrogen and R9 is hydrogen, an amino protecting group, L3-C(O), or A2.

11. The compound of claim 1, wherein L3 is Me.

12. The compound of claim 1, wherein the peptide comprises an epitope selected from the group consisting of the amino acid sequence of any one of SEQ ID NOs: 76-101.

13. The compound of claim 1, wherein A1 is serine or a peptide comprising serine as the first N-terminal amino acid residue.

14. The compound of claim 1, wherein A1 and/or A2 is a peptide comprising a solubilising group comprising an amino acid sequence comprising two or more hydrophilic amino acid residues in the peptide chain.

15. The compound of claim 1 wherein the peptide comprises, consists essentially of, or consists of an amino acid sequence selected from the group consisting of a. 8 or more contiguous amino acid residues from the sequence of any one of SEQ ID NO:1 to 101;
b. 10 or more contiguous amino acid residues from the sequence of any one of SEQ ID NO:1 to 101;
c. 12 or more contiguous amino acid residues from the sequence of any one of SEQ ID NO:1 to 101;
d. 15 or more contiguous amino acid residues from the sequence of any one of SEQ ID NO:1 to 101;
e. 20 or more contiguous amino acid residues from the sequence of any one of SEQ ID NO:1 to 101;
f. the sequence of any one of SEQ ID NOs: 1 to 101,
g. 8 or more contiguous amino acid residues from the sequence of any one of SEQ ID NO:1 to 93;
h. 10 or more contiguous amino acid residues from the sequence of any one of SEQ ID NO:1 to 93;
12 or more contiguous amino acid residues from the sequence of any one of SEQ ID NO:1 to 93;
15 or more contiguous amino acid residues from the sequence of any one of SEQ ID NO:1 to 93;
k. 20 or more contiguous amino acid residues from the sequence of any one of SEQ ID NO:1 to 93;
l. the sequence of any one of SEQ ID NOS: 1 to 93,
m. 8 or more contiguous amino acid residues from the sequence of any one of SEQ ID NO:1 to 75;
n. 10 or more contiguous amino acid residues from the sequence of any one of SEQ ID NO:1 to 75;
o. 12 or more contiguous amino acid residues from the sequence of any one of SEQ ID NO:1 to 75;
p. 15 or more contiguous amino acid residues from the sequence of any one of SEQ ID NO:1 to 75;
q. 20 or more contiguous amino acid residues from the sequence of any one of SEQ ID NO:1 to 75;
r. the sequence of any one of SEQ ID NOs: 1 to 75, and
s. any combination of two or more of (a) to (r) above.

16. A pharmaceutical composition comprising an effective amount of a peptide conjugate of claim 1 or a pharmaceutically acceptable salt or solvate thereof, or any combination thereof, and a pharmaceutically acceptable carrier.

17. A method of vaccinating or eliciting an immune response in a subject comprising administering to the subject an effective amount of a peptide conjugate of claim 1 or a pharmaceutically acceptable salt or solvate thereof.

18. A method for making a peptide conjugate of claim 1, the method comprising
(A) reacting
   a lipid-containing conjugation partner, and
   an amino acid-comprising conjugation partner,
   under conditions effective to conjugate the lipid-containing conjugation partner to the amino acid-comprising conjugation partner by the hydrothiolation of a carbon-carbon double bond with a thiol,
   the method further comprising coupling the amino acid of the amino acid conjugate to an amino acid or a peptide to provide a peptide conjugate, and wherein the peptide conjugate comprises one or more EBV LMP2 epitopes; or
(B) reacting
   lipid-containing conjugation partner, and
   a peptide-comprising conjugation partner, wherein the peptide-comprising partner comprises one or more EBV LMP2 epitopes,
   under conditions effective to conjugate the lipid-containing conjugation partner to the peptide-comprising conjugation partner by the hydrothiolation of a carbon-carbon double bond with a thiol; or
(C) providing a lipididated amino acid or peptide, and coupling the lipidated amino acid or peptide to one or more amino acids or peptides to provide a peptide conjugate, and wherein the peptide conjugate comprises one or more EBV LMP2 epitopes.

* * * * *

SEQUENCE LISTING

```
<160> NUMBER OF SEQ ID NOS: 107

<210> SEQ ID NO 1
<211> LENGTH: 48
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S or a hydrophilic amino
      acid
<220> FEATURE:
<221> NAME/KEY: MISC_FEATURE
<222> LOCATION: (2)..(2)
<223> OTHER INFORMATION: Xaa2 is absent or is a hydrophilic amino acid
<220> FEATURE:
<221> NAME/KEY: MISC_FEATURE
<222> LOCATION: (3)..(3)
<223> OTHER INFORMATION: Xaa3 is absent or is a hydrophilic amino acid
<220> FEATURE:
<221> NAME/KEY: MISC_FEATURE
<222> LOCATION: (4)..(4)
<223> OTHER INFORMATION: Xaa4 is absent or is a hydrophilic amino acid
<220> FEATURE:
<221> NAME/KEY: MISC_FEATURE
<222> LOCATION: (5)..(5)
<223> OTHER INFORMATION: Xaa5 is absent or is a hydrophilic amino acid
<220> FEATURE:
<221> NAME/KEY: MISC_FEATURE
<222> LOCATION: (6)..(6)
<223> OTHER INFORMATION: Xaa6 is absent or is a hydrophilic amino acid
<220> FEATURE:
<221> NAME/KEY: MISC_FEATURE
<222> LOCATION: (7)..(7)
<223> OTHER INFORMATION: Xaa7 is absent or is a hydrophilic amino acid
<220> FEATURE:
<221> NAME/KEY: MISC_FEATURE
<222> LOCATION: (8)..(8)
<223> OTHER INFORMATION: Xaa8 is absent or is a hydrophilic amino acid
<220> FEATURE:
<221> NAME/KEY: MISC_FEATURE
<222> LOCATION: (9)..(9)
<223> OTHER INFORMATION: Xaa9 is absent or is a hydrophilic amino acid
<220> FEATURE:
<221> NAME/KEY: MISC_FEATURE
<222> LOCATION: (10)..(10)
<223> OTHER INFORMATION: Xaa10 is absent or is a hydrophilic amino acid
<220> FEATURE:
<221> NAME/KEY: MISC_FEATURE
<222> LOCATION: (11)..(11)
<223> OTHER INFORMATION: Xaa11 is absent or is a hydrophilic amino acid
<220> FEATURE:
<221> NAME/KEY: MISC_FEATURE
<222> LOCATION: (12)..(12)
<223> OTHER INFORMATION: Xaa12 is absent or is a hydrophilic amino acid
<220> FEATURE:
<221> NAME/KEY: MISC_FEATURE
<222> LOCATION: (13)..(13)
<223> OTHER INFORMATION: Xaa13 is absent or is a hydrophilic amino acid
<220> FEATURE:
```

```
<221> NAME/KEY: MISC_FEATURE
<222> LOCATION: (14)..(14)
<223> OTHER INFORMATION: Xaa14 is absent or is a hydrophilic amino acid
<220> FEATURE:
<221> NAME/KEY: MISC_FEATURE
<222> LOCATION: (15)..(15)
<223> OTHER INFORMATION: Xaa15 is absent or is a hydrophilic amino acid
<220> FEATURE:
<221> NAME/KEY: MISC_FEATURE
<222> LOCATION: (16)..(16)
<223> OTHER INFORMATION: Xaa16 is absent or is a hydrophilic amino acid
<220> FEATURE:
<221> NAME/KEY: MISC_FEATURE
<222> LOCATION: (17)..(17)
<223> OTHER INFORMATION: Xaa17 is absent or is a hydrophilic amino acid
<220> FEATURE:
<221> NAME/KEY: MISC_FEATURE
<222> LOCATION: (18)..(18)
<223> OTHER INFORMATION: Xaa18 is absent or is a hydrophilic amino acid
<220> FEATURE:
<221> NAME/KEY: MISC_FEATURE
<222> LOCATION: (19)..(19)
<223> OTHER INFORMATION: Xaa19 is absent or is a hydrophilic amino acid
<220> FEATURE:
<221> NAME/KEY: MISC_FEATURE
<222> LOCATION: (20)..(20)
<223> OTHER INFORMATION: Xaa20 is absent or is a hydrophilic amino acid

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Asp Arg His Ser Asp Tyr Gln Pro Leu Gly Thr Gln
            20                  25                  30

Asp Gln Ser Leu Tyr Leu Gly Leu Gln His Asp Gly Asn Asp Gly Leu
        35                  40                  45

<210> SEQ ID NO 2
<211> LENGTH: 40
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S or is a hydrophilic
      amino acid
<220> FEATURE:
<221> NAME/KEY: MISC_FEATURE
<222> LOCATION: (2)..(2)
<223> OTHER INFORMATION: Xaa2 is absent or is a hydrophilic amino acid
<220> FEATURE:
<221> NAME/KEY: MISC_FEATURE
<222> LOCATION: (3)..(3)
<223> OTHER INFORMATION: Xaa3 is absent or is a hydrophilic amino acid
<220> FEATURE:
<221> NAME/KEY: MISC_FEATURE
<222> LOCATION: (4)..(4)
<223> OTHER INFORMATION: Xaa4 is absent or is a hydrophilic amino acid
<220> FEATURE:
<221> NAME/KEY: MISC_FEATURE
<222> LOCATION: (5)..(5)
<223> OTHER INFORMATION: Xaa5 is absent or is a hydrophilic amino acid
<220> FEATURE:
<221> NAME/KEY: MISC_FEATURE
<222> LOCATION: (6)..(6)
<223> OTHER INFORMATION: Xaa6 is absent or is a hydrophilic amino acid
<220> FEATURE:
<221> NAME/KEY: MISC_FEATURE
<222> LOCATION: (7)..(7)
<223> OTHER INFORMATION: Xaa7 is absent or is a hydrophilic amino acid
<220> FEATURE:
<221> NAME/KEY: MISC_FEATURE
<222> LOCATION: (8)..(8)
<223> OTHER INFORMATION: Xaa8 is absent or is a hydrophilic amino acid
```

```
<220> FEATURE:
<221> NAME/KEY: MISC_FEATURE
<222> LOCATION: (9)..(9)
<223> OTHER INFORMATION: Xaa9 is absent or is a hydrophilic amino acid
<220> FEATURE:
<221> NAME/KEY: MISC_FEATURE
<222> LOCATION: (10)..(10)
<223> OTHER INFORMATION: Xaa10 is absent or is a hydrophilic amino acid
<220> FEATURE:
<221> NAME/KEY: MISC_FEATURE
<222> LOCATION: (11)..(11)
<223> OTHER INFORMATION: Xaa11 is absent or is a hydrophilic amino acid
<220> FEATURE:
<221> NAME/KEY: MISC_FEATURE
<222> LOCATION: (12)..(12)
<223> OTHER INFORMATION: Xaa12 is absent or is a hydrophilic amino acid

<400> SEQUENCE: 2

Xaa Xaa Xaa Xaa Xaa Xaa Xaa Xaa Xaa Xaa Xaa Xaa Asp Arg His Ser
1               5                   10                  15

Asp Tyr Gln Pro Leu Gly Thr Gln Asp Gln Ser Leu Tyr Leu Gly Leu
                20                  25                  30

Gln His Asp Gly Asn Asp Gly Leu
            35                  40

<210> SEQ ID NO 3
<211> LENGTH: 33
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S or a hydrophilic amino
      acid
<220> FEATURE:
<221> NAME/KEY: MISC_FEATURE
<222> LOCATION: (2)..(2)
<223> OTHER INFORMATION: Xaa2 is absent or is a hydrophilic amino acid
<220> FEATURE:
<221> NAME/KEY: MISC_FEATURE
<222> LOCATION: (3)..(3)
<223> OTHER INFORMATION: Xaa3 is absent or is a hydrophilic amino acid
<220> FEATURE:
<221> NAME/KEY: MISC_FEATURE
<222> LOCATION: (4)..(4)
<223> OTHER INFORMATION: Xaa4 is absent or is a hydrophilic amino acid
<220> FEATURE:
<221> NAME/KEY: MISC_FEATURE
<222> LOCATION: (5)..(5)
<223> OTHER INFORMATION: Xaa5 is absent or is a hydrophilic amino acid

<400> SEQUENCE: 3

Xaa Xaa Xaa Xaa Xaa Asp Arg His Ser Asp Tyr Gln Pro Leu Gly Thr
1               5                   10                  15

Gln Asp Gln Ser Leu Tyr Leu Gly Leu Gln His Asp Gly Asn Asp Gly
                20                  25                  30

Leu

<210> SEQ ID NO 4
<211> LENGTH: 33
<212> TYPE: PRT
<213> ORGANISM: Artificial
<220> FEATURE:
<223> OTHER INFORMATION: Synthetic peptide sequence

<400> SEQUENCE: 4

Ser Lys Lys Lys Lys Asp Arg His Ser Asp Tyr Gln Pro Leu Gly Thr
1               5                   10                  15
```

Gln Asp Gln Ser Leu Tyr Leu Gly Leu Gln His Asp Gly Asn Asp Gly
            20                  25                  30

Leu

<210> SEQ ID NO 5
<211> LENGTH: 28
<212> TYPE: PRT
<213> ORGANISM: Artificial
<220> FEATURE:
<223> OTHER INFORMATION: Synthetic peptide sequence

<400> SEQUENCE: 5

Asp Arg His Ser Asp Tyr Gln Pro Leu Gly Thr Gln Asp Gln Ser Leu
1               5                   10                  15

Tyr Leu Gly Leu Gln His Asp Gly Asn Asp Gly Leu
            20                  25

<210> SEQ ID NO 6
<211> LENGTH: 53
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S or a hydrophilic amino
      acid
<220> FEATURE:
<221> NAME/KEY: MISC_FEATURE
<222> LOCATION: (2)..(2)
<223> OTHER INFORMATION: Xaa2 is absent or is a hydrophilic amino acid
<220> FEATURE:
<221> NAME/KEY: MISC_FEATURE
<222> LOCATION: (3)..(3)
<223> OTHER INFORMATION: Xaa3 is absent or is a hydrophilic amino acid
<220> FEATURE:
<221> NAME/KEY: MISC_FEATURE
<222> LOCATION: (4)..(4)
<223> OTHER INFORMATION: Xaa4 is absent or is a hydrophilic amino acid
<220> FEATURE:
<221> NAME/KEY: MISC_FEATURE
<222> LOCATION: (5)..(5)
<223> OTHER INFORMATION: Xaa5 is absent or is a hydrophilic amino acid
<220> FEATURE:
<221> NAME/KEY: MISC_FEATURE
<222> LOCATION: (6)..(6)
<223> OTHER INFORMATION: Xaa6 is absent or is a hydrophilic amino acid
<220> FEATURE:
<221> NAME/KEY: MISC_FEATURE
<222> LOCATION: (7)..(7)
<223> OTHER INFORMATION: Xaa7 is absent or is a hydrophilic amino acid
<220> FEATURE:
<221> NAME/KEY: MISC_FEATURE
<222> LOCATION: (8)..(8)
<223> OTHER INFORMATION: Xaa8 is absent or is a hydrophilic amino acid
<220> FEATURE:
<221> NAME/KEY: MISC_FEATURE
<222> LOCATION: (9)..(9)
<223> OTHER INFORMATION: Xaa9 is absent or is a hydrophilic amino acid
<220> FEATURE:
<221> NAME/KEY: MISC_FEATURE
<222> LOCATION: (10)..(10)
<223> OTHER INFORMATION: Xaa10 is absent or is a hydrophilic amino acid
<220> FEATURE:
<221> NAME/KEY: MISC_FEATURE
<222> LOCATION: (11)..(11)
<223> OTHER INFORMATION: Xaa11 is absent or is a hydrophilic amino acid
<220> FEATURE:
<221> NAME/KEY: MISC_FEATURE
<222> LOCATION: (12)..(12)
<223> OTHER INFORMATION: Xaa12 is absent or is a hydrophilic amino acid
<220> FEATURE:

```
<221> NAME/KEY: MISC_FEATURE
<222> LOCATION: (13)..(13)
<223> OTHER INFORMATION: Xaa13 is absent or is a hydrophilic amino acid
<220> FEATURE:
<221> NAME/KEY: MISC_FEATURE
<222> LOCATION: (14)..(14)
<223> OTHER INFORMATION: Xaa14 is absent or is a hydrophilic amino acid
<220> FEATURE:
<221> NAME/KEY: MISC_FEATURE
<222> LOCATION: (15)..(15)
<223> OTHER INFORMATION: Xaa15 is absent or is a hydrophilic amino acid
<220> FEATURE:
<221> NAME/KEY: MISC_FEATURE
<222> LOCATION: (16)..(16)
<223> OTHER INFORMATION: Xaa16 is absent or is a hydrophilic amino acid
<220> FEATURE:
<221> NAME/KEY: MISC_FEATURE
<222> LOCATION: (17)..(17)
<223> OTHER INFORMATION: Xaa17 is absent or is a hydrophilic amino acid
<220> FEATURE:
<221> NAME/KEY: MISC_FEATURE
<222> LOCATION: (18)..(18)
<223> OTHER INFORMATION: Xaa18 is absent or is a hydrophilic amino acid
<220> FEATURE:
<221> NAME/KEY: MISC_FEATURE
<222> LOCATION: (19)..(19)
<223> OTHER INFORMATION: Xaa19 is absent or is a hydrophilic amino acid
<220> FEATURE:
<221> NAME/KEY: MISC_FEATURE
<222> LOCATION: (20)..(20)
<223> OTHER INFORMATION: Xaa20 is absent or is a hydrophilic amino acid

<400> SEQUENCE: 6

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Ser Leu Tyr Leu Gly Leu Gln His Asp Gly Asn Asp
            20                  25                  30

Gly Leu Pro Pro Pro Pro Tyr Ser Pro Arg Asp Asp Ser Ser Gln His
        35                  40                  45

Ile Tyr Glu Glu Ala
    50

<210> SEQ ID NO 7
<211> LENGTH: 45
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S or a hydrophilic amino
      acid
<220> FEATURE:
<221> NAME/KEY: MISC_FEATURE
<222> LOCATION: (2)..(2)
<223> OTHER INFORMATION: Xaa2 is absent or a hydrophilic amino acid
<220> FEATURE:
<221> NAME/KEY: MISC_FEATURE
<222> LOCATION: (3)..(3)
<223> OTHER INFORMATION: Xaa3 is absent or a hydrophilic amino acid
<220> FEATURE:
<221> NAME/KEY: MISC_FEATURE
<222> LOCATION: (4)..(4)
<223> OTHER INFORMATION: Xaa4 is absent or a hydrophilic amino acid
<220> FEATURE:
<221> NAME/KEY: MISC_FEATURE
<222> LOCATION: (5)..(5)
<223> OTHER INFORMATION: Xaa5 is absent or a hydrophilic amino acid
<220> FEATURE:
<221> NAME/KEY: MISC_FEATURE
<222> LOCATION: (6)..(6)
<223> OTHER INFORMATION: Xaa6 is absent or a hydrophilic amino acid
<220> FEATURE:
```

```
<221> NAME/KEY: MISC_FEATURE
<222> LOCATION: (7)..(7)
<223> OTHER INFORMATION: Xaa7 is absent or a hydrophilic amino acid
<220> FEATURE:
<221> NAME/KEY: MISC_FEATURE
<222> LOCATION: (8)..(8)
<223> OTHER INFORMATION: Xaa8 is absent or a hydrophilic amino acid
<220> FEATURE:
<221> NAME/KEY: MISC_FEATURE
<222> LOCATION: (9)..(9)
<223> OTHER INFORMATION: Xaa9 is absent or a hydrophilic amino acid
<220> FEATURE:
<221> NAME/KEY: MISC_FEATURE
<222> LOCATION: (10)..(10)
<223> OTHER INFORMATION: Xaa10 is absent or a hydrophilic amino acid
<220> FEATURE:
<221> NAME/KEY: MISC_FEATURE
<222> LOCATION: (11)..(11)
<223> OTHER INFORMATION: Xaa11 is absent or a hydrophilic amino acid
<220> FEATURE:
<221> NAME/KEY: MISC_FEATURE
<222> LOCATION: (12)..(12)
<223> OTHER INFORMATION: Xaa12 is absent or a hydrophilic amino acid

<400> SEQUENCE: 7

Xaa Xaa Xaa Xaa Xaa Xaa Xaa Xaa Xaa Xaa Xaa Xaa Ser Leu Tyr Leu
1               5                   10                  15

Gly Leu Gln His Asp Gly Asn Asp Gly Leu Pro Pro Pro Tyr Ser
            20                  25                  30

Pro Arg Asp Asp Ser Ser Gln His Ile Tyr Glu Glu Ala
        35                  40                  45

<210> SEQ ID NO 8
<211> LENGTH: 38
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S or a hydrophilic amino
      acid
<220> FEATURE:
<221> NAME/KEY: MISC_FEATURE
<222> LOCATION: (2)..(2)
<223> OTHER INFORMATION: Xaa2 is absent or is a hydrophilic amino acid
<220> FEATURE:
<221> NAME/KEY: MISC_FEATURE
<222> LOCATION: (3)..(3)
<223> OTHER INFORMATION: Xaa3 is absent or is a hydrophilic amino acid
<220> FEATURE:
<221> NAME/KEY: MISC_FEATURE
<222> LOCATION: (4)..(4)
<223> OTHER INFORMATION: Xaa4 is absent or is a hydrophilic amino acid
<220> FEATURE:
<221> NAME/KEY: MISC_FEATURE
<222> LOCATION: (5)..(5)
<223> OTHER INFORMATION: Xaa5 is absent or is a hydrophilic amino acid

<400> SEQUENCE: 8

Xaa Xaa Xaa Xaa Xaa Ser Leu Tyr Leu Gly Leu Gln His Asp Gly Asn
1               5                   10                  15

Asp Gly Leu Pro Pro Pro Tyr Ser Pro Arg Asp Asp Ser Ser Gln
            20                  25                  30

His Ile Tyr Glu Glu Ala
        35

<210> SEQ ID NO 9
<211> LENGTH: 38
<212> TYPE: PRT
```

<213> ORGANISM: Artificial
<220> FEATURE:
<223> OTHER INFORMATION: Synthetic peptide sequence

<400> SEQUENCE: 9

Ser Lys Lys Lys Lys Ser Leu Tyr Leu Gly Leu Gln His Asp Gly Asn
1               5                   10                  15

Asp Gly Leu Pro Pro Pro Tyr Ser Pro Arg Asp Asp Ser Ser Gln
            20              25                  30

His Ile Tyr Glu Glu Ala
        35

<210> SEQ ID NO 10
<211> LENGTH: 33
<212> TYPE: PRT
<213> ORGANISM: Artificial
<220> FEATURE:
<223> OTHER INFORMATION: Synthetic peptide sequence

<400> SEQUENCE: 10

Ser Leu Tyr Leu Gly Leu Gln His Asp Gly Asn Asp Gly Leu Pro Pro
1               5                   10                  15

Pro Pro Tyr Ser Pro Arg Asp Asp Ser Ser Gln His Ile Tyr Glu Glu
            20              25                  30

Ala

<210> SEQ ID NO 11
<211> LENGTH: 45
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S or a hydrophilic amino
      acid
<220> FEATURE:
<221> NAME/KEY: MISC_FEATURE
<222> LOCATION: (2)..(2)
<223> OTHER INFORMATION: Xaa2 is absent or is a hydrophilic amino acid
<220> FEATURE:
<221> NAME/KEY: MISC_FEATURE
<222> LOCATION: (3)..(3)
<223> OTHER INFORMATION: Xaa3 is absent or is a hydrophilic amino acid
<220> FEATURE:
<221> NAME/KEY: MISC_FEATURE
<222> LOCATION: (4)..(4)
<223> OTHER INFORMATION: Xaa4 is absent or is a hydrophilic amino acid
<220> FEATURE:
<221> NAME/KEY: MISC_FEATURE
<222> LOCATION: (5)..(5)
<223> OTHER INFORMATION: Xaa5 is absent or is a hydrophilic amino acid
<220> FEATURE:
<221> NAME/KEY: MISC_FEATURE
<222> LOCATION: (6)..(6)
<223> OTHER INFORMATION: Xaa6 is absent or is a hydrophilic amino acid
<220> FEATURE:
<221> NAME/KEY: MISC_FEATURE
<222> LOCATION: (7)..(7)
<223> OTHER INFORMATION: Xaa7 is absent or is a hydrophilic amino acid
<220> FEATURE:
<221> NAME/KEY: MISC_FEATURE
<222> LOCATION: (8)..(8)
<223> OTHER INFORMATION: Xaa8 is absent or is a hydrophilic amino acid
<220> FEATURE:
<221> NAME/KEY: MISC_FEATURE
<222> LOCATION: (9)..(9)
<223> OTHER INFORMATION: Xaa9 is absent or is a hydrophilic amino acid
<220> FEATURE:
<221> NAME/KEY: MISC_FEATURE

```
<222> LOCATION: (10)..(10)
<223> OTHER INFORMATION: Xaa10 is absent or is a hydrophilic amino acid
<220> FEATURE:
<221> NAME/KEY: MISC_FEATURE
<222> LOCATION: (11)..(11)
<223> OTHER INFORMATION: Xaa11 is absent or is a hydrophilic amino acid
<220> FEATURE:
<221> NAME/KEY: MISC_FEATURE
<222> LOCATION: (12)..(12)
<223> OTHER INFORMATION: Xaa12 is absent or is a hydrophilic amino acid
<220> FEATURE:
<221> NAME/KEY: MISC_FEATURE
<222> LOCATION: (13)..(13)
<223> OTHER INFORMATION: Xaa13 is absent or is a hydrophilic amino acid
<220> FEATURE:
<221> NAME/KEY: MISC_FEATURE
<222> LOCATION: (14)..(14)
<223> OTHER INFORMATION: Xaa14 is absent or is a hydrophilic amino acid
<220> FEATURE:
<221> NAME/KEY: MISC_FEATURE
<222> LOCATION: (15)..(15)
<223> OTHER INFORMATION: Xaa15 is absent or is a hydrophilic amino acid
<220> FEATURE:
<221> NAME/KEY: MISC_FEATURE
<222> LOCATION: (16)..(16)
<223> OTHER INFORMATION: Xaa16 is absent or is a hydrophilic amino acid
<220> FEATURE:
<221> NAME/KEY: MISC_FEATURE
<222> LOCATION: (17)..(17)
<223> OTHER INFORMATION: Xaa17 is absent or is a hydrophilic amino acid
<220> FEATURE:
<221> NAME/KEY: MISC_FEATURE
<222> LOCATION: (18)..(18)
<223> OTHER INFORMATION: Xaa18 is absent or is a hydrophilic amino acid
<220> FEATURE:
<221> NAME/KEY: MISC_FEATURE
<222> LOCATION: (19)..(19)
<223> OTHER INFORMATION: Xaa19 is absent or is a hydrophilic amino acid
<220> FEATURE:
<221> NAME/KEY: MISC_FEATURE
<222> LOCATION: (20)..(20)
<223> OTHER INFORMATION: Xaa20 is absent or is a hydrophilic amino acid

<400> SEQUENCE: 11

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Ser Asp Tyr Gln Pro Leu Gly Thr Gln Asp Gln Ser
            20                  25                  30

Leu Tyr Leu Gly Leu Gln His Asp Gly Asn Asp Gly Leu
        35                  40                  45

<210> SEQ ID NO 12
<211> LENGTH: 37
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S or a hydrophilic amino
      acid
<220> FEATURE:
<221> NAME/KEY: MISC_FEATURE
<222> LOCATION: (2)..(2)
<223> OTHER INFORMATION: Xaa2 is absent or is a hydrophilic amino acid
<220> FEATURE:
<221> NAME/KEY: MISC_FEATURE
<222> LOCATION: (3)..(3)
<223> OTHER INFORMATION: Xaa3 is absent or is a hydrophilic amino acid
<220> FEATURE:
<221> NAME/KEY: MISC_FEATURE
<222> LOCATION: (4)..(4)
<223> OTHER INFORMATION: Xaa4 is absent or is a hydrophilic amino acid
<220> FEATURE:
```

```
<221> NAME/KEY: MISC_FEATURE
<222> LOCATION: (5)..(5)
<223> OTHER INFORMATION: Xaa5 is absent or is a hydrophilic amino acid
<220> FEATURE:
<221> NAME/KEY: MISC_FEATURE
<222> LOCATION: (6)..(6)
<223> OTHER INFORMATION: Xaa6 is absent or is a hydrophilic amino acid
<220> FEATURE:
<221> NAME/KEY: MISC_FEATURE
<222> LOCATION: (7)..(7)
<223> OTHER INFORMATION: Xaa7 is absent or is a hydrophilic amino acid
<220> FEATURE:
<221> NAME/KEY: MISC_FEATURE
<222> LOCATION: (8)..(8)
<223> OTHER INFORMATION: Xaa8 is absent or is a hydrophilic amino acid
<220> FEATURE:
<221> NAME/KEY: MISC_FEATURE
<222> LOCATION: (9)..(9)
<223> OTHER INFORMATION: Xaa9 is absent or is a hydrophilic amino acid
<220> FEATURE:
<221> NAME/KEY: MISC_FEATURE
<222> LOCATION: (10)..(10)
<223> OTHER INFORMATION: Xaa10 is absent or is a hydrophilic amino acid
<220> FEATURE:
<221> NAME/KEY: MISC_FEATURE
<222> LOCATION: (11)..(11)
<223> OTHER INFORMATION: Xaa11 is absent or is a hydrophilic amino acid
<220> FEATURE:
<221> NAME/KEY: MISC_FEATURE
<222> LOCATION: (12)..(12)
<223> OTHER INFORMATION: Xaa11 is absent or is a hydrophilic amino acid

<400> SEQUENCE: 12

Xaa Xaa Xaa Xaa Xaa Xaa Xaa Xaa Xaa Xaa Xaa Xaa Ser Asp Tyr Gln
1               5                   10                  15

Pro Leu Gly Thr Gln Asp Gln Ser Leu Tyr Leu Gly Leu Gln His Asp
            20                  25                  30

Gly Asn Asp Gly Leu
        35

<210> SEQ ID NO 13
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S or a hydrophilic amino
      acid
<220> FEATURE:
<221> NAME/KEY: MISC_FEATURE
<222> LOCATION: (2)..(2)
<223> OTHER INFORMATION: Xaa2 is absent or is a hydrophilic amino acid
<220> FEATURE:
<221> NAME/KEY: MISC_FEATURE
<222> LOCATION: (3)..(3)
<223> OTHER INFORMATION: Xaa3 is absent or is a hydrophilic amino acid
<220> FEATURE:
<221> NAME/KEY: MISC_FEATURE
<222> LOCATION: (4)..(4)
<223> OTHER INFORMATION: Xaa4 is absent or is a hydrophilic amino acid
<220> FEATURE:
<221> NAME/KEY: MISC_FEATURE
<222> LOCATION: (5)..(5)
<223> OTHER INFORMATION: Xaa5 is absent or is a hydrophilic amino acid

<400> SEQUENCE: 13

Xaa Xaa Xaa Xaa Xaa Ser Asp Tyr Gln Pro Leu Gly Thr Gln Asp Gln
1               5                   10                  15

Ser Leu Tyr Leu Gly Leu Gln His Asp Gly Asn Asp Gly Leu
            20                  25                  30
```

```
<210> SEQ ID NO 14
<211> LENGTH: 30
<212> TYPE: PRT
<213> ORGANISM: Artificial
<220> FEATURE:
<223> OTHER INFORMATION: Synthetic peptide sequence

<400> SEQUENCE: 14

Ser Lys Lys Lys Lys Ser Asp Tyr Gln Pro Leu Gly Thr Gln Asp Gln
1               5                   10                  15

Ser Leu Tyr Leu Gly Leu Gln His Asp Gly Asn Asp Gly Leu
            20                  25                  30

<210> SEQ ID NO 15
<211> LENGTH: 25
<212> TYPE: PRT
<213> ORGANISM: Artificial
<220> FEATURE:
<223> OTHER INFORMATION: Synthetic peptide sequence

<400> SEQUENCE: 15

Ser Asp Tyr Gln Pro Leu Gly Thr Gln Asp Gln Ser Leu Tyr Leu Gly
1               5                   10                  15

Leu Gln His Asp Gly Asn Asp Gly Leu
            20                  25

<210> SEQ ID NO 16
<211> LENGTH: 51
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 16

Xaa Xaa Xaa Xaa Asp Arg His Ser Asp Tyr Gln Pro Leu Gly Thr Gln
1               5                   10                  15

Asp Gln Ser Leu Tyr Leu Gly Leu Gln His Asp Gly Asn Asp Gly Leu
            20                  25                  30

Pro Pro Pro Pro Tyr Ser Pro Arg Asp Asp Ser Ser Gln His Ile Tyr
            35                  40                  45

Glu Glu Ala
    50

<210> SEQ ID NO 17
<211> LENGTH: 50
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 17

Xaa Xaa Xaa Asp Arg His Ser Asp Tyr Gln Pro Leu Gly Thr Gln Asp
1               5                   10                  15

Gln Ser Leu Tyr Leu Gly Leu Gln His Asp Gly Asn Asp Gly Leu Pro
            20                  25                  30
```

```
Pro Pro Pro Tyr Ser Pro Arg Asp Asp Ser Ser Gln His Ile Tyr Glu
        35                  40                  45

Glu Ala
    50

<210> SEQ ID NO 18
<211> LENGTH: 49
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 18

Xaa Xaa Asp Arg His Ser Asp Tyr Gln Pro Leu Gly Thr Gln Asp Gln
1               5                   10                  15

Ser Leu Tyr Leu Gly Leu Gln His Asp Gly Asn Asp Gly Leu Pro Pro
            20                  25                  30

Pro Pro Tyr Ser Pro Arg Asp Asp Ser Ser Gln His Ile Tyr Glu Glu
        35                  40                  45

Ala

<210> SEQ ID NO 19
<211> LENGTH: 52
<212> TYPE: PRT
<213> ORGANISM: Artificial
<220> FEATURE:
<223> OTHER INFORMATION: Synthetic peptide sequence

<400> SEQUENCE: 19

Ser Lys Lys Lys Lys Asp Arg His Ser Asp Tyr Gln Pro Leu Gly Thr
1               5                   10                  15

Gln Asp Gln Ser Leu Tyr Leu Gly Leu Gln His Asp Gly Asn Asp Gly
            20                  25                  30

Leu Pro Pro Pro Pro Tyr Ser Pro Arg Asp Asp Ser Ser Gln His Ile
        35                  40                  45

Tyr Glu Glu Ala
    50

<210> SEQ ID NO 20
<211> LENGTH: 47
<212> TYPE: PRT
<213> ORGANISM: Artificial
<220> FEATURE:
<223> OTHER INFORMATION: Synthetic peptide sequence

<400> SEQUENCE: 20

Asp Arg His Ser Asp Tyr Gln Pro Leu Gly Thr Gln Asp Gln Ser Leu
1               5                   10                  15

Tyr Leu Gly Leu Gln His Asp Gly Asn Asp Gly Leu Pro Pro Pro Pro
            20                  25                  30

Tyr Ser Pro Arg Asp Asp Ser Ser Gln His Ile Tyr Glu Glu Ala
        35                  40                  45

<210> SEQ ID NO 21
<211> LENGTH: 40
<212> TYPE: PRT
<213> ORGANISM: Artificial
<220> FEATURE:
<223> OTHER INFORMATION: Synthetic peptide sequence
```

```
<220> FEATURE:
<221> NAME/KEY: misc_feature
<222> LOCATION: (1)..(4)
<223> OTHER INFORMATION: Xaa can be any naturally occurring amino acid

<400> SEQUENCE: 21

Xaa Xaa Xaa Xaa Leu Leu Trp Thr Leu Val Val Leu Leu Ile Cys Ser
1               5                   10                  15

Ser Cys Ser Ser Cys Pro Leu Ser Lys Ile Leu Leu Ala Arg Leu Phe
            20                  25                  30

Leu Tyr Ala Leu Ala Leu Leu Leu
        35                  40

<210> SEQ ID NO 22
<211> LENGTH: 39
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 22

Xaa Xaa Xaa Leu Leu Trp Thr Leu Val Val Leu Leu Ile Cys Ser Ser
1               5                   10                  15

Cys Ser Ser Cys Pro Leu Ser Lys Ile Leu Leu Ala Arg Leu Phe Leu
            20                  25                  30

Tyr Ala Leu Ala Leu Leu Leu
        35

<210> SEQ ID NO 23
<211> LENGTH: 38
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 23

Xaa Xaa Leu Leu Trp Thr Leu Val Val Leu Leu Ile Cys Ser Ser Cys
1               5                   10                  15

Ser Ser Cys Pro Leu Ser Lys Ile Leu Leu Ala Arg Leu Phe Leu Tyr
            20                  25                  30

Ala Leu Ala Leu Leu Leu
        35

<210> SEQ ID NO 24
<211> LENGTH: 41
<212> TYPE: PRT
<213> ORGANISM: Artificial
<220> FEATURE:
<223> OTHER INFORMATION: Synthetic peptide sequence

<400> SEQUENCE: 24

Ser Lys Lys Lys Lys Leu Leu Trp Thr Leu Val Val Leu Leu Ile Cys
1               5                   10                  15

Ser Ser Cys Ser Ser Cys Pro Leu Ser Lys Ile Leu Leu Ala Arg Leu
            20                  25                  30

Phe Leu Tyr Ala Leu Ala Leu Leu Leu
```

<210> SEQ ID NO 25
<211> LENGTH: 36
<212> TYPE: PRT
<213> ORGANISM: Artificial
<220> FEATURE:
<223> OTHER INFORMATION: Synthetic peptide sequence

<400> SEQUENCE: 25

Leu Leu Trp Thr Leu Val Val Leu Leu Ile Cys Ser Ser Cys Ser Ser
1               5                   10                  15

Cys Pro Leu Ser Lys Ile Leu Leu Ala Arg Leu Phe Leu Tyr Ala Leu
            20                  25                  30

Ala Leu Leu Leu
        35

<210> SEQ ID NO 26
<211> LENGTH: 44
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 26

Xaa Xaa Xaa Xaa Leu Met Leu Leu Trp Thr Leu Val Val Leu Leu Ile
1               5                   10                  15

Cys Ser Ser Cys Ser Ser Cys Pro Leu Ser Lys Ile Leu Leu Ala Arg
            20                  25                  30

Leu Phe Leu Tyr Ala Leu Ala Leu Leu Leu Ala
        35                  40

<210> SEQ ID NO 27
<211> LENGTH: 43
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 27

Xaa Xaa Xaa Leu Met Leu Leu Trp Thr Leu Val Val Leu Leu Ile Cys
1               5                   10                  15

Ser Ser Cys Ser Ser Cys Pro Leu Ser Lys Ile Leu Leu Ala Arg Leu
            20                  25                  30

Phe Leu Tyr Ala Leu Ala Leu Leu Leu Ala
        35                  40

<210> SEQ ID NO 28
<211> LENGTH: 42
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

```
<400> SEQUENCE: 28

Xaa Xaa Leu Met Leu Leu Trp Thr Leu Val Val Leu Leu Ile Cys Ser
1               5                   10                  15

Ser Cys Ser Ser Cys Pro Leu Ser Lys Ile Leu Leu Ala Arg Leu Phe
            20                  25                  30

Leu Tyr Ala Leu Ala Leu Leu Leu Ala
        35                  40

<210> SEQ ID NO 29
<211> LENGTH: 45
<212> TYPE: PRT
<213> ORGANISM: Artificial
<220> FEATURE:
<223> OTHER INFORMATION: Synthetic peptide sequence

<400> SEQUENCE: 29

Ser Lys Lys Lys Lys Leu Met Leu Leu Trp Thr Leu Val Val Leu Leu
1               5                   10                  15

Ile Cys Ser Ser Cys Ser Ser Cys Pro Leu Ser Lys Ile Leu Leu Ala
            20                  25                  30

Arg Leu Phe Leu Tyr Ala Leu Ala Leu Leu Leu Ala
        35                  40                  45

<210> SEQ ID NO 30
<211> LENGTH: 40
<212> TYPE: PRT
<213> ORGANISM: Artificial
<220> FEATURE:
<223> OTHER INFORMATION: Synthetic peptide sequence

<400> SEQUENCE: 30

Leu Met Leu Leu Trp Thr Leu Val Val Leu Leu Ile Cys Ser Ser Cys
1               5                   10                  15

Ser Ser Cys Pro Leu Ser Lys Ile Leu Leu Ala Arg Leu Phe Leu Tyr
            20                  25                  30

Ala Leu Ala Leu Leu Leu Ala
        35                  40

<210> SEQ ID NO 31
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 31

Xaa Xaa Xaa Xaa Leu Met Leu Leu Trp Thr Leu Val Val Leu Leu Ile
1               5                   10                  15

Cys Ser Ser Cys Ser Ser Cys Pro Leu Ser Lys Ile Leu Leu
            20                  25                  30

<210> SEQ ID NO 32
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(3)
```

<223> OTHER INFORMATION: Xaa can be any naturally occurring amino acid

<400> SEQUENCE: 32

Xaa Xaa Xaa Leu Met Leu Leu Trp Thr Leu Val Val Leu Leu Ile Cys
1               5                   10                  15

Ser Ser Cys Ser Ser Cys Pro Leu Ser Lys Ile Leu Leu
            20                  25

<210> SEQ ID NO 33
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 33

Xaa Xaa Leu Met Leu Leu Trp Thr Leu Val Val Leu Leu Ile Cys Ser
1               5                   10                  15

Ser Cys Ser Ser Cys Pro Leu Ser Lys Ile Leu Leu
            20                  25

<210> SEQ ID NO 34
<211> LENGTH: 31
<212> TYPE: PRT
<213> ORGANISM: Artificial
<220> FEATURE:
<223> OTHER INFORMATION: Synthetic peptide sequence

<400> SEQUENCE: 34

Ser Lys Lys Lys Lys Leu Met Leu Leu Trp Thr Leu Val Val Leu Leu
1               5                   10                  15

Ile Cys Ser Ser Cys Ser Ser Cys Pro Leu Ser Lys Ile Leu Leu
            20                  25                  30

<210> SEQ ID NO 35
<211> LENGTH: 26
<212> TYPE: PRT
<213> ORGANISM: Artificial
<220> FEATURE:
<223> OTHER INFORMATION: Synthetic peptide sequence

<400> SEQUENCE: 35

Leu Met Leu Leu Trp Thr Leu Val Val Leu Leu Ile Cys Ser Ser Cys
1               5                   10                  15

Ser Ser Cys Pro Leu Ser Lys Ile Leu Leu
            20                  25

<210> SEQ ID NO 36
<211> LENGTH: 35
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 36

Xaa Xaa Xaa Xaa Leu Leu Ile Cys Ser Ser Cys Ser Ser Cys Pro Leu
1               5                   10                  15

```
Ser Lys Ile Leu Leu Ala Arg Leu Phe Leu Tyr Ala Leu Ala Leu Leu
            20                  25                  30

Leu Leu Ala
        35

<210> SEQ ID NO 37
<211> LENGTH: 34
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 37

Xaa Xaa Xaa Leu Leu Ile Cys Ser Ser Cys Ser Ser Cys Pro Leu Ser
1               5                   10                  15

Lys Ile Leu Leu Ala Arg Leu Phe Leu Tyr Ala Leu Ala Leu Leu Leu
            20                  25                  30

Leu Ala

<210> SEQ ID NO 38
<211> LENGTH: 33
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 38

Xaa Xaa Leu Leu Ile Cys Ser Ser Cys Ser Ser Cys Pro Leu Ser Lys
1               5                   10                  15

Ile Leu Leu Ala Arg Leu Phe Leu Tyr Ala Leu Ala Leu Leu Leu Leu
            20                  25                  30

Ala

<210> SEQ ID NO 39
<211> LENGTH: 36
<212> TYPE: PRT
<213> ORGANISM: Artificial
<220> FEATURE:
<223> OTHER INFORMATION: Synthetic peptide sequence

<400> SEQUENCE: 39

Ser Lys Lys Lys Lys Leu Leu Ile Cys Ser Ser Cys Ser Ser Cys Pro
1               5                   10                  15

Leu Ser Lys Ile Leu Leu Ala Arg Leu Phe Leu Tyr Ala Leu Ala Leu
            20                  25                  30

Leu Leu Leu Ala
        35

<210> SEQ ID NO 40
<211> LENGTH: 31
<212> TYPE: PRT
<213> ORGANISM: Artificial
<220> FEATURE:
<223> OTHER INFORMATION: Synthetic peptide sequence

<400> SEQUENCE: 40
```

```
Leu Leu Ile Cys Ser Ser Cys Ser Ser Cys Pro Leu Ser Lys Ile Leu
1               5                   10                  15

Leu Ala Arg Leu Phe Leu Tyr Ala Leu Ala Leu Leu Leu Ala
            20                  25                  30

<210> SEQ ID NO 41
<211> LENGTH: 61
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 41

Xaa Xaa Xaa Xaa Leu Asn Leu Thr Thr Met Phe Leu Leu Met Leu Leu
1               5                   10                  15

Trp Thr Leu Val Val Leu Leu Ile Cys Ser Ser Cys Ser Ser Cys Pro
            20                  25                  30

Leu Ser Lys Ile Leu Leu Ala Arg Leu Phe Leu Tyr Ala Leu Ala Leu
        35                  40                  45

Leu Leu Ala Ser Ala Leu Ile Ala Gly Gly Ser Ile
    50                  55                  60

<210> SEQ ID NO 42
<211> LENGTH: 60
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 42

Xaa Xaa Xaa Leu Asn Leu Thr Thr Met Phe Leu Leu Met Leu Leu Trp
1               5                   10                  15

Thr Leu Val Val Leu Leu Ile Cys Ser Ser Cys Ser Ser Cys Pro Leu
            20                  25                  30

Ser Lys Ile Leu Leu Ala Arg Leu Phe Leu Tyr Ala Leu Ala Leu Leu
        35                  40                  45

Leu Ala Ser Ala Leu Ile Ala Gly Gly Ser Ile
    50                  55                  60

<210> SEQ ID NO 43
<211> LENGTH: 59
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 43

Xaa Xaa Leu Asn Leu Thr Thr Met Phe Leu Leu Met Leu Leu Trp Thr
1               5                   10                  15

Leu Val Val Leu Leu Ile Cys Ser Ser Cys Ser Ser Cys Pro Leu Ser
            20                  25                  30

Lys Ile Leu Leu Ala Arg Leu Phe Leu Tyr Ala Leu Ala Leu Leu Leu
```

```
                      35                  40                  45

Leu Ala Ser Ala Leu Ile Ala Gly Gly Ser Ile
    50                  55

<210> SEQ ID NO 44
<211> LENGTH: 62
<212> TYPE: PRT
<213> ORGANISM: Artificial
<220> FEATURE:
<223> OTHER INFORMATION: Synthetic peptide sequence

<400> SEQUENCE: 44

Ser Lys Lys Lys Lys Leu Asn Leu Thr Thr Met Phe Leu Leu Met Leu
1               5                   10                  15

Leu Trp Thr Leu Val Val Leu Leu Ile Cys Ser Ser Cys Ser Ser Cys
            20                  25                  30

Pro Leu Ser Lys Ile Leu Leu Ala Arg Leu Phe Leu Tyr Ala Leu Ala
        35                  40                  45

Leu Leu Leu Leu Ala Ser Ala Leu Ile Ala Gly Gly Ser Ile
    50                  55                  60

<210> SEQ ID NO 45
<211> LENGTH: 57
<212> TYPE: PRT
<213> ORGANISM: Artificial
<220> FEATURE:
<223> OTHER INFORMATION: Synthetic peptide sequence

<400> SEQUENCE: 45

Leu Asn Leu Thr Thr Met Phe Leu Leu Met Leu Leu Trp Thr Leu Val
1               5                   10                  15

Val Leu Leu Ile Cys Ser Ser Cys Ser Ser Cys Pro Leu Ser Lys Ile
            20                  25                  30

Leu Leu Ala Arg Leu Phe Leu Tyr Ala Leu Ala Leu Leu Leu Leu Ala
        35                  40                  45

Ser Ala Leu Ile Ala Gly Gly Ser Ile
    50                  55

<210> SEQ ID NO 46
<211> LENGTH: 48
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 46

Xaa Xaa Xaa Xaa Phe Leu Leu Met Leu Leu Trp Thr Leu Val Val Leu
1               5                   10                  15

Leu Ile Cys Ser Ser Cys Ser Ser Cys Pro Leu Ser Lys Ile Leu Leu
            20                  25                  30

Ala Arg Leu Phe Leu Tyr Ala Leu Ala Leu Leu Leu Leu Ala Ser Ala
        35                  40                  45

<210> SEQ ID NO 47
<211> LENGTH: 47
<212> TYPE: PRT
<213> ORGANISM: Artificial
<220> FEATURE:
<223> OTHER INFORMATION: Synthetic peptide sequence
```

```
<220> FEATURE:
<221> NAME/KEY: misc_feature
<222> LOCATION: (1)..(3)
<223> OTHER INFORMATION: Xaa can be any naturally occurring amino acid

<400> SEQUENCE: 47

Xaa Xaa Xaa Phe Leu Leu Met Leu Leu Trp Thr Leu Val Val Leu Leu
1               5                   10                  15

Ile Cys Ser Ser Cys Ser Ser Cys Pro Leu Ser Lys Ile Leu Leu Ala
            20                  25                  30

Arg Leu Phe Leu Tyr Ala Leu Ala Leu Leu Leu Leu Ala Ser Ala
        35                  40                  45

<210> SEQ ID NO 48
<211> LENGTH: 46
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 48

Xaa Xaa Phe Leu Leu Met Leu Leu Trp Thr Leu Val Val Leu Leu Ile
1               5                   10                  15

Cys Ser Ser Cys Ser Ser Cys Pro Leu Ser Lys Ile Leu Leu Ala Arg
            20                  25                  30

Leu Phe Leu Tyr Ala Leu Ala Leu Leu Leu Leu Ala Ser Ala
        35                  40                  45

<210> SEQ ID NO 49
<211> LENGTH: 49
<212> TYPE: PRT
<213> ORGANISM: Artificial
<220> FEATURE:
<223> OTHER INFORMATION: Synthetic peptide sequence

<400> SEQUENCE: 49

Ser Lys Lys Lys Lys Phe Leu Leu Met Leu Leu Trp Thr Leu Val Val
1               5                   10                  15

Leu Leu Ile Cys Ser Ser Cys Ser Ser Cys Pro Leu Ser Lys Ile Leu
            20                  25                  30

Leu Ala Arg Leu Phe Leu Tyr Ala Leu Ala Leu Leu Leu Leu Ala Ser
        35                  40                  45

Ala

<210> SEQ ID NO 50
<211> LENGTH: 44
<212> TYPE: PRT
<213> ORGANISM: Artificial
<220> FEATURE:
<223> OTHER INFORMATION: Synthetic peptide sequence

<400> SEQUENCE: 50

Phe Leu Leu Met Leu Leu Trp Thr Leu Val Val Leu Leu Ile Cys Ser
1               5                   10                  15

Ser Cys Ser Ser Cys Pro Leu Ser Lys Ile Leu Leu Ala Arg Leu Phe
            20                  25                  30

Leu Tyr Ala Leu Ala Leu Leu Leu Leu Ala Ser Ala
        35                  40
```

```
<210> SEQ ID NO 51
<211> LENGTH: 55
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 51

Xaa Xaa Xaa Xaa Leu Gln Gly Ile Tyr Val Leu Val Met Leu Val Leu
1               5                   10                  15

Leu Ile Leu Ala Tyr Arg Arg Arg Trp Arg Arg Leu Thr Val Cys Gly
            20                  25                  30

Gly Ile Met Phe Leu Ala Cys Val Leu Val Leu Ile Val Asp Ala Val
        35                  40                  45

Leu Gln Leu Ser Pro Leu Leu
    50                  55

<210> SEQ ID NO 52
<211> LENGTH: 54
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 52

Xaa Xaa Xaa Leu Gln Gly Ile Tyr Val Leu Val Met Leu Val Leu Leu
1               5                   10                  15

Ile Leu Ala Tyr Arg Arg Arg Trp Arg Arg Leu Thr Val Cys Gly Gly
            20                  25                  30

Ile Met Phe Leu Ala Cys Val Leu Val Leu Ile Val Asp Ala Val Leu
        35                  40                  45

Gln Leu Ser Pro Leu Leu
    50

<210> SEQ ID NO 53
<211> LENGTH: 53
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 53

Xaa Xaa Leu Gln Gly Ile Tyr Val Leu Val Met Leu Val Leu Leu Ile
1               5                   10                  15

Leu Ala Tyr Arg Arg Arg Trp Arg Arg Leu Thr Val Cys Gly Gly Ile
            20                  25                  30

Met Phe Leu Ala Cys Val Leu Val Leu Ile Val Asp Ala Val Leu Gln
        35                  40                  45

Leu Ser Pro Leu Leu
    50
```

-continued

```
<210> SEQ ID NO 54
<211> LENGTH: 56
<212> TYPE: PRT
<213> ORGANISM: Artificial
<220> FEATURE:
<223> OTHER INFORMATION: Synthetic peptide sequence

<400> SEQUENCE: 54

Ser Lys Lys Lys Lys Leu Gln Gly Ile Tyr Val Leu Val Met Leu Val
1               5                   10                  15

Leu Leu Ile Leu Ala Tyr Arg Arg Arg Trp Arg Arg Leu Thr Val Cys
            20                  25                  30

Gly Gly Ile Met Phe Leu Ala Cys Val Leu Val Leu Ile Val Asp Ala
        35                  40                  45

Val Leu Gln Leu Ser Pro Leu Leu
    50                  55

<210> SEQ ID NO 55
<211> LENGTH: 51
<212> TYPE: PRT
<213> ORGANISM: Artificial
<220> FEATURE:
<223> OTHER INFORMATION: Synthetic peptide sequence

<400> SEQUENCE: 55

Leu Gln Gly Ile Tyr Val Leu Val Met Leu Val Leu Leu Ile Leu Ala
1               5                   10                  15

Tyr Arg Arg Arg Trp Arg Arg Leu Thr Val Cys Gly Gly Ile Met Phe
            20                  25                  30

Leu Ala Cys Val Leu Val Leu Ile Val Asp Ala Val Leu Gln Leu Ser
        35                  40                  45

Pro Leu Leu
    50

<210> SEQ ID NO 56
<211> LENGTH: 56
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 56

Xaa Xaa Xaa Xaa Ser Gly Asn Arg Thr Tyr Gly Pro Val Phe Met Cys
1               5                   10                  15

Ser Leu Gly Gly Leu Leu Thr Met Val Ala Gly Ala Val Trp Leu Thr
            20                  25                  30

Val Met Ser Asn Thr Leu Leu Ser Ala Trp Ile Leu Thr Ala Gly Phe
        35                  40                  45

Leu Ile Phe Leu Ile Gly Phe Ala
    50                  55

<210> SEQ ID NO 57
<211> LENGTH: 55
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(3)
```

<223> OTHER INFORMATION: Xaa can be any naturally occurring amino acid

<400> SEQUENCE: 57

Xaa Xaa Xaa Ser Gly Asn Arg Thr Tyr Gly Pro Val Phe Met Cys Ser
1               5                   10                  15

Leu Gly Gly Leu Leu Thr Met Val Ala Gly Ala Val Trp Leu Thr Val
            20                  25                  30

Met Ser Asn Thr Leu Leu Ser Ala Trp Ile Leu Thr Ala Gly Phe Leu
        35                  40                  45

Ile Phe Leu Ile Gly Phe Ala
    50                  55

<210> SEQ ID NO 58
<211> LENGTH: 54
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 58

Xaa Xaa Ser Gly Asn Arg Thr Tyr Gly Pro Val Phe Met Cys Ser Leu
1               5                   10                  15

Gly Gly Leu Leu Thr Met Val Ala Gly Ala Val Trp Leu Thr Val Met
            20                  25                  30

Ser Asn Thr Leu Leu Ser Ala Trp Ile Leu Thr Ala Gly Phe Leu Ile
        35                  40                  45

Phe Leu Ile Gly Phe Ala
    50

<210> SEQ ID NO 59
<211> LENGTH: 57
<212> TYPE: PRT
<213> ORGANISM: Artificial
<220> FEATURE:
<223> OTHER INFORMATION: Synthetic peptide sequence

<400> SEQUENCE: 59

Ser Lys Lys Lys Ser Gly Asn Arg Thr Tyr Gly Pro Val Phe Met
1               5                   10                  15

Cys Ser Leu Gly Gly Leu Leu Thr Met Val Ala Gly Ala Val Trp Leu
            20                  25                  30

Thr Val Met Ser Asn Thr Leu Leu Ser Ala Trp Ile Leu Thr Ala Gly
        35                  40                  45

Phe Leu Ile Phe Leu Ile Gly Phe Ala
    50                  55

<210> SEQ ID NO 60
<211> LENGTH: 52
<212> TYPE: PRT
<213> ORGANISM: Artificial
<220> FEATURE:
<223> OTHER INFORMATION: Synthetic peptide sequence

<400> SEQUENCE: 60

Ser Gly Asn Arg Thr Tyr Gly Pro Val Phe Met Cys Ser Leu Gly Gly
1               5                   10                  15

Leu Leu Thr Met Val Ala Gly Ala Val Trp Leu Thr Val Met Ser Asn
            20                  25                  30

```
Thr Leu Leu Ser Ala Trp Ile Leu Thr Ala Gly Phe Leu Ile Phe Leu
        35                  40                  45

Ile Gly Phe Ala
    50

<210> SEQ ID NO 61
<211> LENGTH: 51
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 61

Xaa Xaa Xaa Xaa Ser Asn Glu Glu Pro Pro Pro Tyr Glu Asp Pro
1               5                   10                  15

Tyr Trp Gly Asn Gly Asp Arg His Ser Asp Tyr Gln Pro Leu Gly Thr
            20                  25                  30

Gln Asp Gln Ser Leu Tyr Leu Gly Leu Gln His Asp Gly Asn Asp Gly
        35                  40                  45

Leu Pro Pro
    50

<210> SEQ ID NO 62
<211> LENGTH: 50
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 62

Xaa Xaa Xaa Ser Asn Glu Glu Pro Pro Pro Tyr Glu Asp Pro Tyr
1               5                   10                  15

Trp Gly Asn Gly Asp Arg His Ser Asp Tyr Gln Pro Leu Gly Thr Gln
            20                  25                  30

Asp Gln Ser Leu Tyr Leu Gly Leu Gln His Asp Gly Asn Asp Gly Leu
        35                  40                  45

Pro Pro
    50

<210> SEQ ID NO 63
<211> LENGTH: 49
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 63

Xaa Xaa Ser Asn Glu Glu Pro Pro Pro Tyr Glu Asp Pro Tyr Trp
1               5                   10                  15

Gly Asn Gly Asp Arg His Ser Asp Tyr Gln Pro Leu Gly Thr Gln Asp
            20                  25                  30
```

-continued

Gln Ser Leu Tyr Leu Gly Leu Gln His Asp Gly Asn Asp Gly Leu Pro
            35                  40                  45

Pro

<210> SEQ ID NO 64
<211> LENGTH: 52
<212> TYPE: PRT
<213> ORGANISM: Artificial
<220> FEATURE:
<223> OTHER INFORMATION: Synthetic peptide sequence

<400> SEQUENCE: 64

Ser Lys Lys Lys Lys Ser Asn Glu Glu Pro Pro Pro Tyr Glu Asp
1               5                   10                  15

Pro Tyr Trp Gly Asn Gly Asp Arg His Ser Asp Tyr Gln Pro Leu Gly
            20                  25                  30

Thr Gln Asp Gln Ser Leu Tyr Leu Gly Leu Gln His Asp Gly Asn Asp
            35                  40                  45

Gly Leu Pro Pro
    50

<210> SEQ ID NO 65
<211> LENGTH: 47
<212> TYPE: PRT
<213> ORGANISM: Artificial
<220> FEATURE:
<223> OTHER INFORMATION: Synthetic peptide sequence

<400> SEQUENCE: 65

Ser Asn Glu Glu Pro Pro Pro Pro Tyr Glu Asp Pro Tyr Trp Gly Asn
1               5                   10                  15

Gly Asp Arg His Ser Asp Tyr Gln Pro Leu Gly Thr Gln Asp Gln Ser
            20                  25                  30

Leu Tyr Leu Gly Leu Gln His Asp Gly Asn Asp Gly Leu Pro Pro
            35                  40                  45

<210> SEQ ID NO 66
<211> LENGTH: 55
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 66

Xaa Xaa Xaa Xaa Gly Asn Asp Gly Leu Pro Pro Pro Tyr Ser Pro
1               5                   10                  15

Arg Asp Asp Ser Ser Gln His Ile Tyr Glu Glu Ala Gly Arg Gly Ser
            20                  25                  30

Met Asn Pro Val Cys Leu Pro Val Ile Val Ala Pro Tyr Leu Phe Trp
            35                  40                  45

Leu Ala Ala Ile Ala Ala Ser
    50                  55

<210> SEQ ID NO 67
<211> LENGTH: 54
<212> TYPE: PRT
<213> ORGANISM: Artificial
<220> FEATURE:
<223> OTHER INFORMATION: Synthetic peptide sequence

```
<220> FEATURE:
<221> NAME/KEY: misc_feature
<222> LOCATION: (1)..(3)
<223> OTHER INFORMATION: Xaa can be any naturally occurring amino acid

<400> SEQUENCE: 67

Xaa Xaa Xaa Gly Asn Asp Gly Leu Pro Pro Pro Tyr Ser Pro Arg
1               5                   10                  15

Asp Asp Ser Ser Gln His Ile Tyr Glu Glu Ala Gly Arg Gly Ser Met
            20                  25                  30

Asn Pro Val Cys Leu Pro Val Ile Val Ala Pro Tyr Leu Phe Trp Leu
        35                  40                  45

Ala Ala Ile Ala Ala Ser
    50

<210> SEQ ID NO 68
<211> LENGTH: 53
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 68

Xaa Xaa Gly Asn Asp Gly Leu Pro Pro Pro Tyr Ser Pro Arg Asp
1               5                   10                  15

Asp Ser Ser Gln His Ile Tyr Glu Glu Ala Gly Arg Gly Ser Met Asn
            20                  25                  30

Pro Val Cys Leu Pro Val Ile Val Ala Pro Tyr Leu Phe Trp Leu Ala
        35                  40                  45

Ala Ile Ala Ala Ser
    50

<210> SEQ ID NO 69
<211> LENGTH: 56
<212> TYPE: PRT
<213> ORGANISM: Artificial
<220> FEATURE:
<223> OTHER INFORMATION: Synthetic peptide sequence

<400> SEQUENCE: 69

Ser Lys Lys Lys Lys Gly Asn Asp Gly Leu Pro Pro Pro Tyr Ser
1               5                   10                  15

Pro Arg Asp Asp Ser Ser Gln His Ile Tyr Glu Glu Ala Gly Arg Gly
            20                  25                  30

Ser Met Asn Pro Val Cys Leu Pro Val Ile Val Ala Pro Tyr Leu Phe
        35                  40                  45

Trp Leu Ala Ala Ile Ala Ala Ser
    50                  55

<210> SEQ ID NO 70
<211> LENGTH: 51
<212> TYPE: PRT
<213> ORGANISM: Artificial
<220> FEATURE:
<223> OTHER INFORMATION: Synthetic peptide sequence

<400> SEQUENCE: 70

Gly Asn Asp Gly Leu Pro Pro Pro Tyr Ser Pro Arg Asp Asp Ser
1               5                   10                  15
```

Ser Gln His Ile Tyr Glu Glu Ala Gly Arg Gly Ser Met Asn Pro Val
            20                  25                  30

Cys Leu Pro Val Ile Val Ala Pro Tyr Leu Phe Trp Leu Ala Ala Ile
        35                  40                  45

Ala Ala Ser
    50

<210> SEQ ID NO 71
<211> LENGTH: 54
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 71

Xaa Xaa Xaa Xaa Ala Ala Ile Ala Ala Ser Cys Phe Thr Ala Ser Val
1               5                   10                  15

Ser Thr Val Val Thr Ala Thr Gly Leu Ala Leu Ser Leu Leu Leu Leu
            20                  25                  30

Ala Ala Val Ala Ser Ser Tyr Ala Ala Ala Gln Arg Lys Leu Leu Thr
        35                  40                  45

Pro Val Thr Val Leu Thr
    50

<210> SEQ ID NO 72
<211> LENGTH: 53
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 72

Xaa Xaa Xaa Ala Ala Ile Ala Ala Ser Cys Phe Thr Ala Ser Val Ser
1               5                   10                  15

Thr Val Val Thr Ala Thr Gly Leu Ala Leu Ser Leu Leu Leu Leu Ala
            20                  25                  30

Ala Val Ala Ser Ser Tyr Ala Ala Ala Gln Arg Lys Leu Leu Thr Pro
        35                  40                  45

Val Thr Val Leu Thr
    50

<210> SEQ ID NO 73
<211> LENGTH: 52
<212> TYPE: PRT
<213> ORGANISM: Artificial
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 73

Xaa Xaa Ala Ala Ile Ala Ala Ser Cys Phe Thr Ala Ser Val Ser Thr
1               5                   10                  15

```
Val Val Thr Ala Thr Gly Leu Ala Leu Ser Leu Leu Leu Ala Ala
            20                  25                  30

Val Ala Ser Ser Tyr Ala Ala Ala Gln Arg Lys Leu Leu Thr Pro Val
        35                  40                  45

Thr Val Leu Thr
    50

<210> SEQ ID NO 74
<211> LENGTH: 55
<212> TYPE: PRT
<213> ORGANISM: Artificial
<220> FEATURE:
<223> OTHER INFORMATION: Synthetic peptide sequence

<400> SEQUENCE: 74

Ser Lys Lys Lys Lys Ala Ala Ile Ala Ala Ser Cys Phe Thr Ala Ser
1               5                   10                  15

Val Ser Thr Val Val Thr Ala Thr Gly Leu Ala Leu Ser Leu Leu Leu
            20                  25                  30

Leu Ala Ala Val Ala Ser Ser Tyr Ala Ala Ala Gln Arg Lys Leu Leu
        35                  40                  45

Thr Pro Val Thr Val Leu Thr
    50                  55

<210> SEQ ID NO 75
<211> LENGTH: 50
<212> TYPE: PRT
<213> ORGANISM: Artificial
<220> FEATURE:
<223> OTHER INFORMATION: Synthetic peptide sequence

<400> SEQUENCE: 75

Ala Ala Ile Ala Ala Ser Cys Phe Thr Ala Ser Val Ser Thr Val Val
1               5                   10                  15

Thr Ala Thr Gly Leu Ala Leu Ser Leu Leu Leu Ala Ala Val Ala
            20                  25                  30

Ser Ser Tyr Ala Ala Ala Gln Arg Lys Leu Leu Thr Pro Val Thr Val
        35                  40                  45

Leu Thr
    50

<210> SEQ ID NO 76
<211> LENGTH: 10
<212> TYPE: PRT
<213> ORGANISM: Artificial
<220> FEATURE:
<223> OTHER INFORMATION: Synthetic peptide sequence

<400> SEQUENCE: 76

Glu Ser Asn Glu Glu Pro Pro Pro Pro Tyr
1               5                   10

<210> SEQ ID NO 77
<211> LENGTH: 9
<212> TYPE: PRT
<213> ORGANISM: Artificial
<220> FEATURE:
<223> OTHER INFORMATION: Synthetic peptide sequence

<400> SEQUENCE: 77

Ser Asn Glu Glu Pro Pro Pro Pro Tyr
1               5
```

```
<210> SEQ ID NO 78
<211> LENGTH: 9
<212> TYPE: PRT
<213> ORGANISM: Artificial
<220> FEATURE:
<223> OTHER INFORMATION: Synthetic peptide sequence

<400> SEQUENCE: 78

His Ser Asp Tyr Gln Pro Leu Gly Thr
1               5

<210> SEQ ID NO 79
<211> LENGTH: 9
<212> TYPE: PRT
<213> ORGANISM: Artificial
<220> FEATURE:
<223> OTHER INFORMATION: Synthetic peptide sequence

<400> SEQUENCE: 79

Pro Leu Gly Thr Gln Asp Gln Ser Leu
1               5

<210> SEQ ID NO 80
<211> LENGTH: 10
<212> TYPE: PRT
<213> ORGANISM: Artificial
<220> FEATURE:
<223> OTHER INFORMATION: Synthetic peptide sequence

<400> SEQUENCE: 80

Pro Leu Gly Thr Gln Asp Gln Ser Leu Tyr
1               5                   10

<210> SEQ ID NO 81
<211> LENGTH: 9
<212> TYPE: PRT
<213> ORGANISM: Artificial
<220> FEATURE:
<223> OTHER INFORMATION: Synthetic peptide sequence

<400> SEQUENCE: 81

Leu Gly Thr Gln Asp Gln Ser Leu Tyr
1               5

<210> SEQ ID NO 82
<211> LENGTH: 9
<212> TYPE: PRT
<213> ORGANISM: Artificial
<220> FEATURE:
<223> OTHER INFORMATION: Synthetic peptide sequence

<400> SEQUENCE: 82

Gly Thr Gln Asp Gln Ser Leu Tyr Leu
1               5

<210> SEQ ID NO 83
<211> LENGTH: 9
<212> TYPE: PRT
<213> ORGANISM: Artificial
<220> FEATURE:
<223> OTHER INFORMATION: Synthetic peptide sequence

<400> SEQUENCE: 83

Gly Thr Gln Asp Gln Ser Leu Tyr Leu
1               5
```

```
<210> SEQ ID NO 84
<211> LENGTH: 10
<212> TYPE: PRT
<213> ORGANISM: Artificial
<220> FEATURE:
<223> OTHER INFORMATION: Synthetic peptide sequence

<400> SEQUENCE: 84

Gly Thr Gln Asp Gln Ser Leu Tyr Leu Gly
1               5                   10

<210> SEQ ID NO 85
<211> LENGTH: 9
<212> TYPE: PRT
<213> ORGANISM: Artificial
<220> FEATURE:
<223> OTHER INFORMATION: Synthetic peptide sequence

<400> SEQUENCE: 85

Gln Ser Leu Tyr Leu Gly Leu Gln His
1               5

<210> SEQ ID NO 86
<211> LENGTH: 9
<212> TYPE: PRT
<213> ORGANISM: Artificial
<220> FEATURE:
<223> OTHER INFORMATION: Synthetic peptide sequence

<400> SEQUENCE: 86

Ser Leu Tyr Leu Gly Leu Gln His Asp
1               5

<210> SEQ ID NO 87
<211> LENGTH: 10
<212> TYPE: PRT
<213> ORGANISM: Artificial
<220> FEATURE:
<223> OTHER INFORMATION: Synthetic peptide sequence

<400> SEQUENCE: 87

Gly Leu Gln His Asp Gly Asn Asp Gly Leu
1               5                   10

<210> SEQ ID NO 88
<211> LENGTH: 10
<212> TYPE: PRT
<213> ORGANISM: Artificial
<220> FEATURE:
<223> OTHER INFORMATION: Synthetic peptide sequence

<400> SEQUENCE: 88

Gly Asn Asp Gly Leu Pro Pro Pro Pro Tyr
1               5                   10

<210> SEQ ID NO 89
<211> LENGTH: 9
<212> TYPE: PRT
<213> ORGANISM: Artificial
<220> FEATURE:
<223> OTHER INFORMATION: Synthetic peptide sequence

<400> SEQUENCE: 89

Gly Leu Pro Pro Pro Pro Tyr Ser Pro
1               5

<210> SEQ ID NO 90
```

```
<211> LENGTH: 10
<212> TYPE: PRT
<213> ORGANISM: Artificial
<220> FEATURE:
<223> OTHER INFORMATION: Synthetic peptide sequence

<400> SEQUENCE: 90

Gly Leu Pro Pro Pro Tyr Ser Pro Arg
1               5                   10

<210> SEQ ID NO 91
<211> LENGTH: 10
<212> TYPE: PRT
<213> ORGANISM: Artificial
<220> FEATURE:
<223> OTHER INFORMATION: Synthetic peptide sequence

<400> SEQUENCE: 91

Pro Arg Asp Asp Ser Ser Gln His Ile Tyr
1               5                   10

<210> SEQ ID NO 92
<211> LENGTH: 9
<212> TYPE: PRT
<213> ORGANISM: Artificial
<220> FEATURE:
<223> OTHER INFORMATION: Synthetic peptide sequence

<400> SEQUENCE: 92

Arg Asp Asp Ser Ser Gln His Ile Tyr
1               5

<210> SEQ ID NO 93
<211> LENGTH: 9
<212> TYPE: PRT
<213> ORGANISM: Artificial
<220> FEATURE:
<223> OTHER INFORMATION: Synthetic peptide sequence

<400> SEQUENCE: 93

His Ile Tyr Glu Glu Ala Gly Arg Gly
1               5

<210> SEQ ID NO 94
<211> LENGTH: 9
<212> TYPE: PRT
<213> ORGANISM: Artificial
<220> FEATURE:
<223> OTHER INFORMATION: Synthetic peptide sequence

<400> SEQUENCE: 94

Ile Leu Leu Ala Arg Leu Phe Leu Tyr
1               5

<210> SEQ ID NO 95
<211> LENGTH: 11
<212> TYPE: PRT
<213> ORGANISM: Artificial
<220> FEATURE:
<223> OTHER INFORMATION: Synthetic peptide sequence

<400> SEQUENCE: 95

Ser Ser Cys Ser Ser Cys Pro Leu Ser Lys Ile
1               5                   10

<210> SEQ ID NO 96
<211> LENGTH: 9
```

```
<212> TYPE: PRT
<213> ORGANISM: Artificial
<220> FEATURE:
<223> OTHER INFORMATION: Synthetic peptide sequence

<400> SEQUENCE: 96

Leu Leu Trp Thr Leu Val Val Leu Leu
1               5

<210> SEQ ID NO 97
<211> LENGTH: 9
<212> TYPE: PRT
<213> ORGANISM: Artificial
<220> FEATURE:
<223> OTHER INFORMATION: Synthetic peptide sequence

<400> SEQUENCE: 97

Phe Leu Tyr Ala Leu Ala Leu Leu Leu
1               5

<210> SEQ ID NO 98
<211> LENGTH: 9
<212> TYPE: PRT
<213> ORGANISM: Artificial
<220> FEATURE:
<223> OTHER INFORMATION: Synthetic peptide sequence

<400> SEQUENCE: 98

Cys Leu Gly Gly Leu Leu Thr Met Val
1               5

<210> SEQ ID NO 99
<211> LENGTH: 9
<212> TYPE: PRT
<213> ORGANISM: Artificial
<220> FEATURE:
<223> OTHER INFORMATION: Synthetic peptide sequence

<400> SEQUENCE: 99

Leu Ile Val Asp Ala Val Leu Gln Leu
1               5

<210> SEQ ID NO 100
<211> LENGTH: 9
<212> TYPE: PRT
<213> ORGANISM: Artificial
<220> FEATURE:
<223> OTHER INFORMATION: Synthetic peptide sequence

<400> SEQUENCE: 100

Leu Thr Ala Gly Phe Leu Ile Phe Leu
1               5

<210> SEQ ID NO 101
<211> LENGTH: 9
<212> TYPE: PRT
<213> ORGANISM: Artificial
<220> FEATURE:
<223> OTHER INFORMATION: Synthetic peptide sequence

<400> SEQUENCE: 101

Thr Val Cys Gly Gly Ile Met Phe Leu
1               5

<210> SEQ ID NO 102
<211> LENGTH: 34
<212> TYPE: PRT
```

<213> ORGANISM: Artificial
<220> FEATURE:
<223> OTHER INFORMATION: Synthetic peptide sequence

<400> SEQUENCE: 102

Cys Ser Lys Lys Lys Asp Arg His Ser Asp Tyr Gln Pro Leu Gly
1               5                   10                  15

Thr Gln Asp Gln Ser Leu Tyr Leu Gly Leu Gln His Asp Gly Asn Asp
            20                  25                  30

Gly Leu

<210> SEQ ID NO 103
<211> LENGTH: 6
<212> TYPE: PRT
<213> ORGANISM: Artificial
<220> FEATURE:
<223> OTHER INFORMATION: Synthetic peptide sequence

<400> SEQUENCE: 103

Cys Ser Lys Lys Lys Lys
1               5

<210> SEQ ID NO 104
<211> LENGTH: 38
<212> TYPE: PRT
<213> ORGANISM: Artificial
<220> FEATURE:
<223> OTHER INFORMATION: Synthetic peptide sequence

<400> SEQUENCE: 104

Cys Ser Lys Lys Lys Ser Leu Tyr Leu Gly Leu Gln His Asp Gly Asn
1               5                   10                  15

Asp Gly Leu Pro Pro Pro Pro Tyr Ser Pro Arg Asp Asp Ser Ser Gln
            20                  25                  30

His Ile Tyr Glu Glu Ala
        35

<210> SEQ ID NO 105
<211> LENGTH: 31
<212> TYPE: PRT
<213> ORGANISM: Artificial
<220> FEATURE:
<223> OTHER INFORMATION: Synthetic peptide sequence

<400> SEQUENCE: 105

Cys Ser Lys Lys Lys Ser Asp Tyr Gln Pro Leu Gly Thr Gln Asp
1               5                   10                  15

Gln Ser Leu Tyr Leu Gly Leu Gln His Asp Gly Asn Asp Gly Leu
            20                  25                  30

<210> SEQ ID NO 106
<211> LENGTH: 46
<212> TYPE: PRT
<213> ORGANISM: Artificial
<220> FEATURE:
<223> OTHER INFORMATION: Synthetic peptide sequence

<400> SEQUENCE: 106

Cys Ser Lys Lys Lys Lys Leu Met Leu Leu Trp Thr Leu Val Val Leu
1               5                   10                  15

Leu Ile Cys Ser Ser Cys Ser Ser Cys Pro Leu Ser Lys Ile Leu Leu
            20                  25                  30

Ala Arg Leu Phe Leu Tyr Ala Leu Ala Leu Leu Leu Leu Ala

```
<210> SEQ ID NO 107
<211> LENGTH: 50
<212> TYPE: PRT
<213> ORGANISM: Artificial
<220> FEATURE:
<223> OTHER INFORMATION: Synthetic peptide sequence

<400> SEQUENCE: 107

Cys Ser Lys Lys Lys Lys Ser Asp Tyr Gln Pro Leu Gly Thr Gln Asp
1               5                   10                  15

Gln Ser Leu Tyr Leu Gly Leu Gln His Asp Gly Asn Asp Gly Leu Pro
            20                  25                  30

Pro Pro Pro Tyr Ser Pro Arg Asp Asp Ser Ser Gln His Ile Tyr Glu
        35                  40                  45

Glu Ala
    50
```